US012766104B2

(12) United States Patent
Zhang et al.

(10) Patent No.: US 12,766,104 B2
(45) **Date of Patent: *Oct. 20, 2026**

(54) MEMBRANE ENCAPSULATED NANOPARTICLES AND METHOD OF USE

(71) Applicant: The Regents of the University of California, Oakland, CA (US)

(72) Inventors: Liangfang Zhang, San Diego, CA (US); Che-Ming (Jack) Hu, San Diego, CA (US); Ronnie Hongbo Fang, Irvine, CA (US); Jonathan Copp, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 59 days.

This patent is subject to a terminal disclaimer.

(21) Appl. No.: 18/582,123

(22) Filed: Feb. 20, 2024

(65) Prior Publication Data

US 2024/0252438 A1 Aug. 1, 2024

Related U.S. Application Data

(60) Division of application No. 13/827,906, filed on Mar. 14, 2013, now Pat. No. 12,097,290, which is a (Continued)

(51) Int. Cl.

| | |
|---|---|
| ***A61K 9/14*** | (2006.01) |
| ***A61K 39/00*** | (2006.01) |

(Continued)

(52) U.S. Cl.

CPC ...... *A61K 9/148* (2013.01); *A61K 39/001102* (2018.08); *A61K 39/085* (2013.01);

(Continued)

(58) Field of Classification Search

None

See application file for complete search history.

(56) References Cited

U.S. PATENT DOCUMENTS

| | | | |
|---|---|---|---|
| 5,358,722 | A | 10/1994 | Monzyk |
| 5,491,219 | A | 2/1996 | Mann |

(Continued)

FOREIGN PATENT DOCUMENTS

| | | | |
|---|---|---|---|
| CN | 1798548 | A | 7/2006 |
| GB | 2482069 | A | 1/2012 |

(Continued)

OTHER PUBLICATIONS

Carl M. Cohen et al. "Membrane Isolate on Polylysine-Coated Beads." The Journal of Cell Biology, vol. 75, 1977, pp. 119-134. (Year: 1977).*

(Continued)

*Primary Examiner* — Isaac Shomer

(74) *Attorney, Agent, or Firm* — Eversheds-Sutherland (US) LLP

(57) ABSTRACT

Provided are nanoparticles and methods of using and making thereof. The inventive nanoparticle comprises a) an inner core comprising a non-cellular material; and b) an outer surface comprising a cellular membrane derived from a cell or a membrane derived from a virus. Medicament delivery systems or pharmaceutical compositions comprising the inventive nanoparticles are also provided. Further provided are immunogenic compositions comprising the inventive nanoparticles, and methods of using the inventive immunogenic compositions for eliciting an immune response, and for treating or preventing diseases or condition, such as neoplasm or cancer, or disease or conditions associated with (Continued)

cell membrane inserting toxin. Vaccines comprising the immunogenic composition comprising the nanoparticles are also provided.

21 Claims, 32 Drawing Sheets

Related U.S. Application Data continuation-in-part of application No. PCT/US2012/039411, filed on May 24, 2012.

(60) Provisional application No. 61/492,626, filed on Jun. 2, 2011.

(51) Int. Cl.
*A61K 39/085* (2006.01)
*A61K 39/39* (2006.01)
*A61K 45/06* (2006.01)

(52) U.S. Cl.
CPC .............. *A61K 39/39* (2013.01); *A61K 45/06* (2013.01); *A61K 2039/55555* (2013.01); *A61K 2039/80* (2018.08)

(56) References Cited

U.S. PATENT DOCUMENTS

| | | | | |
|---|---|---|---|---|
| 5,653,999 | A | 8/1997 | Gaudreault | |
| 6,395,029 | B1 | 5/2002 | Levy | |
| 8,846,026 | B2 | 9/2014 | Plebanski | |
| 10,285,952 | B2 * | 5/2019 | Zhang | A61K 9/5094 |
| 10,383,830 | B2 * | 8/2019 | Zhang | A61K 31/43 |
| 10,588,867 | B2 * | 3/2020 | Zhang | A61K 31/545 |
| 10,610,493 | B2 * | 4/2020 | Zhang | A61K 9/5068 |
| 10,632,070 | B2 * | 4/2020 | Zhang | A61K 31/49 |
| 11,000,593 | B2 * | 5/2021 | Zhang | A61L 27/3604 |
| 11,007,147 | B2 | 5/2021 | Zhang | |
| 11,224,577 | B2 | 1/2022 | Zhang | |
| 11,357,736 | B2 * | 6/2022 | Zhang | A61K 9/5176 |
| 11,359,058 | B2 | 6/2022 | Gao | |
| 11,439,698 | B2 | 9/2022 | Hu | |
| 12,285,472 | B2 * | 4/2025 | Zhang | A61K 9/0014 |
| 12,350,381 | B2 | 7/2025 | Gao et al. | |
| 2004/0110695 | A1 | 6/2004 | Dobbie | |
| 2004/0180094 | A1 | 9/2004 | Joyce | |
| 2005/0118275 | A1 | 6/2005 | O'Hagan | |
| 2006/0292174 | A1 | 12/2006 | de los Rios et al. | |
| 2007/0243137 | A1 | 10/2007 | Hainfeld | |
| 2007/0258889 | A1 | 11/2007 | Douglas et al. | |
| 2009/0214663 | A1 * | 8/2009 | Albrecht | A61K 39/12 435/5 |
| 2010/0021503 | A1 | 1/2010 | Denoel et al. | |
| 2011/0280930 | A1 | 11/2011 | Batista et al. | |
| 2011/0293723 | A1 | 12/2011 | Bratzler | |
| 2013/0336884 | A1 * | 12/2013 | DeSimone | A61K 35/18 424/1.29 |
| 2013/0337066 | A1 | 12/2013 | Zhang et al. | |
| 2016/0136106 | A1 | 5/2016 | Zhang et al. | |
| 2017/0000875 | A1 | 1/2017 | Hu | |
| 2017/0079909 | A1 | 3/2017 | Zhang et al. | |
| 2017/0095510 | A1 | 4/2017 | Lee | |
| 2017/0368160 | A1 | 12/2017 | Hu | |
| 2018/0140558 | A1 | 5/2018 | Zhang | |
| 2018/0153821 | A1 | 6/2018 | Zhang | |
| 2018/0169027 | A1 | 6/2018 | Zhang | |
| 2023/0051094 | A1 | 2/2023 | Gao | |

FOREIGN PATENT DOCUMENTS

| | | | |
|---|---|---|---|
| JP | 2005-525407 | A | 8/2008 |
| WO | 2005020964 | A1 | 3/2005 |
| WO | 2008013952 | A2 | 1/2008 |
| WO | 2008/150276 | A2 | 12/2008 |
| WO | 2011/116219 | A1 | 9/2011 |
| WO | 2012149376 | A2 | 11/2012 |
| WO | 2013052167 | A2 | 4/2013 |
| WO | 2015187502 | A1 | 4/2013 |
| WO | 2015021390 | A2 | 2/2015 |
| WO | 2016109306 | A1 | 7/2016 |

OTHER PUBLICATIONS

Che-Ming J. Hu, Li Zhang, Santosh Aryal, Connie Cheung, Ronnie H. Fang, and Liangfang Zhang. "Erythrocyte membrane-camouflaged polymeric nanoparticles as a biomimetic delivery platform." Proceedings of the National Academy of Sciences, vol. 108, No. 27 ,Jul. 5, 2011, pp. 10980-10985. (Year: 2011).*

Maria A. G. Soler et al. "Interaction of Erythrocytes with Magnetic Nanoparticles." Journal of Nanoscience and Nanotechnology, vol. 7, 2007, pp. 1069-1071. (Year: 2007).*

Yasemin Ataman-Önal et al. "Surfactant-free anionic PLA nanoparticles coated with HIV-1 p24 protein induced enhanced cellular and humoral immune responses in various animal models." Journal of Controlled Release, vol. 112, 2006, pp. 175-185. (Year: 2006).*

Chinese Office Action mailed Feb. 2, 2015.

Jianlin Xu, Experimental Study on Magnetized Technique of Doxorubicin-loaded Erythrocytes, Wanfang Data, pp. 13, 21-22, 35, 52, Oct. 19, 2009.

Hu et al., 2011, "Erthrocyte Membrane-Camouflaged Polymeric Nanoparticles as a Biomimetic Delivery Platform," PNAS, 108(27): 10980-10985.

International Preliminary Report on Patentability for PCT Application No. PCT/US2012/039411, mailed Apr. 3, 2014 (6 pages).

Yoo et al. (Journal of Controlled release (2000), 68, 419-431.

European Search Report for EP Application No. 12838792.5 mailed May 7, 2015 (5 pages).

European Supplementary Search Report for EP Application No. 12838792.5 mailed May 27, 2015 (4 pages).

Moore et al., "Specific Targeting and Delivery of Virus Envelope-Coated Nanoparticle Cargoes into Receptor-Bearing Cells and Subcellular Compartments," NSTI—Nanotech 2007, vol. 2, pp. 370-373.

Response to Office Action for CN Application No. 2012800350485 filed on Jul. 6, 2015 and English version of remarks and claims.

Response as filed on Nov. 24, 2015 with the European Patent Office in response to the European Supplementary Search Report for EP Application No. 12838792.5 mailed May 27, 2015 (9 pages).

Chinese Office Action for CN Application No. 201280035048.5 mailed Nov. 10, 2015 (13 pages).

Taiwanese Office Action for TW Application No. 101119113 mailed Oct. 6, 2015 (15 pages).

Ce et al., "Pharmacokinetics of Morphine Loaded into Erythrocyte in Rabbits," Journal of China Pharmaceutical University, 2006, 37(2):150-152.

Sahoo et al., "Enhanced Antiproliferative Activity of Transferrin-Conjugated Paclitaxel-Loaded Nanoparticles is Mediated via Sustained Intracellular Drug Retention," Molecular Pharmaceutics, 2005, 2(5):373-383.

Response to Taiwanese Office Action for TW Application No. 101119113 filed on Feb. 5, 2016 (56 pages).

Response to Chinese Office Action for CN Application No. 2012800350485 filed on Jan. 25, 2016 (63 pages).

Japanese Office Action for JP Application No. 2014-513590 mailed Feb. 19, 2016 (9 pages).

Taiwanese Office Action for TW Application No. 101119113 mailed Jun. 7, 2016 (13 pages with English translation).

Blum et al., "Pathways of Antigen Processing," Annu. Rev. Immunol., 2013, 31, pp. 443-473.

Boes et al., "Endosomal processing for antigen presentation mediated by CD1 and Class I major histocompatibility complex: roads to display or destruction," Immunology, 2009, 127(2), pp. 163-170.

Cryz, Jr et al., "Effect of Chemical and Heat Inactivation on the Antigenicity and Immunogenicity of Vibrio Cholerae," Infect. Immun., 1982, 38(1), pp. 21-26.

(56) References Cited

OTHER PUBLICATIONS

Greenberg et al., "Phase I dose finding studies of an adjuvanted Clostridium difficile toxoid vaccine," Vaccine, 2012, 30, pp. 2245-2249.
Harush-Frenkel et al., "Targeting of nanoparticles to the clathrin-mediated endocytic pathway," Biochem. Biophys. Res. Commun., 2007, 353, pp. 26-32.
Holmgren et al., "Development of improved cholera vaccine based on subunit toxoid," Nature, 1977, 269, pp. 502-604.
Kitchin, N., "Review of diphtheria, tetanus and pertussis vaccines in clinical development," Expert Rev. Vaccines, 2011, 10(5), pp. 605-615.
Metz et al., "Identification of Formaldehyde-induced Modifications in Proteins: Reactions with Model Peptides," J Biol. Chem., 2004, 279(8), pp. 6235-6243.
Mortimer, E. A. Jr., "Immunization Against Infectious Disease," Science, 1978, 200, pp. 902-907.
Parish et al., "Staphylococcal Infection: Antitoxic Immunity," Br. Med. J., 1960, 1(5175), pp. 743-747.
Petrov et al., "Toxicity and Immunogenicity of Neisseria meningitidis Lipopolysaccharide Incorporated into Liposomes," Infect. Immun. 1992, 60(9), pp. 3897-3903.
Schmitt et al., "Bacterial toxins: friends or foes?," Emerg. Infect. Dis., 1999, 5(2), pp. 224-234.
Matts et al., "Pathways of antigen processing and presentation," Rev. Immunogenel. 1999, 1, pp. 60-74.
Zhang et al., "Size-Dependent Endocytosis of Nanoparticles," Adv. Maler., 2009, 21, pp. 419-424.
International Preliminary Report on Patenlability for PCT/US2014/067688, issued Jun. 7, 2016.
International Search Report and Written Opinion for PCT/US2014/067688, mailed Feb. 4, 2015.
Office Action issued in U.S. Appl. No. 15/100,273, mailed Nov. 18, 2016.
Response to Restriction Requirement issued in U.S. Appl. No. 15/100,273, filed Jan. 18, 2017.
Office Action issued in U.S. Appl. No. 15/100,273, mailed Feb. 17, 2017.
Response to Taiwanese Office Action in TW Application No. 101119113 submitted on Jun. 21, 2018 (8 pages).
Office Action mailed Aug. 13, 2018 for U.S. Appl. No. 15/568,316 (15 pages).
Blain, "Organophosphorus Poisoning (Acute)," Clinical Evidence, 2011, 05:2102 (17 pages).
Hu et al., "A Biomimetic Nanosponge that Absorbs Pore-Forming Toxins", Nature Nanotechnology, 2013, 8:336-340.
European Extended Search Report for EP Application No. 18185536.2 mailed Sep. 30, 2018 (11 pages).
Office Action for U.S. Appl. No. 15/679,096 mailed Jan. 22, 2019 (11 pages).
Final Office Action for U.S. Appl. No. 15/679,096 mailed Sep. 23, 2019 (19 pages).
Response to Non-Final Office Action for U.S. Appl. No. 15/679,096 submitted Jul. 18, 2019 (13 pages).
Bakas et al., "Reversible Adsorption and Nonreversible Insertion of *Escherichia coli* alpha-Hemolysin into Lipid Bilayers," Biophysical Journal, 1996, 71:1889-1876.
Fuji et al., "In vitro Evolution of a alpha-Hemolysin Using a Liposome Display," PNAS, 2013, 110(42): 16796-16801.
Kevin E. Noonan, Patent Docs, https://www.jdsupra.com/legalnews/eli-lilly-co-v-teva-parenteral-32503/accessed Nov. 10, 2022, pp. 1-7 (2022).
Maria A.G. Soler, et al., "Interaction of Erythrocytes with Magnetic Nanoparticles," Journal of Nanoscience and Nanotechnology, vol. 7, 2007. pp. 1069-1071 (2007).
Moghimi, S. et al., "Long-Circulating and Target-Specific Nanoparticles: Theory to Practice." Pharmacol Rev, vol. 53, No. 2, 2001, pp. 283-318, The American Society for Pharmacology and Experimental Therapeutics.
Davis, M. et al., "Nanoparticle therapeutics: an emerging treatment modality for cancer." Nature Reviews/Drug Discovery, 2008, pp. 71-782, vol. 7, Macmillan Publishers Limited.
Peer, D. et al., "Nanocarriers as an emerging platform for cancer therapy." Nature Nanotechnology, 2007, pp. 751-760, vol. 2, Nature Publishing Group.
Yoo, J. et al., "Factors that Control the Circulation Time of Nanoparticles in Blood: Challenges, Solutions and Future Prospects." Current Pharmaceutical Design, 2010, pp. 2298-2307, vol. 16, Bentham Science Publishers Ltd.
Geng, Y. et al., "Shape effects of filaments versus spherical particles in flow and drug delivery." Nature Nanotechnology, 2007, pp. 249-255, vol. 2, Nature Publishing Group.
Alexis, F. et al., "Factors Affecting the Clearance and Biodistribution of Polymeric Nanoparticles." Molecular Pharmaceutics, 2008, pp. 505-515, vol. 5, No. 4.
Knop, K. et al., "Poly(ethylene glycol) in Drug Delivery: Pros and Cons as Well as Potential Alernatives." Angew. Chem. Int. Ed., 2010, pp. 6288-6308, vol. 49, Wiley-VCH Verlag GmbH & Co.
Jiang, S. et al., "Ultralow-Fouling, Functionalizable, and Hydrolyzable Zwitterionic Materials and Their Derivatives for Biological Applications." Adv. Mater., 2010, pp. 920-932, vol. 22, Wiley-VCH Verlag GmbH & Co.
Yang, W. et al., "Functionalizable and ultra stable nanoparticles coated with zwitterionic poly(carboxybetaine) in undiluted blood serum." Biomaterials, 2009, pp. 5617-5621, vol. 30, Elsevier Ltd.
International Search Report and Written Opinion for PCT/US12/039411 mailed Aug. 8, 2013 (7 pages).
Tsai RK, Rodriguez PL, Discher DE (2010) Self inhibition of phagocytosis: the affinity of 'marker of self' CD47 for SIRPalpha dictates potency of inhibition but only at low expression levels. Blood Cells Mol Dis 45:67-74.
Merkel TJ, et al. (2011) Using mechanobiological mimicry of red blood cells to extend circulation times of hydrogel microparticles. Proc Natl Acad Sci U S A 108:586-591.
Desilets J, Lejeune A, Mercer J, Gicquaud C (2001) Nanoerythrosomes, a new derivative of erythrocyte ghost: IV. Fate of reinjected nanoerythrosomes. Anticancer Res 21:1741-1747.
Cheng J, et al. (2007) Formulation of functionalized PLGA-PEG nanoparticles for in vivo targeted drug delivery. Biomaterials 28:869-876.
Tanaka M, Sackmann E (2005) Polymer-supported membranes as models of the cell surface. Nature 437:656-663.
Hochmuth RM, Evans CA, Wiles HC, McCown JT (1983) Mechanical measurement of red cell membrane thickness. Science 220:101-102.
Fang RH, Aryal S, Hu CM, Zhang L (2010) Quick synthesis of lipid-polymer hybrid nanoparticles with low polydispersity using a single-step sonication method. Langmuir 26:16958-16962.
Popielarski SR, Pun SH, Davis ME (2005) A nanoparticle-based model delivery system to guide the rational design of gene delivery to the liver. 1. Synthesis and characterization. Bioconjug Chem 16:1063-1070.
Goutayer M, et al. (2010) Tumor targeting of functionalized lipid nanoparticles: assessment by in vivo fluorescence imaging. Eur J Pharm Biopharm 75:137-147.
Xiao K, et al. (2009) A self-assembling nanoparticle for paclitaxel delivery in ovarian cancer. Biomaterials 30:6006-6016.
Gratton SE, et al. (2007) Nanofabricated particles for engineered drug therapies: a preliminary biodistribution study of PRINT nanoparticles. J Control Release 121:10-18.
Peracchia MT, et al. (1999) Stealth PEGylated polycyanoacrylate nanoparticles for intravenous administration and splenic targeting. J Control Release 60:121-128.
Simberg D, et al. (2007) Biomimetic amplification of nanoparticle homing to tumors. Proc Natl Acad Sci U S A 104:932-936.
Oldenborg PA, et al. (2000) Role of CD47 as a marker of self on red blood cells. Science 288:2051-2054.
Gu F, et al. (2008) Precise engineering of targeted nanoparticles by using self-assembled biointegrated block copolymers. Proc Natl Acad Sci USA 105:2586-2591.

(56) References Cited

OTHER PUBLICATIONS

Avgoustakis K, et al. (2003) Effect of copolymer composition on the physicochemical characteristics, in vitro stability, and biodistribution of PLGA-mPEG nanoparticles. Int J Pharm 259:115-127.
Zhang L. (2010) Lipid-polymer hybrid nanoparticles: synthesis, characterization and applications. Nano LIFE 1:163-173.
Sengupta S, et al. (2005) Temporal targeting of tumor cells and neovasculature with a nanoscale delivery system. Nature 436:568-572.
Valencia PM, et al. (2010) Single-step assembly of homogenous lipid-polymeric and lipid-quantum dot nanoparticles enabled by microfluidic rapid mixing. ACS Nano 4:1671-1679.
Liu J, Stace-Naughton A, Jiang X, Brinker CJ (2009) Porous nanoparticle supported lipid bilayers (protocells) as delivery vehicles. J Am Chem Soc 131:1354-1355.
Van Schooneveld MM, et al. (2010) Imaging and quantifying the morphology of an organic-inorganic nanoparticle at the sub-nanometre level. Nat Nanotechnol 5:538-544.
Dodge JT, Mitchell C, Hanahan DJ (1963) The preparation and chemical characteristics of hemoglobin-free ghosts of human erythrocytes. Arch Biochem Biophys 100:119-130.
Zhang L, et al. (2008) Self-assembled lipid-polymer hybrid nanoparticles: A robust drug delivery platform. ACS Nano 2:1696-1702.
Waugh RE, Sarelius IH (1996) Effects of lost surface area on red blood cells and red blood cell survival in mice. Am J Physiol 271:C1847-1852.
Arnold MM, Gorman EM, Schieber LJ, Munson EJ, Berkland C (2007) NanoCipro encapsulation in monodisperse large porous PLGA microparticles. J Control Release 121:100-109.
Jacobs RL, Alling DW, Cantrell WF (1963) An evaluation of antimalarial combinations against plasmodium berghei in the mouse. J Parasitol 49:920-925.
Lund, R.; Leth-Larsen, R.; Jensen, O. N.; Ditzel, H. J., Efficient isolation and quantitative proteomic analysis of cancer cell plasma membrane proteins for identification of metastasis-associated cell surface markers. J Proteome Res 2009, 8 (6), 3078-3090.
Graham, J. M., Isolation of membranes from tissue culture cells. Methods Mol Biol 1993, 19, 97-108.
Vayro, S.; Kemp, R.; Beechey, R. B.; Shirazi-Beechey, S., Preparation and characterization of basolateral plasma-membrane vesicles from sheep parotid glands. Mechanisms of phosphate and D-glucose transport. Biochem J 1991, 279 ( Pt 3), 843-848.
Navas, P.; Nowack, D. D.; Morre, D. J., Isolation of purified plasma membranes from cultured cells and hepatomas by two-phase partition and preparative free-flow electrophoresis. Cancer Res 1989, 49 (8), 2147-2156.
Henon, M.; Bedouin, A.; Polonovski, J., [Isolation, identification and characterization of a plasma membrane preparation of guinea pig macrophages]. C R Acad Sci Hebd Seances Acad Sci D 1977, 285 (1), 121-122.
Boone, C. W.; Ford, L. E.; Bond, H. E.; Stuart, D. C.; Lorenz, D., Isolation of plasma membrane fragments from HeLa cells. J Cell Biol 1969, 41 (2), 378-392.
Petros RA, DeSimone JM. Strategies in the design of nanoparticles for therapeutic applications. Nat. Rev. Drug Discov. 9(8), 615-627 (2010).
Farokhzad OC, Langer R. Impact of Nanotechnology on Drug Delivery. ACS Nano 3(1), 16-20 (2009).
J. Chalmeau, N. Monina, J. Shin, C. Vieu, V. Noireaux, alpha-Hemolysin pore formation into a supported phospholipid bilayer using cell-free expression. Biochim Biophys Acta 1808, 271 (Jan. 2011).
M. Moorjani et al., Nanoerythrosomes, a new derivative of erythrocyte ghost II: identification of the mechanism of action. Anticancer Res 16, 2831 (Sep.-Oct. 1996).
S. Vandana, M. Raje, M. V. Krishnasastry, The role of the amino terminus in the kinetics and assembly of alpha-hemolysin of *Staphylococcus aureus*. J Biol Chem 272, 24858 (Oct. 3, 1997).
A. Valeva et al., Membrane Insertion of the Heptameric Staphylococcal a-Toxin Pore. J Biol Chem 276, 14835-14841 (May 4, 2001).
Eaton M., "Chemical Modification of Purified Diphtheria Toxin." The Journal of Immunology. 1937 (33): 419-436.
International Search Report and Written Opinion for PCT/US14/67688 mailed Nov. 26, 2014 (198 pages).
Aryal, S. et al., "Polymeric Nanoparticles with Precise Ratiometric Control over Drug Loading for Combination Therapy." Mol. Pharmaceutics, 2011, vol. 8, pp. 1401-1407, American Chemical Society.
Tong R, Cheng J. Ring-opening polymerization-mediated controlled formulation of polylactide-drug nanoparticles. J. Am. Chem. Soc. 131(13), 4744-4754 (2009).
Aryal S, Hu CM, Zhang L. Polymer—cisplatin conjugate nanoparticles for acid-responsive drug delivery. ACS Nano 4 (1), 251-258 (2010).
Tong R, Cheng J. Controlled Synthesis of Camptothecin-Polylactide Conjugates and Nanoconjugates. Bioconjug. Chem. 21(1), 111-121 (2010).
Gao W, Chan JM, Farokhzad OC. pH-Responsive Nanoparticles for Drug Delivery. Mol. Pharm. 7(6), 1913-1920 (2010).
Gu F, Zhang L, Teply BA et al. Precise engineering of targeted nanoparticles by using self-assembled biointegrated block copolymers. Proc. Natl. Acad. Sci. USA 105(7), 2586-2591 (2008).
Takae S, Miyata K, Oba M et al. PEG-detachable polyplex micelles based on disulfide-linked block catiomers as bioresponsive nonviral gene vectors. J. Am. Chem. Soc. 130(18), 6001-6009 (2008).
Pornpattananangkul D, Zhang L, Olson S et al. Bacterial Toxin-Triggered Drug Release from Gold Nanoparticle-Stabilized Liposomes for the Treatment of Bacterial Infection. J. Am. Chem. Soc. 133(11), 4132-4139 (2011).
Avgoustakis K, Beletsi A, Panagi Z, Klepetsanis P, Karydas AG, Ithakissios DS. PLGA-mPEG nanoparticles of cisplatin: in vitro nanoparticle degradation, in vitro drug release and in Vivo drug residence in blood properties. J. Control. Release 79(1-3), 123-135 (2002).
Li J, Jiang G, Ding F. The effect of pH on the polymer degradation and drug release from PLGA-mPEG microparticles. J. Appl. Polym. Sci. 109(1), 475-482 (2008).
Higuchi T. Rate of release of medicaments from ointment bases containing drugs in suspension. J. Pharm. Sci. 50, 874-875 (1961).
Siepmann J, Peppas NA. Higuchi equation: derivation, applications, use and misuse. Int. J. Pharm. 418(1), 6-12 (2011).
Budhian A, Siegel SJ, Winey KI. Controlling the in vitro release profiles for a system of haloperidol-loaded PLGA nanoparticles. Int. J. Pharm. 346(1-2), 151-159 (2008).
Pitt CG, Schindler A. The kinetics of drug cleavage and release from matrices containing covalent polymer-drug conjugates. J. Control. Release 33(3), 391-395 (1995).
Lowenberg B, Ossenkoppele GJ, van Putten W et al. High-Dose Daunorubicin in Older Patients with Acute Myeloid Leukemia. New Engl. J. Med. 361(13), 1235-1248 (2009).
Hu C-MJ, Zhang L. Therapeutic Nanoparticles to Combat Cancer Drug Resistance. Curr. Drug Metab. 10(8), 836-841 (2009).
Huwyler J, Cerletti A, Fricker G, Eberle AN, Drewe J. By-passing of P-glycoprotein using immunoliposomes. J. Drug Target. 10(1), 73-79 (2002).
Rapoport N, Marin A, Luo Y, Prestwich GD, Muniruzzaman M. Intracellular uptake and trafficking of pluronic micelles in drug-sensitive and MDR cells: Effect on the intracellular drug localization. J. Pharm. Sci. 91(1), 157-170 (2002).
Sahoo SK, Labhasetwar V. Enhanced anti proliferative activity of transferrin-conjugated paclitaxel-loaded nanoparticles is mediated via sustained intracellular drug retention. Mol. Pharm. 2(5), 373-383 (2005).
Cho, Nam-Hyuk et al. "A Multifunctional Core-Shell Nanoparticle for Dendritic Cell-Based Cancer Immunotherapy." Nature Nanotechnology: 6, 675-82 (2011).
Li, Haiyan et al. "Alpha-Alumina Nanoparticles Induce Efficient Autophagy-Dependent Cross-Presentation and Potent Antitumour Response." Nature Nanotechnology 6, 645-650 (2011).
Moon, James J et al. "Interbilayer-Crosslinked Multilamellar Vesicles as Synthetic Vaccines for Potent Humoral and Cellular Immune Responses." Nature Materials 10.3 (2011): 243-251.

(56) References Cited

OTHER PUBLICATIONS

Tongchusak, S et al. "Induction of Anti-Tumor Cytotoxic T Cell Responses Through PLGA-Nanoparticle Mediated Antigen Delivery." Biomaterials (2011), 32(14):3666-78.

A. E. Clatworthy, E. Pierson, D. T. Hung, Targeting virulence: a new paradigm for antimicrobial therapy. Nat Chem Biol 3, 541 (Sep. 2007).

D. G. Beghini et al., Anti-sera raised in rabbits against crotoxin and phospholipase A2 from Crotalus durissus cascavella venom neutralize the neurotoxicity of the venom and crotoxin. Toxicon 44, 141 (Aug. 2004).

Z. Chen et al., Potent neutralization of anthrax edema toxin by a humanized monoclonal antibody that competes with calmodulin for edema factor binding. Proc Natl Acad Sci U S A 106, 13487 (Aug. 11, 2009).

W. W. Kum, A. W. Chow, Inhibition of staphylococcal enterotoxin A-induced superantigenic and lethal activities by a monoclonal antibody to toxic shock syndrome toxin-1. J Infect Dis 183, 1739 (Jun. 15, 2001).

C. C. McCormick, A. R. Caballero, C. L. Balzli, A. Tang, R. J. O'Callaghan, Chemical inhibition of alpha-toxin, a key corneal virulence factor of *Staphylococcus aureus*. Invest Ophthalmol Vis Sci 50, 2848 (Jun. 2009).

D. T. Hung, E. A. Shakhnovich, E. Pierson, J. J. Mekalanos, Small-molecule inhibitor of Vibrio cholerae virulence and intestinal colonization. Science 310, 670 (Oct. 28, 2005).

Y. Hoshino et al., The rational design of a synthetic polymer nanoparticle that neutralizes a toxic peptide in vivo. Proc Natl Acad Sci U S A 109, 33 (Jan. 3, 2012).

Y. Hoshino et al., Recognition, neutralization, and clearance of target peptides in the bloodstream of living mice by molecularly imprinted polymer nanoparticles: a plastic antibody. J Am Chem Soc 132, 6644 (May 19, 2010).

R. J. Gilbert, Pore-forming toxins. Cell Mol Life Sci 59, 832 (May 2002).

C. J. Rosado et al., The MACPF/CDC family of pore-forming toxins. Cell Microbiol 10, 1765 (Sep. 2008).

J. Bubeck Wardenburg, O. Schneewind, Vaccine protection against Staphylococcus aureus pneumonia. J Exp Med 205, 287 (Feb. 18, 2008).

M. Shoham, Antivirulence agents against MRSA. Future Med Chem 3, 775 (May 2011).

P. O'Hanley, G. Lalonde, G. Ji, Alpha-hemolysin contributes to the pathogenicity of piliated digalactoside-binding *Escherichia coli* in the kidney: efficacy of an alpha-hemolysin vaccine in preventing renal injury in the BALB/c mouse model of pyelonephritis. Infect Immun 59, 1153 (Mar. 1991).

B. T. Edelson, E. R. Unanue, Intracellular antibody neutralizes Listeria growth. Immunity 14, 503 (May 2001).

B. T. Edelson, P. Cossart, E. R. Unanue, Cutting edge: paradigm revisited: antibody provides resistance to Listeria infection. J Immunol 163, 4087 (Oct. 15, 1999).

A. Nakouzi, J. Rivera, R. F. Rest, A. Casadevall, Passive administration of monoclonal antibodies to anthrolysin O prolong survival in mice lethally infected with Bacillus anthracis. BMC Microbiol 8, 159 (2008).

J. E. Alexander et al., Immunization of mice with pneumolysin toxoid confers a significant degree of protection against at least nine serotypes of *Streptococcus pneumoniae*. Infect Immun 62, 5683 (Dec. 1994).

L. A. Kirkham et al., Construction and immunological characterization of a novel nontoxic protective pneumolysin mutant for use in future pneumococcal vaccines. Infect Immun 74, 586 (Jan. 2006).

I. Andreeva-Kovalevskaya Zh, A. S. Solonin, E. V. Sineva, V. I. Ternovsky, Pore-forming proteins and adaptation of living organisms to environmental conditions. Biochemistry (Mosc) 73, 1473 (Dec. 2008).

G. Ma, Q. Cheng, Vesicular polydiacetylene sensor for colorimetric signaling of bacterial pore-forming toxin. Langmuir 21, 6123 (Jul. 5, 2005).

D. Pornpattananangkul et al., Bacterial toxin-triggered drug release from gold nanoparticle-stabilized liposomes for the treatment of bacterial infection. J Am Chem Soc 133, 4132 (Mar. 23, 2011).

D. Branton et al., The potential and challenges of nanopore sequencing. Nat Biotechnol 26, 1146 (Oct. 2008).

Goshi K, Cluff L, Johnson J. "Studies on the Pathogenesis of Staphylococcal Infection." The Journal of Experimental Medicine. 1961, 113(2): 259-270.

Ragle, B.E. et al. "Anti-Alpha-Hemolysin Monoclonal Antibodies Mediate Protection against *Staphylococcus aureus* Pneumonia." Infection and Immunity. 2009, 77(7):2712-2718.

Wardenburg B, Schneewind O., "Vaccine protection against *Staphylococcus aureus* pneumonia." The Journal of Experimental Medicine. 2008, 205(2): 287-294.

A. S. Klainer et al., Staphylococcal Alpha-Hemolysin: Detection on the Erythrocyte Membrane by Immunofluorescence. Science, vol. 145, No. 3633, pp. 714-715 (Aug. 14, 1964).

* cited by examiner

MEMBRANE ENCAPSULATED NANOPARTICLES AND METHOD OF USE

CROSS-REFERENCE TO RELATED APPLICATIONS

This application is a divisional application of U.S. application Ser. No. 13/827,906 filed Mar. 14, 2023 which is a continuation-in-part of PCT Application No. PCT/US2012/039411 filed May 24, 2012 which claims priority to U.S. Provisional Application Ser. No. 61/492,626, filed Jun. 2, 2011, the entire contents of which are incorporated by reference herewith.

STATEMENT REGARDING FEDERALLY SPONSORED RESEARCH

This invention was made with government support under CA119335 awarded by the National Institutes of Health, and under CMMI1031239 awarded by the Health National Science Foundation. The government has certain rights in the invention.

FIELD OF THE INVENTION

The present invention relates to methods and compositions for delivery of synthetic nanoparticle materials, including pharmaceutically active agents, encapsulated with cellular membranes.

BACKGROUND OF THE INVENTION

Long-circulating polymeric nanoparticles have significant clinical impact as they promise sustained systemic delivery and better targeting through both passive and active mechanisms (1-3). Different approaches including modifications on particle size, surface, shape, and flexibility have been explored to extend particle residence time in vivo (4-6). The current gold standard for nanoparticle stealth coating is polyethylene glycol (PEG). The adoption of PEG as a stealth moiety on nanoparticle surface has led to great success with several clinical products (2, 3), but recent observation of anti-PEG immunological response has triggered the interest of further investigation on its biological relevance (7). Synthetic zwitterionic materials such as poly(carboxybetaine) and poly(sulfobetaine) have been proposed as alternatives to PEG because of their strong hydration that is highly resistant to nonspecific protein adsorption (8, 9). In addition, recent advances in molecular and cellular biology have inspired scientists and nanotechnologists to model nanocarriers after red blood cells (RBCs), which are nature's long-circulating delivery vehicles. Properties of RBCs such as their structure and surface proteins have been taken as design cues to devise the next-generation delivery platforms (10-12).

While significant efforts have been devoted to bridging the gap between synthetic nanomaterials and biological entities, an RBC-mimicking delivery vehicle has remained elusive to biomedical researchers. One major challenge lies in the difficulty in functionalizing nanoparticles with the complex surface chemistry of a biological cell. Despite the recent great progress in reducing macrophage engulfment of polystyrene beads following their conjugation with an immunosuppressive RBC membrane protein, CD47 (11), current chemistry-based bioconjugation techniques often lead to protein denaturation. In addition, these bottom-up approaches are largely inadequate in duplicating a complex protein makeup on a nanoscale substrate.

Therefore, what is needed are improved methods and compositions for delivery of synthetic nanoparticle materials. The present invention addresses these and other related needs in the art.

SUMMARY OF THE INVENTION

The present invention provides novel nanoparticles, and methods of using and making thereof. More specifically, the inventive nanoparticle comprises a) an inner core comprising a non-cellular material; and b) an outer surface comprising a cellular membrane derived from a cell or a membrane derived from a virus. In certain embodiments, the inner core of the inventive nanoparticle comprises a biocompatible and/or a synthetic material including but not limited to, poly(lactic-co-glycolic acid), polylactic acid, polyglycolic acid, polycaprolactone, polylysine, polyglutamic acid, and any other suitable synthetic material or the like.

In certain embodiments, the outer surface of the inventive nanoparticle comprises cellular membrane comprising plasma membrane or an intracellular membrane derived from a unicellular (e.g. a bacterium or fungus) or multicellular organism (e.g., a plant, an animal, a non-human mammal, vertebrate, or a human). In certain embodiments, the outer surface of the inventive nanoparticle comprises a naturally occurring cellular or viral membrane and/or further comprises a synthetic membrane.

In certain embodiments, the cellular membrane of the outer surface of the inventive nanoparticle is derived from a blood cell (e.g., red blood cell (RBC), white blood cell (WBC), or platelet). In other embodiments, the cellular membrane of the outer surface is derived from an immune cell (e.g., macrophage, monocyte, B-cell, or T-cell), a tumor or cancer cell, and other cells, such as an epithelial cell, an endothelial cell, or a neural cell. In other embodiments, the cellular membrane of the outer surface is derived from a non-terminally differentiated cell, such as a stem cell, including a hematopoietic stem cell, a bone marrow stem cell, a mesenchymal stem cell, a cardiac stem cell, a neural stem cell. The non-terminally differentiated cell can be isolated in a pluripotent state from tissue or induced to become pluripotent. In yet other embodiments, the cellular membrane is derived from a cell component or cell organelle including, but not limited to, an exosome, a secretory vesicle, a synaptic vesicle, an endoplasmic reticulum (ER), a Golgi apparatus, a mitochondrion, a vacuole or a nucleus.

In certain embodiments, the present invention further provides that the inventive nanoparticle comprises a releasable cargo that can be located in any place inside or on the surface of the nanoparticle. A trigger for releasing the releasable cargo from the inventive nanoparticle includes, but is not limited to, contact between the nanoparticle and a target cell, tissue, organ or subject, or a change of an environmental parameter, such as the pH, ionic condition, temperature, pressure, and other physical or chemical changes, surrounding the nanoparticle. In certain embodiments, the releasable cargo comprises one or more therapeutic agent, prophylactic agent, diagnostic or marker agent, prognostic agent, e.g., an imaging marker, or a combination thereof. In yet certain other embodiments, the releasable cargo is a metallic particle, a polymeric particle, a dendrimer particle, or an inorganic particle.

The present nanoparticle can have any suitable shape. For example, the present nanoparticle and/or its inner core can have a shape of sphere, square, rectangle, triangle, circular disc, cube-like shape, cube, rectangular parallelepiped (cuboid), cone, cylinder, prism, pyramid, right-angled circular cylinder and other regular or irregular shape. The present nanoparticle can have any suitable size.

The present invention further provides that in certain embodiments the inventive nanoparticle has a diameter from about 10 nm to about 10 μm. In certain embodiments, the diameter of the invention nanoparticle is about 50 nm to about 500 nm. In other embodiments, the diameter of the nanoparticle can be about 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 μm, 2 μm, 3 μm, 4 μm, 5 μm, 6 μm, 7 μm, 8 μm, 9 μm, and 10 μm, or any suitable sub-ranges within the about 10 nm to about 10 μm range, e.g., a diameter from about 50 nm to about 150 nm. In certain embodiments, the inner core supports the outer surface.

The present invention further provides that the invention nanoparticle substantially lacks constituents of the cell from which the cellular membrane is derived or constituents of the virus from which the viral membrane is derived. For example, the present nanoparticle can lack, in terms of types and/or quantities, at least 10%, 20%, 30%, 40%, 50%, 60%, 70%, 80%, 90%, 95%, 96%, 97%, 98%, 99% or 100% of the constituents of the cell from which the cellular membrane is derived or constituents of the virus from which the viral membrane is derived.

In yet certain other embodiments, the nanoparticle of the present invention substantially maintains natural structural integrity or activity of the cellular membrane, the membrane derived from a virus or the constituents of the cellular membrane or viral membrane. The structural integrity of the cellular membrane includes primary, secondary, tertiary or quaternary structure of the cellular membrane, the membrane derived from a virus or the constituents of the cellular membrane or viral membrane, and the activity of the cellular membrane includes, but is not limited to, binding activity, receptor activity, signaling pathway activity, and any other activities a normal naturally occurring cellular membrane, the membrane derived from a virus or the constituents of the cellular membrane or viral membrane, would have. In certain embodiments, the nanoparticle of the present invention is biocompatible and/or biodegradable. For example, the present nanoparticle can maintain, in terms of types and/or quantities, at least 10%, 20%, 30%, 40%, 50%, 60%, 70%, 80%, 90%, 95%, 96%, 97%, 98%, 99% or 100% of the natural structural integrity or activity of the cellular membrane, the membrane derived from a virus or the constituents of the cellular membrane or viral membrane.

In certain embodiments, the nanoparticle of the present invention comprises the cellular plasma membrane derived from a red blood cell and an inner core comprising poly (lactic-co-glycolic acid) (PLGA), wherein the nanoparticle substantially lacks hemoglobin. For example, the present nanoparticle can lack, in terms of types and/or quantities, at least 10%, 20%, 30%, 40%, 50%, 60%, 70%, 80%, 90%, 95%, 96%, 97%, 98%, 99% or 100% of the hemoglobin of the red blood cell from which the plasma membrane is derived.

Such inventive nanoparticle has a half-life in blood circulation in vivo at least about 2-5 times of a half-life of a polyethylene glycol (PEG)-coated, comparable nanoparticle. In certain embodiments, such inventive nanoparticle has a half-life in blood circulation in vivo for at least about 5 to about 40 hours or longer.

In certain embodiments, the invention nanoparticle substantially lacks immunogenicity to a species or subject from which the cellular membrane is derived. For example, the present nanoparticle can lack, in terms of types and/or quantities, at least 10%, 20%, 30%, 40%, 50%, 60%, 70%, 80%, 90%, 95%, 96%, 97%, 98%, 99% or 100% of the immunogenicity to a species or subject from which the cellular membrane is derived.

The present invention further provides a medicament delivery system, and/or a pharmaceutical composition comprising the inventive nanoparticle. In certain embodiments, the medicament delivery system and/or the pharmaceutical composition of the present invention further comprises one or more additional active ingredient and/or a medically or pharmaceutically acceptable carrier or excipient, that can be administered along with or in combination with the nanoparticle of the present invention.

The present invention further provides a method for treating and/or preventing a disease or condition in a subject in need using the inventive nanoparticles, the medicament delivery system, or the pharmaceutical composition comprising the same. In certain embodiments, the cellular membrane of the nanoparticle used for the inventive method is derived from a cell of the same species of the subject or is derived from a cell of the subject. In certain embodiments, the cellular membrane of the nanoparticle used for the inventive method is derived from a red blood cell of the same species of the subject and the red blood cell has the same blood type of the subject. In certain embodiments, the nanoparticle, the medicament delivery system, or the pharmaceutical composition is administered via any suitable administration route. For example, the nanoparticle, the medicament delivery system, or the pharmaceutical composition can be administered via an oral, nasal, inhalational, parental, intravenous, intraperitoneal, subcutaneous, intramuscular, intradermal, topical, or rectal route.

In other embodiments, the nanoparticle is administered via a medicament delivery system. In yet other embodiments, the inventive method further comprises administering another active ingredient, or a pharmaceutically acceptable carrier or excipient, to the subject in need. The inventive method further provides that the nanoparticle of the present invention can be administered systemically or to a target site of the subject in need. Use of an effective amount of nanoparticles of the present invention for the manufacture of a medicament for treating or preventing a disease or condition in a subject in need is also provided.

Furthermore, the present invention provides an immunogenic composition comprising an effective amount of nanoparticle that comprises an inner core comprising a non-cellular material, and an outer surface comprising a cellular or plasma membrane derived from a cell and an antigen or a hapten. A vaccine comprising the immunogenic composition of the present invention is also provided. The present invention further provides a method of use of the invention immunogenic composition for eliciting an immune response to the antigen or hapten in a subject in need of such elicitation, and method of use of the invention vaccine comprising the immunogenic composition for protecting a subject against the antigen or hapten. In certain embodiments, the immune response is T-cell or B-cell mediated immune response. Use of an effective amount of the nanoparticle of the present invention for the manufacture of the immunogenic composition against an antigen or hapten, and use of an effective amount of the immunogenic composition for the manufacture of a vaccine for protecting a subject against the antigen or hapten, are also provided.

The present invention further provides a method for making the nanoparticle of the invention, comprising mixing a nanoparticle inner core comprising a non-cellular material with a cellular membrane derived from a cell or a membrane derived from a virus while exerting exogenous energy to form the nanoparticle. In certain embodiments, the exogenous energy is a mechanical energy, e.g., a mechanical energy exerted by extrusion. In other embodiments, the exogenous energy is an acoustical energy, e.g., an acoustical energy exerted by sonication. In yet other embodiment, the exogenous energy is a thermal energy, e.g., a thermal energy exerted by heating. In yet other embodiments, the inventive method further comprises mixing a nanoparticle inner core comprising non-cellular material with a naturally occurring cellular membrane derived from a cell or a naturally occurring membrane derived from a virus with a synthetic membrane while exerting exogenous energy to form the nanoparticle comprising the inner core and an outer surface comprising the cellular membrane or viral membrane and the synthetic membrane.

The present invention further provides a neoplasm specific immunogenic composition comprising an effective amount of the nanoparticle that comprises an inner core comprising a non-cellular material, and an outer surface comprising a cellular membrane derived from a neoplasm cell, wherein the cellular membrane substantially retains its structurally integrity for eliciting an immune response to the neoplasm cell. For example, the present nanoparticle can maintain, in terms of types and/or quantities, at least 10%, 20%, 30%, 40%, 50%, 60%, 70%, 80%, 90%, 95%, 96%, 97%, 98%, 99% or 100% of its structurally integrity for eliciting an immune response to the neoplasm cell.

In certain embodiments, the inner core supports the outer surface of such nanoparticles. In certain embodiments, the inner core of such nanoparticles comprises PLGA and the outer surface comprises a plasma membrane derived from a neoplasm cell. In other embodiments, the outer surface of such nanoparticles comprises naturally occurring cellular or viral membrane and further comprises a synthetic membrane.

The nanoparticle contained in the inventive neoplasm specific immunogenic composition substantially lacks constituents of the neoplasm cell from which the cellular membrane is derived. For example, the present nanoparticle can lack, in terms of types and/or quantities, at least 10%, 20%, 30%, 40%, 50%, 60%, 70%, 80%, 90%, 95%, 96%, 97%, 98%, 99% or 100% the constituents of the neoplasm cell from which the cellular membrane is derived.

In certain embodiments, the nanoparticle in the invention neoplasm specific immunogenic composition has a diameter from about 10 nm to about 10 μm. In certain embodiments, such nanoparticle has a diameter from about 50 nm to about 500 nm. In certain embodiments, the nanoparticle in the inventive neoplasm specific immunogenic composition further comprises another active ingredient, or a releasable cargo. In yet other embodiments, the inventive neoplasm specific immunogenic composition further comprises an immunogenic adjuvant or an immunopotentiator.

The present invention further provides a vaccine comprising the neoplasm specific immunogenic composition. Methods for treating or preventing a neoplasm in subject in need using the invention neoplasm specific immunogenic composition or the vaccine are also provided. The present invention further provides the use of an effective amount of the nanoparticle of the present invention for the manufacture of a cancer or neoplasm specific immunogenic composition or vaccine for treating or preventing a subject against a neoplasm.

The present invention further provides a pharmaceutical composition comprising the nanoparticle of the invention for treating or preventing a disease or condition associated with a cell membrane inserting toxin, wherein the nanoparticle contained in the pharmaceutical composition comprises an inner core comprising a non-cellular material and an outer surface comprising a cellular or plasma membrane derived from a target cell, e.g., a red blood cell. In certain embodiments, the toxin inserted into the cellular or plasma membrane of the target cells is part of the natural pathological mechanism, or the cellular or plasma membrane in the outer surface of the nanoparticle substantially retains the toxin. In certain embodiments, the toxin is a bacterial (e.g., *S. aureus*), plant, fungal, or an animal toxin.

In certain embodiments, the inner core supports the outer surface, and the cellular membrane in the outer surface of the nanoparticle substantially retains its structural integrity for substantially retaining the toxin. In yet certain other embodiments, the outer surface of the nanoparticle comprises a naturally occurring cellular or viral membrane and further comprises a synthetic membrane or synthetic or naturally occurring components added to the cellular membrane. In yet certain other embodiments, the nanoparticle contained in such pharmaceutical composition is biocompatible, biodegradable, or comprises a synthetic material. In yet certain other embodiments, the pharmaceutical composition of the present invention further comprises another active ingredient or a pharmaceutically acceptable carrier or excipient.

Methods for treating or preventing a disease or condition associated with a cell membrane inserting toxin using the nanoparticle of the present invention, as well as a pharmaceutical composition comprising such nanoparticles, are also provided. The present invention further provides the use of an effective amount of the pharmaceutical composition comprising the nanoparticle for the manufacture of a medicament for treating or preventing a disease or condition associated with a cell membrane inserting toxin in subject in need.

Furthermore, the present invention provides an immunogenic composition comprising an effective amount of nanoparticle that comprises an inner core comprising a non-cellular material, and an outer surface comprising a cellular or plasma membrane derived from a cell and a cell membrane inserting toxin. A vaccine comprising the immunogenic composition of the present invention is also provided. The present invention further provides a method of use of the inventive immunogenic composition for eliciting an immune response to a cell membrane inserting toxin in a subject in need of such elicitation, and method of use of the inventive vaccine comprising the immunogenic composition for protecting a subject against the cell membrane inserting toxin. In certain embodiments, the immune response is T-cell or B-cell mediated immune response. Use of an effective amount of the nanoparticle of the present invention for the manufacture of the immunogenic composition against a cell membrane inserting toxin, and use of an effective amount of the immunogenic composition for the manufacture of a vaccine for protecting a subject against cell membrane inserting toxin, are also provided.

The present invention contemplates treatments, prevention, diagnosis and/or prognosis of any diseases, disorders, or physiological or pathological conditions, including, but not limited to, an infectious disease, a parasitic disease, a neoplasm, a disease of the blood and blood-forming organs, a disorder involving the immune mechanism, endocrine, nutritional and metabolic diseases, a mental and behavioral disorder, a disease of the nervous system, a disease of the eye and adnexam, a disease of the ear and mastoid process, a disease of the circulatory system, a disease of the respiratory system, a disease of the digestive system, a disease of the skin and subcutaneous tissue, a disease of the musculoskeletal system and connective tissue, a disease of the genitourinary system, pregnancy, childbirth and the puerperium, a condition originating in the perinatal period, a congenital malformation, a deformation, a chromosomal abnormality, an injury, a poisoning, a consequence of external causes, and an external cause of morbidity and mortality.

In some embodiments, the present nanoparticles, medicament delivery systems, pharmaceutical compositions and methods can be used to treat or prevent the exemplary cancers and tumors listed in Table 1, to deliver the exemplary cancer medications listed in Table 2, to treat or prevent the exemplary ocular diseases or conditions listed in Table 3, to deliver the exemplary ocular medications listed in Table 4, to treat or prevent the exemplary diseases or conditions affecting the lungs listed in Table 5, to deliver the exemplary lungs/respiratory disease medications listed in Table 6, to treat or prevent the exemplary diseases or conditions affecting the heart listed in Table 7, or to deliver the exemplary heart medications listed in Table 8. In some embodiments, the present nanoparticles, medicament delivery systems, pharmaceutical compositions and methods can be used to treat or prevent the exemplary conditions listed in Table 9. Tables 1-9 are attached herewith at the end of the instant specification.

In some embodiments, the present nanoparticles, medicament delivery systems, pharmaceutical compositions and methods, can be used to deliver the exemplary medications listed in the Orange Book: Approved Drug Products with Therapeutic Equivalence Evaluations (Current through March 2012) published by the U.S. Food and Drug Administration, the exemplary medications listed in The Merck Index (a U.S. publication, the printed 14th Edition, Whitehouse Station, N.J., USA) and its online version (The Merck Index Online$^{SM}$, Last Loaded on Web: Tuesday, May 1, 2012), and the exemplary medications listed in Biologics Products & Establishments published by the U.S. Food and Drug Administration, and can be used to treat or prevent the corresponding diseases and disorders.

BRIEF DESCRIPTION OF THE DRAWINGS

Those of skill in the art will understand that the drawings, described below, are for illustrative purposes only. The drawings are not intended to limit the scope of the present teachings in any way.

FIG. 2. Structural characterization of the RBC membrane-coated PLGA nanoparticles.

FIG. 3. Membrane protein retention, particle stability in serum, and the in vivo circulation time of the RBC membrane-coated nanoparticles (NPs).

FIG. 4. Biodistributions of the RBC membrane-coated polymeric nanoparticles. Fluorescently labeled nanoparticles were injected intravenously into the mice. At each time points (24, 48, and 72 hour respectively), the organs from a randomly grouped subset of mice were collected, homogenized and quantified for fluorescence.

FIG. 11. In vitro stability test of DOX-loaded RBCm-cloaked NPs. DOX was loaded into the NPs through either chemical conjugation or physical encapsulation.

FIG. 19C 200 μg of the nanoformulations mixed with 3 μg of α-toxin was filtered and analyzed by SDS-PAGE for toxin absorption. 3 μg of unfiltered α-toxin was prepared as a reference.

FIG. 32. 100 nm polymeric nanoparticles were coated with platelet membranes.

FIG. 39. Source of bacterial membrane.

FIG. 41. Coating of polymeric nanoparticles with bacterial membrane derived from *H. pylori*.

DETAILED DESCRIPTION OF THE INVENTION

Figure 1:
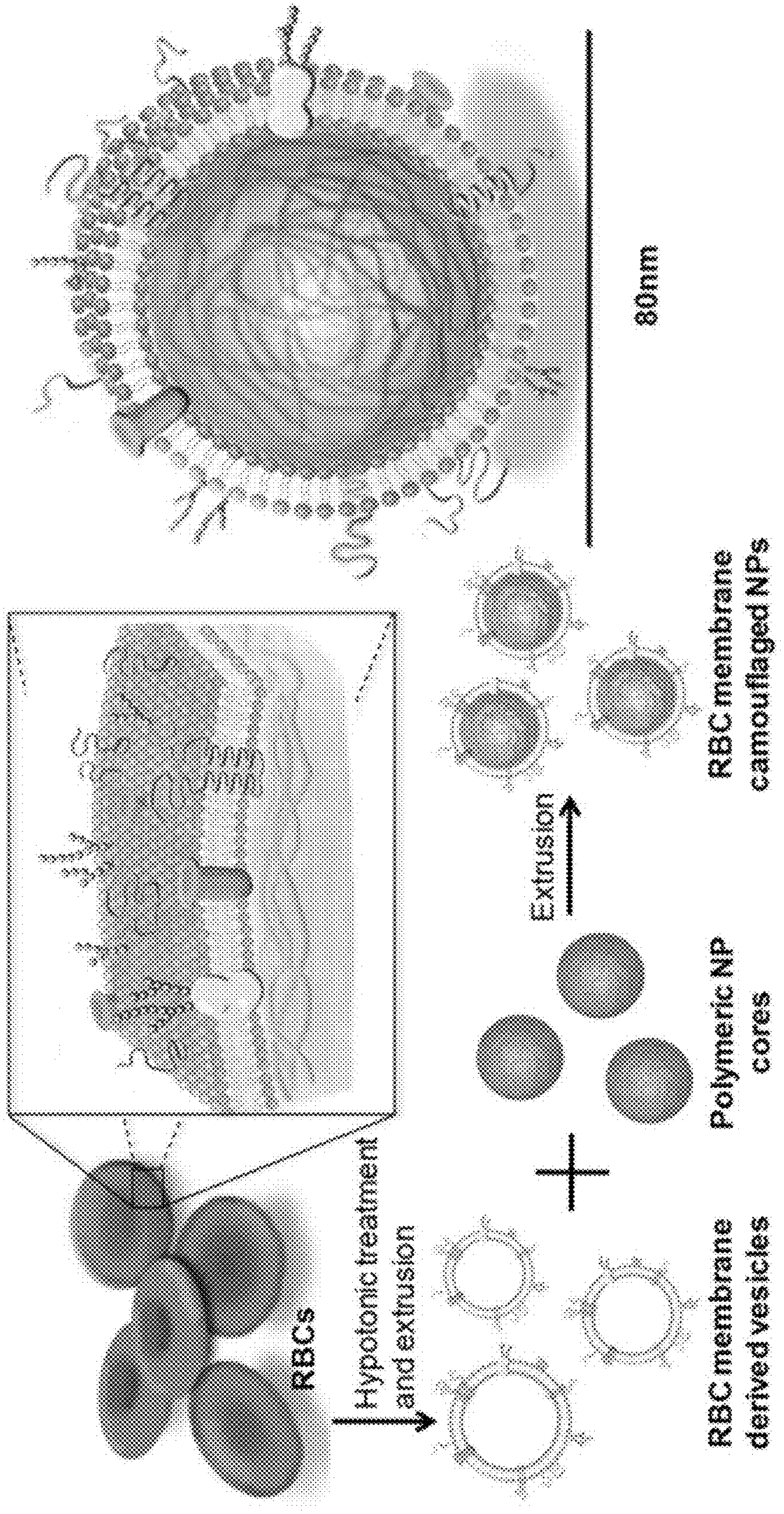
FIG. 1. Schematics of the preparation process of the RBC membrane-coated PLGA nanoparticles (NPs).

The practice of the present invention will employ, unless otherwise indicated, conventional techniques of nanotechnology, nano-engineering, molecular biology (including recombinant techniques), microbiology, cell biology, biochemistry, immunology, and pharmacology, which are within the skill of the art. Such techniques are explained fully in the literature, such as, *Molecular Cloning: A Laboratory Manual,* $2^{nd}$ *ed.* (Sambrook et al., 1989); *Oligonucleotide Synthesis* (M. J. Gait, ed., 1984); *Animal Cell Culture* (R. I. Freshney, ed., 1987); *Methods in Enzymology* (Academic Press, Inc.); *Current Protocols in Molecular Biology* (F. M. Ausubel et al., eds., 1987, and periodic updates); *PCR: The Polymerase Chain Reaction* (Mullis et al., eds., 1994); and Remington, *The Science and Practice of Pharmacy,* $20^{th}$ *ed.*, (Lippincott, Williams & Wilkins 2003).

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

To facilitate understanding of the invention, a number of terms and abbreviations as used herein are defined below as follows:

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

Cellular Membrane: The term "cellular membrane" as used herein refers to a biological membrane enclosing or separating structure acting as a selective barrier, within or around a cell or an emergent viral particle. The cellular membrane is selectively permeable to ions and organic molecules and controls the movement of substances in and out of cells. The cellular membrane comprises a phospholipid uni- or bilayer, and optionally associated proteins and carbohydrates. As used herein, the cellular membrane refers to a membrane obtained from a naturally occurring biological membrane of a cell or cellular organelles, or one derived therefrom. As used herein, the term "naturally occurring" refers to one existing in nature. As used herein, the term "derived therefrom" refers to any subsequent modification of the natural membrane, such as isolating the cellular membrane, creating portions or fragments of the membrane, removing and/or adding certain components, such as lipid, protein or carbohydrates, from or into the membrane taken from a cell or a cellular organelle. A membrane can be derived from a naturally occurring membrane by any suitable methods. For example, a membrane can be prepared or isolated from a cell or a virus and the prepared or isolated membrane can be combined with other substances or materials to form a derived membrane. In another example, a cell or virus can be recombinantly engineered to produce "non-natural" substances that are incorporated into its membrane in vivo, and the cellular or viral membrane can be prepared or isolated from the cell or the virus to form a derived membrane.

In various embodiments, the cellular membrane covering either of the unilamellar or multilamellar nanoparticles can be further modified to be saturated or unsaturated with other lipid components, such as cholesterol, free fatty acids, and phospholipids, also can include endogenous or added proteins and carbohydrates, such as cellular surface antigen. In such cases, an excess amount of the other lipid components can be added to the membrane wall which will shed until the concentration in the membrane wall reaches equilibrium, which can be dependent upon the nanoparticle environment. Membranes may also comprise other agents that may or may not increase an activity of the nanoparticle. In other examples, functional groups such as antibodies and aptamers can be added to the outer surface of the membrane to enhance site targeting, such as to cell surface epitopes found in cancer cells. The membrane of the nanoparticles can also comprise particles that can be biodegradable, cationic nanoparticles including, but not limited to, gold, silver, and synthetic nanoparticles.

Synthetic or artificial membrane: As used herein, the term "synthetic membrane" or "artificial membrane" refers to a man-made membrane that is produced from organic material, such as polymers and liquids, as well as inorganic materials. A wide variety of synthetic membranes are well known in the art.

Viral membrane: As used herein, the term "membrane derived from a virus" refers to viral envelopes that cover the nucleic acid or protein capsids of a virus, and typically contain cellular membrane proteins derived from portions of the host cell membrane (phospholipid and proteins) and include some viral glycoproteins. The viral envelop fuses with the host's membrane, allowing the capside and viral genome to enter and infect the host.

Nanoparticle: The term "nanoparticle" as used herein refers to nanostructure, particles, vesicles, or fragments thereof having at least one dimension (e.g., height, length, width, or diameter) of between about 1 nm and about 10 μm. For systemic use, an average diameter of about 50 nm to about 500 nm, or 100 nm to 250 nm may be preferred. The terms "nanostructure" includes, but is not necessarily limited to, particles and engineered features. The particles and engineered features can have, for example, a regular or irregular shape. Such particles are also referred to as nanoparticles. The nanoparticles can be composed of organic materials or other materials, and can alternatively be implemented with porous particles. The layer of nanoparticles can be implemented with nanoparticles in a monolayer or with a layer having agglomerations of nanoparticles. As used herein, the nanoparticle consisting an inner core covered by an outer surface comprising the membrane as discussed herein. The invention contemplates any nanoparticles now known and later developed that can be coated with the membrane described herein.

Pharmaceutically active: The terms "pharmaceutically active" as used herein refer to the beneficial biological activity of a substance on living matter and, in particular, on cells and tissues of the human body. A "pharmaceutically active agent" or "drug" is a substance that is pharmaceutically active and a "pharmaceutically active ingredient" (API) is the pharmaceutically active substance in a drug.

Pharmaceutically acceptable: The terms "pharmaceutically acceptable" as used herein means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

Pharmaceutically acceptable salt: The terms "pharmaceutically acceptable salt" as used herein refer to acid addition salts or base addition salts of the compounds, such as the multi-drug conjugates, in the present disclosure. A pharmaceutically acceptable salt is any salt which retains the activity of the parent compound and does not impart any deleterious or undesirable effect on a subject to whom it is administered and in the context in which it is administered. Pharmaceutically acceptable salts may be derived from amino acids including, but not limited to, cysteine. Methods for producing compounds as salts are known to those of skill in the art (see, for example, Stahl et al., Handbook of Pharmaceutical Salts: Properties, Selection, and Use, Wiley-VCH; Verlag Helvetica Chimica Acta, Zürich, 2002; Berge et al., J Pharm. Sci. 66: 1, 1977). In some embodiments, a "pharmaceutically acceptable salt" is intended to mean a salt of a free acid or base of a compound represented herein that is non-toxic, biologically tolerable, or otherwise biologically suitable for administration to the subject. See, generally, Berge, et al., *J. Pharm. Sci.,* 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates.

Pharmaceutically acceptable carrier: The terms "pharmaceutically acceptable carrier" as used herein refers to an excipient, diluent, preservative, solubilizer, emulsifier, adjuvant, and/or vehicle with which a compound, such as a multi-drug conjugate, is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, *The Science and Practice of Pharmacy, 20th ed.*, (Lippincott, Williams & Wilkins 2003). Except insofar as any conventional media or agent is incompatible with the active compound, such use in the compositions is contemplated.

Phospholipid: The term "phospholipid", as used herein, refers to any of numerous lipids contain a diglyceride, a phosphate group, and a simple organic molecule such as choline. Examples of phospholipids include, but are not limited to, Phosphatidic acid (phosphatidate) (PA), Phosphatidylethanolamine (cephalin) (PE), Phosphatidylcholine (lecithin) (PC), Phosphatidylserine (PS), and Phosphoinositides which include, but are not limited to, Phosphatidylinositol (PI), Phosphatidylinositol phosphate (PIP), Phosphatidylinositol bisphosphate (PIP2) and Phosphatidylinositol triphosphate (PIP3). Additional examples of PC include DDPC, DLPC, DMPC, DPPC, DSPC, DOPC, POPC, DRPC, and DEPC as defined in the art.

Therapeutically Effective Amount: As used herein, the term "therapeutically effective amount" refers to those amounts that, when administered to a particular subject in view of the nature and severity of that subject's disease or condition, will have a desired therapeutic effect, e.g., an amount which will cure, prevent, inhibit, or at least partially arrest or partially prevent a target disease or condition. More specific embodiments are included in the Pharmaceutical Preparations and Methods of Administration section below. In some embodiments, the term "therapeutically effective amount" or "effective amount" refers to an amount of a therapeutic agent that when administered alone or in combination with an additional therapeutic agent to a cell, tissue, or subject is effective to prevent or ameliorate the disease or condition such as an infection or the progression of the disease or condition. A therapeutically effective dose further refers to that amount of the therapeutic agent sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously.

Vaccine: a composition capable of eliciting in a patient a beneficial active or passive immune response to a specific antigen. While protective immunity may be desired, it is understood that various levels of temporal immune response can be beneficial.

"Treating" or "treatment" or "alleviation" refers to therapeutic treatment wherein the object is to slow down (lessen) if not cure the targeted pathologic condition or disorder or prevent recurrence of the condition. A subject is successfully "treated" if, after receiving a therapeutic amount of a therapeutic agent, the subject shows observable and/or measurable reduction in or absence of one or more signs and symptoms of the particular disease. Reduction of the signs or symptoms of a disease may also be felt by the patient. A patient is also considered treated if the patient experiences stable disease. In some embodiments, treatment with a therapeutic agent is effective to result in the patients being disease-free 3 months after treatment, preferably 6 months, more preferably one year, even more preferably 2 or more years post treatment. These parameters for assessing successful treatment and improvement in the disease are readily measurable by routine procedures familiar to a physician of appropriate skill in the art.

The term "combination" refers to either a fixed combination in one dosage unit form, or a kit of parts for the combined administration where a compound and a combination partner (e.g., another drug as explained below, also referred to as "therapeutic agent" or "co-agent") may be administered independently at the same time or separately within time intervals, especially where these time intervals allow that the combination partners show a cooperative, e.g., synergistic effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a compound and a combination partner, are both administered to a patient simultaneously in the form of a single entity or dosage. The term "non-fixed combination" means that the active ingredients, e.g., a compound and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Other objects, advantages and features of the present invention will become apparent from the following specification taken in conjunction with the accompanying drawings.

The present invention provides novel nanoparticles, method of using and making thereof. More specifically, the inventive nanoparticle comprises a) an inner core comprising a non-cellular material; and b) an outer surface comprising a membrane derived from a cell or a membrane derived from a virus.

In certain embodiments, the inner core of the inventive nanoparticle supports the outer surface and can be of any shape, including but not limited to, sphere, square, rectangle, triangle, circular disc, cube-like shape, cube, rectangular parallelepiped (cuboid), cone, cylinder, prism, pyramid, right-angled circular cylinder, and other regular or irregular shape. In other embodiments, the non-cellular material of the inner core comprises a biocompatible synthetic material, including but not limited to, poly(lactic-co-glycolic acid), polylactic acid, polyglycolic acid, polycaprolactone, polylysine, polyglutamic acid, and any other suitable synthetic material or the like.

In certain embodiments, the membrane of the outer surface of the invention nanoparticle comprises naturally occurring cellular membrane derived from plasma membrane of a cell from any unicellular (e.g. a bacterium or fungus) or multicellular organisms (e.g., a plant, an animal, a non-human mammal, or a human). The naturally occurring cellular plasma membrane maintains natural structural integrity and activity of the membrane. For instance, the lipid bilayer structure and at least some of the associated membrane proteins embedded therewith are intact, such that the membrane encapsulation substantially lacks immunogenicity to a species or subject from which the membrane is derived.

In certain embodiments, the cell includes, but is not limited to, a blood cell such as a red blood cell (RBC), a white blood cell (WBC), and a platelet, an immune cell, such as a macrophage, a monocyte, a B-cell, and a T-cell, a tumor or cancer cell, and other cells, such as an epithelial cell, an endothelial cell, and a neural cell. In other embodiments, the membrane of the outer surface is derived from non-terminally differentiated or pluripotent stem cells, such as a hematopoietic stem cell, a bone marrow stem cell, a mesenchymal stem cell, a cardiac stem cell, or a neural stem cell. In yet other embodiments, the cellular membrane is derived from a cell component including, but not limited to, an exosome, a secretory vesicle or a synaptic vesicle. In certain embodiments, the outer surface of the nanoparticle of the present invention further comprises a synthetic membrane or synthetic components, along with the naturally derived membrane.

The membranes according to the invention can be obtained and assembled by methods described herein and known in the art, for example, see Desilets et al., *Anticancer Res.* 21: 1741-47; Lund et al., *J Proteome Res* 2009, 8 (6), 3078-3090; Graham, *Methods Mol Biol* 1993, 19, 97-108; Vayro et al., *Biochem J* 1991, 279 (Pt 3), 843-848; Navas et al., *Cancer Res* 1989, 49 (8), 2147-2156; Henon et al., *C R Acad Sci Hebd Seances Acad Sci D* 1977, 285 (1), 121-122; and Boone et al., *J Cell Biol* 1969, 41 (2), 378-392), the entire contents of which are incorporated by reference herewith.

The present invention further provides that the invention nanoparticle comprises a releasable cargo that can be located in any place inside or on the surface of the nanoparticle. In certain embodiments, the releaseable cargo is located within or on the inner core of the inventive nanoparticle. In other embodiments, the releasable cargo is located between the inner core and the outer surface of the inventive nanoparticle. In yet other embodiments, the releasable cargo is located within or on the outer surface of the inventive nanoparticle. A trigger for releasing the releasable cargo from the inventive nanoparticle includes, but is not limited to, a contact between the nanoparticle and a target cell, tissue, organ or subject, or a change of an environmental parameter, such as the pH, ionic condition, temperature, pressure, and other physical or chemical changes, surrounding the nanoparticle.

In certain embodiments, the releasable cargo comprises one or more therapeutic agent, prophylactic agent, diagnostic or marker agent, prognostic agent, or a combination thereof. Examples of therapeutic agents include, but are not limited to, an antibiotic, an antimicrobial, a growth factor, a chemotherapeutic agent, or a combination thereof. Exemplary diagnostic or prognostic agent can be an imaging marker. In yet certain other embodiments, the releasable cargo is a metallic particle comprising a gold particle, a silver particle, or an iron oxide particle. In other embodiments, the releasable cargo is a polymeric particle comprising a poly(lactic-co-glycolic acid) (PCL) particle, a chitosan particle, a hydroxypropyl methacrylamide copolymer (HPMA) particle. In other embodiments, the releasable cargo is a dendrimer particle or an inorganic particle comprising a silica particle, a porous silica particle, a phosphate calcium particle or a quantum dot, or a metallic particle comprising a gold particle, a silver particle, or an iron oxide particle.

The present invention further provides that the inventive nanoparticle can be in any suitable shape, including, but not limited to, sphere, square, rectangle, triangle, circular disc, cube-like shape, cube, rectangular parallelepiped (cuboid), cone, cylinder, prism, pyramid, right-angled circular cylinder, or other regular or irregular shape, and has a diameter from about 10 nm to about 10 μm. In certain embodiments, the invention nanoparticle has a diameter from about 50 nm to about 500 nm.

The present invention further provides that the nanoparticle can substantially lack constituents of the cell from which the cellular membrane is derived or constituents of the virus from which the viral membrane is derived. In certain embodiments, the nanoparticle of the present invention substantially lacks cytoplasm, nucleus and/or cellular organelles of the cell from which the cellular membrane is derived. In yet certain embodiments, the nanoparticle of the present invention substantially maintains natural structural integrity or activity of the cellular membrane, the membrane derived from a virus or the constituents of the cellular membrane or viral membrane. The structural integrity of the cellular membrane includes primary, secondary, tertiary or quaternary structure of the cellular membrane, the membrane derived from a virus or the constituents of the cellular membrane or viral membrane, and the activity of the cellular membrane includes, but is not limited to, binding activity, receptor activity, signaling pathway activity, and any other activities a normal naturally occurring cellular membrane, the membrane derived from a virus or the constituents of the cellular membrane or viral membrane, would have. In certain embodiments, the nanoparticle of the present invention is biocompatible and/or biodegradable.

In certain embodiments, the nanoparticle of the present invention comprises the cellular plasma membrane derived from a red blood cell and an inner core comprising poly (lactic-co-glycolic acid) (PLGA), wherein the nanoparticle substantially lacks hemoglobin and has a half-life in blood circulation in vivo for at least about 2-5 times of a half-life of a nanoparticle having a poly(lactic-co-glycolic acid) (PLGA) inner core coated with polyethylene glycol (PEG). In certain embodiments, such nanoparticle has a half-life in blood circulation in vivo for at least about 5 to about 40 hours.

The present invention also provides a pharmaceutical composition comprising a medicament delivery system comprising an effective amount of the nanoparticle of the present invention. In certain embodiments, the pharmaceutical composition of the present invention further comprises one or more additional active ingredient, with or without a medically or pharmaceutically acceptable carrier or excipient, that can be administered along with or in combination with the nanoparticle of the present invention.

In certain embodiments, the pharmaceutical composition of the present invention is a neoplasm-specific immunogenic composition comprising nanoparticles coated with a cellular membrane derived from cancer cells, such as benign neoplasm cell, a potentially malignant neoplasm cell, a tumor or cancer cell of a subject or cell line, with structural integrity for eliciting an immune response to the neoplasm or cancer cell. In other embodiments, the pharmaceutical composition of the present invention is a cancer vaccine comprising the neoplasm-specific immunogenic composition.

In other embodiments, the pharmaceutical composition of the present invention comprising nanoparticles comprising a cell membrane-inserting toxin, wherein the cellular membrane of the outer surface of the nanoparticle is derived from a target cell or a cellular or intracellular component, and retains a toxin of a bacterial, fugal and an animal source. In certain embodiments, the target cells include, but are not limited to, a blood cell such as a red blood cell (RBC), a white blood cell (WBC), and a platelet, an immune cell, such as a macrophage, a monocyte, a B-cell, and a T-cell, a tumor or cancer cell, and other cells, such as an epithelial cell, an endothelial cell, and a neural cell, or non-terminally differentiated or pluripotent stem cells, such as a hematopoietic stem cell, a bone marrow stem cell, a mesenchymal stem cell, a cardiac stem cell, or a neural stem cell. In certain embodiments, the target cell is a red blood cell. In other embodiments, the intracellular component includes, but are not limited to, exosomes, secretory vesicles, or synaptic vesicles. In certain embodiments, the pharmaceutical composition is an immunogenic composition comprising nanoparticles coated cellular membrane on the outer surface that retains structural integrity for retaining the toxin, or for eliciting an immune response to a natural toxin. In other embodiments, the pharmaceutical composition of the present invention is a vaccine comprising the immunogenic composition.

The inventive pharmaceutical composition or the medicament delivery system comprising the nanoparticle of the present invention can be administered via any suitable administration route, including but not limited to, oral, nasal, inhalational, parental, intravenous, intraperitoneal, subcutaneous, intramuscular, intradermal, topical, or rectal route.

The present invention further provides a method for eliciting an immune response to a target cell of a subject in need. The inventive method comprising administering to the subject in need an effective amount of a pharmaceutical composition or a medicament delivery system comprising the nanoparticle of the present invention, wherein the cellular membrane of the nanoparticle administered substantially retains structural integrity for eliciting the immune response to the target cell. As used herein, the target cell refers to any suitable cells, including but not limited to, blood cells (e.g., RBCs, WBCs, or platelets), immune cells (e.g., B-cells, T-cells, macrophages, or monocytes), tumor or cancer cells (e.g., a benign neoplasm cell, a malignant neoplasm cell), or stem cells (e.g., a hemotopoietic stem cell, a bone marrow stem cell, a mesenchymal stem cell, a cardiac stem cell or a neural stem cell). In certain embodiments, the target cell is a red blood cell. In other embodiments, the target cell is a neoplasm or cancer cell. In certain embodiments, the immune response is an active immune response. In other embodiments, the immune response is a passive immune response. In yet other embodiments, the immune response is protective vaccination. In certain embodiments, the vaccination is neoplasm or cancer-specific vaccination.

The present invention further provides a method for eliciting an immune response against a cell membrane-inserting toxin in a subject in need. The inventive method comprises administering to the subject in need an effective amount of a pharmaceutical composition or a medicament delivery system comprising the nanoparticle of the present invention, wherein the cellular membrane of the nanoparticle retains the toxin and natural structural integrity of the toxin as bound for delivery to a target cell to elicit the immune response against the target cell. In certain embodiments, the target cell is red blood cell, and the toxin is a bacterial, fungal or an animal toxin. In certain embodiments, the immune response is an active immune response. In other embodiments, the immune response is a passive immune response. In yet other embodiments, the immune response is protective vaccination.

The present invention further provides that the inventive methods can be used for treating or preventing a disease, disorder, or condition in a subject in need, such disease or condition includes, but is not limited to, an infectious disease, a parasitic disease, a neoplasm, a disease of the blood and blood-forming organs, a disorder involving the immune mechanism, endocrine, nutritional and metabolic diseases, a mental and behavioral disorder, a disease of the nervous system, a disease of the eye and adnexam, a disease of the ear and mastoid process, a disease of the circulatory system, a disease of the respiratory system, a disease of the digestive system, a disease of the skin and subcutaneous tissue, a disease of the musculoskeletal system and connective tissue, a disease of the genitourinary system, pregnancy, childbirth and the puerperium, a condition originating in the perinatal period, a congenital malformation, a deformation, a chromosomal abnormality, an injury, a poisoning, a consequence of external causes, and an external cause of morbidity and mortality.

In certain embodiments, the inventive method is used for treating or preventing infectious diseases caused by pathogenic microorganisms, such as bacteria, viruses, parasites or fungi. In other embodiments, the inventive method is used for treating or preventing cancer or a neoplasm condition. As used herein, a subject in need refers to an animal, a non-human mammal or a human. As used herein, "animals" include a pet, a farm animal, an economic animal, a sport animal and an experimental animal, such as a cat, a dog, a horse, a cow, an ox, a pig, a donkey, a sheep, a lamb, a goat, a mouse, a rabbit, a chicken, a duck, a goose, a primate, including a monkey and a chimpanzee. In certain embodiments, the cellular membrane of the nanoparticle used for the inventive method is derived from a cell of the same species of the subject. In certain embodiments, the cellular membrane of the nanoparticle used for the inventive method is derived from a red blood cell of the same species of the subject and the red blood cell has the same blood type of the subject. In certain embodiments, the cellular membrane of the nanoparticle used in the inventive method is derived from a cell of the subject.

The present invention further provides that the inventive methods for eliciting an immune response to a target cell of a subject in need or to treat or prevent a disease, disorder, or condition further comprises administering the subject in need one or more other active ingredient with or without a pharmaceutically acceptable carrier, adjuvant, or excipient, along or in combination with the pharmaceutical composition or medicament delivery system comprising the nanoparticles of the present invention. The inventive methods further provide that the nanoparticle of the present invention is administered to a target site of the subject in need, including but not limited to, a target dermal site, blood or plasma, a target organ, a target tumor site, or target cells, and further provides a mechanism to trigger the release of a releasable cargo at the target site. Mechanisms for triggering the releasable cargo include, but are not limited to, a contact between the nanoparticle of the present invention and a target cell, tissue, organ or subject, or a change of an environmental parameter, such as the pH, ionic condition, temperature, pressure, and other physical or chemical changes, surrounding the nanoparticle of the present invention.

The present invention further provides a method for making the nanoparticle, as well as the pharmaceutical composition or medicament delivery system comprising the nanoparticles thereof. Such inventive method of making the nanoparticle comprises a) combining an inner core comprising a non-cellular material, and an outer surface comprising a membrane derived from a cell or virus, and optionally, a synthetic membrane, and b) exerting exogenous energy on the combination to form a nanoparticle, wherein the inner core supports the outer surface. In certain embodiments, the exogenous energy is a mechanical energy exerted by extrusion. In other embodiments, the exogenous energy is an acoustic energy exerted by sonication. In yet other embodiment, the exogenous energy is a thermal energy exerted by heating. The present inventive method contemplates any other suitable exogenous energy delivery system now existing or later developed being used in forming a nanoparticle.

Cancer Specific Immunogenic Composition or Vaccine

The present invention provides a neoplasm specific immunogenic composition comprising an effective amount of a nanoparticle, which comprises an inner core comprising a non-cellular material, and an outer surface comprising a cellular membrane derived from a neoplasm cell, and optically, a synthetic membrane as well. In certain embodiments, the cellular membrane is derived from a benign neoplasm cell, a potentially malignant neoplasm cell or a cancer cell. In certain embodiments, the cellular membrane is derived from a cancer cell line. In other embodiments, the cellular membrane is derived from a cancer cell of a subject. The neoplasm specific immunogenic composition of the present invention can further provide that the cellular membrane in the outer surface of the nanoparticle substantially retains its structural integrity for eliciting an immune response to the neoplasm cell. As used herein, the structural integrity includes primary, secondary, tertiary, or quaternary structure of the cellular membrane or its constituents.

In certain embodiments, the inner core comprises a biocompatible or a synthetic material, and supports the outer surface of the nanoparticle. Examples of the inner core material include, but are not limited to, poly(lactic-co-glycolic acid) (PLGA), polylactic acid (PLA), polyglycolic acid (PGA), polycaprolactone (PCL), polylysine, polyglutamic acid, and any other synthetic materials or like now known or later development that can be used for this purpose. In certain embodiments, the inner core comprises PLGA and the outer surface comprises a plasma membrane derived from a neoplasm cell.

In certain embodiments, the neoplasm specific immunogenic composition of the present invention comprises the nanoparticle that further comprises one or more active ingredient or a releaseable cargo, and can be in any shape, including but not limited to, sphere, square, rectangle, triangle, circular disc, cube-like shape, cube, rectangular parallelepiped (cuboid), cone, cylinder, prism, pyramid, right-angled circular cylinder and other regular or irregular shape. The diameter of the nanoparticle can be from about 10 nm to about 10 μm. In certain embodiments, the diameter of the nanoparticle in the neoplasm specific immunogenic composition is about 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 μm, 2 μm, 3 μm, 4 μm, 5 μm, 6 μm, 7 μm, 8 μm, 9 μm, and 10 μm. In certain embodiments, the nanoparticle in the neoplasm specific immunogenic composition substantially lacks constituents of the neoplasm cell from which the cellular membrane is derived.

The present invention further provides that the neoplasm specific immunogenic composition further comprises an immunogenic adjuvant or immunopotentiator. As used herein, the "immunogenic adjuvant" is a substance or composition which can induce and/or enhance an immune response against an antigen. As used herein, the "immunopotentiator" refers to an agent that on inoculation enhances the immune response. The present invention contemplates any suitable immunogenic adjuvant or immunopotentiator now known or later developed, and the type of the immunogenic adjuvant or immunopotentiator used along with or in combination with the nanoparticle of the present invention is not particularly limited. Exemplary immunogenic adjuvant can be Freund's complete adjuvant which is a mixture of light mineral oil, Arlacel detergent, and inactivated Mycobacterium tuberculosis bacilli. Exemplary immunopotentiator includes Bacille Calmette-Guerin (BCG), Corynebacterium Parvum, Brucella abortus extract, glucan, levamisole, tilorone, an enzyme and a non-virulent virus.

The present invention further provides a vaccine containing the aforementioned neoplasm specific immunogenic composition and an antigen. In certain embodiments, the antigen consists of one kind or two or more kinds of antigens selected from the group consisting of tumor tissues, tumor cells, tumor cell ingredients, tumor antigen proteins, and tumor antigen peptides, and which is for use in prophylactic and/or therapeutic treatment of a tumor. If a foreign protein is used as the antigen, antibodies directed to the antigen can be efficiently produced in a mammal other than human with the aforementioned neoplasm specific immunogenic composition. Therefore, an antibody-producing animal and an antibody-producing cell or antibody gene derived from the antibody-producing animal are provided by the present invention. The present invention therefore provides a tumor vaccine comprising the aforementioned neoplasm specific immunogenic composition for administration into a tumor tissue of a subject including human to induce an antitumor immune response in the living body of the mammal.

The present invention further provides a method for inducing a systemic or antitumor immune response, thus resulting in treating or preventing a neoplasm in a subject, such method comprises the step of administrating an effective amount of the aforementioned neoplasm specific immunogenic composition or a vaccine therefrom, to a subject in need, wherein the cellular membrane of the outer surface of the nanoparticle in the aforementioned neoplasm specific immunogenic composition or vaccine substantially retains its structural integrity for eliciting an immune response to the neoplasm cell. As used herein, the immune response can be a T-cell mediated immune response, and/or a B-cell mediated immune response. As used herein, the neoplasm refers to a benign neoplasm, a potentially malignant neoplasm or a cancer. In certain embodiment, the neoplasm is a cancer, and the type of the cancer that can be treated or prevented by the inventive method is not limited.

In certain embodiments, the cellular membrane of the outer surface of the nanoparticle in the aforementioned neoplasm specific immunogenic composition or vaccine is derived from a cancer cell line, or a cancer cell of the same or different species of the subject, or the same or different subject. As used herein, the "subject" refers to non-human mammal, an animal, or a human.

The present invention further provides administering to the subject in need one or more other active ingredient, with or without a pharmaceutically acceptable carrier or excipient, along or in combination with the aforementioned neoplasm specific immunogenic composition or vaccine. The neoplasm specific immunogenic composition or the vaccine of the present invention, as well as the other active ingredient, can be administered, alone or in combination, via any suitable administration route, including but not limited to oral, nasal, inhalational, parental, intravenous, intraperitoneal, subcutaneous, intramuscular, intradermal, topical, or rectal. In certain embodiments, the neoplasm specific immunogenic composition or the vaccine of the present invention, as well as the other active ingredient, is administered via a medicament delivery system to the subject in need. The type of administration route or the type of other active ingredient used herein are not particularly limited.

Treatment of Disease or Condition Associated with Cell Membrane Inserting Toxins The present invention provides a pharmaceutical composition for treating or preventing a disease or condition associated with a cell membrane inserting toxin, which pharmaceutical composition comprises an effective amount of a nanoparticle comprising an inner core comprising a non-cellular material and an outer surface comprising a cellular membrane derived from a target cell, and optionally, a synthetic membrane as well. In certain embodiments, the inner core supports the outer surface and comprises a biocompatible or a synthetic material. Examples of the biocompatible or a synthetic material include, but are not limited to, poly(lactic-co-glycolic acid) (PLGA), polylactic acid (PLA), polyglycolic acid (PGA), polycaprolactone (PCL), polylysine, polyglutamic acid, and any other biocompatible or synthetic material that are suitable. The present invention contemplates any biocompatible or synthetic material, now known or later developed, that can be used in the inner core of the nanoparticle, and the type of such material is not particularly limited.

In certain embodiments, the cellular membrane is a plasma membrane derived from red blood cells, and wherein the cellular membrane or plasma membrane in the outer surface of the nanoparticle substantially retains its structural integrity for substantially retaining the toxin. In certain embodiments the toxin inserts into the cellular membrane or plasma membrane of the target cell as part of the natural pathological mechanism.

As used herein, the "toxin" refers to a toxic material or product of plants, animals, microorganisms (including, but not limited to, bacteria, virus, fungi, rickettsiae or protozoa), or infectious substances, or a recombinant or synthesized molecule, whatever their origin and method of production. In certain embodiment, the "toxin" includes a bacterial, fungal, or animal toxin that produced within living cells or organisms.

In certain embodiments, the bacterial toxin includes exotoxin and endotoxin. As used herein, "exotoxins" are generated by the bacteria and actively secreted, while "endotoxins" are part of the bacteria itself (e.g., bacterial outer membrane), and it is not released until the bacteria is killed by the immune system. The present invention contemplates any exotoxin and endotoxin now known and later discovered. The type of bacterial toxin inserted in the cellular membrane is not particularly limited. In certain embodiments, the bacterial toxin is a cell membrane inserting toxin from *S. aureus*, such as alpha-hemolysin.

The present invention further contemplates any fungal toxins now known and later discovered, including but not limited to, aflatoxin, citrinin, ergotamine, fumonisins, ergovaline, ochratoxin, phomopsin, slaframine, sporidesmin, trichothecenes (e.g. satratoxin, deoxynivalenol), zearalenone. The type of fungal toxin inserted in the cellular membrane is not particularly limited.

The animal toxins contemplated in the present invention includes any poison substances produced by an animal. Examples of animal toxins include, but are not limited to, cardiovascular toxins, gastrointestinal toxins respiratory toxin, neurological toxins, kidney/organ failure toxins. The present invention contemplates any animal toxins now known and later discovered, and the type of animal toxin inserted in the cellular membrane is not particularly limited. In certain embodiments, the animal toxin inserting into the cell membrane is from an arthropod such as the insects, arachnids and crustaceans or a reptile such as crocodilia, rhynchocephalia, squamata (including lizards and snakes) and testudines.

In certain embodiments, the pharmaceutical composition of the present invention for treating or preventing a disease or condition associated with a cell membrane inserting toxin comprises the nanoparticle that further comprises one or more other active ingredient or a releaseable cargo, with or without a pharmaceutically acceptable carrier or excipient.

The nanoparticles contained in such pharmaceutical composition is biodegradable, and can be in any shape, including but not limited to, sphere, square, rectangle, triangle, circular disc, cube-like shape, cube, rectangular parallelepiped (cuboid), cone, cylinder, prism, pyramid, right-angled circular cylinder and other regular or irregular shape. The diameter of the nanoparticle can be from about 10 nm to about 10 μm. In certain embodiments, the diameter of the nanoparticle in the neoplasm specific immunogenic composition is about 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 μm, 2 μm, 3 μm, 4 μm, 5 μm, 6 μm, 7 μm, 8 μm, 9 μm, and 10 μm.

The present invention further provides a method for treating or preventing a disease or condition associated with a cell membrane inserting toxin in a subject, which method comprises administering, to a subject in need of such treatment or prevention, an effective amount of the aforementioned pharmaceutical composition. As used herein, the "subject" refers to non-human mammal, an animal, or a human. In certain embodiments, the cellular membrane of the outer surface of the nanoparticle in the aforementioned pharmaceutical composition is derived from a cell of the same species of the subject. In certain embodiments, the plasma membrane is derived from a red blood cell of the same species of the subject and the RBC has the same blood type of the subject. In other embodiments, the cellular membrane or plasma membrane is derived from a cell of the subject.

The present invention further provides administering to the subject in need one or more other active ingredient, with or without a pharmaceutically acceptable carrier or excipient, along or in combination with the aforementioned pharmaceutical composition. The aforementioned pharmaceutical composition of the present invention, as well as the other active ingredient, can be administered, alone or in combination, via any suitable administration route, including but not limited to, oral, nasal, inhalational, parental, intravenous, intraperitoneal, subcutaneous, intramuscular, intradermal, topical, or rectal. In certain embodiments, the aforementioned pharmaceutical composition of the present invention, as well as the other active ingredient, is administered via a medicament delivery system to the subject in need. The type of administration route or the type of other active ingredient used herein are not particularly limited.

Vaccine for Disease or Condition Associated with Cell Membrane Inserting Toxins

The present invention provides an immunogenic composition, which immunogenic composition comprises an effective amount of a nanoparticle, said nanoparticle comprising an inner core comprising a non-cellular material, and an outer surface comprising a cellular membrane derived from a cell and a cell membrane inserting toxin, and optionally, a synthetic membrane as well. In certain embodiments, the inner core supports the outer surface and comprises a biocompatible or a synthetic material. Examples of the biocompatible or a synthetic material include, but are not limited to, poly(lactic-co-glycolic acid) (PLGA), polylactic acid (PLA), polyglycolic acid (PGA), polycaprolactone (PCL), polylysine, polyglutamic acid, and any other biocompatible or synthetic material that are suitable. The present invention contemplates any biocompatible or synthetic material, now known or later developed, that can be used in the inner core of the nanoparticle, and the type of such material is not particularly limited.

In certain embodiments, the cellular membrane is a plasma membrane derived from a cell, such as red blood cells, and wherein the cellular membrane or plasma membrane in the outer surface of the nanoparticle substantially retains its structural integrity for substantially retaining the toxin or for eliciting an immune response to a natural toxin. As used herein, the structural integrity of the toxin includes primary, secondary, tertiary and/or quaternary structure of the toxin as bound to a target cell. In certain embodiments the toxin inserts into the cellular membrane or plasma membrane of the target cell as part of the natural pathological mechanism. The definition and types of "toxin" is fully described above. In certain embodiments, the nanoparticles in the aforementioned immunogenic composition is biodegradable.

In certain embodiments, the immunogenic composition of the present invention comprises the nanoparticle that further comprises one or more active ingredient or a releaseable cargo, and can be in any shape, including but not limited to, sphere, square, rectangle, triangle, circular disc, cube-like shape, cube, rectangular parallelepiped (cuboid), cone, cylinder, prism, pyramid, right-angled circular cylinder and other regular or irregular shape. The diameter of the nanoparticle is from about 10 nm to about 10 μm. In certain embodiments, the diameter of the nanoparticle in the neoplasm specific immunogenic composition is about 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 μm, 2 μm, 3 μm, 4 μm, 5 μm, 6 μm, 7 μm, 8 μm, 9 μm, and 10 μm. In certain embodiments, the nanoparticle in the immunogenic composition substantially lacks constituents of the cell from which the cellular membrane is derived.

The present invention further provides that the immunogenic composition further comprises an immunogenic adjuvant or immunopotentiator. The definition and the types of immunogenic adjuvant or immunopotentiator is fully described above. The present invention contemplates any suitable immunogenic adjuvant or immunopotentiator now known or later developed, and the type of the immunogenic adjuvant or immunopotentiator used along with or in combination with the nanoparticle of the present invention is not particularly limited.

The present invention further provides a vaccine containing the aforementioned immunogenic composition. In this embodiment, the cell membrane inserting toxin is used as the antigen, antibodies directed to the cell membrane inserting toxin can be efficiently produced in a mammal other than human with the aforementioned immunogenic composition. Therefore, an antibody-producing animal and an antibody-producing cell or antibody gene derived from the antibody-producing animal are provided by the present invention. The present invention therefore provides a vaccine comprising the aforementioned immunogenic composition for administration into a target tissue of a subject including human to induce an immune response in the living body of the mammal.

The present invention further provides a method for inducing a systemic or anti-disease immune response, thus resulting in treating or preventing the target disease in a subject, such method comprises the step of administrating an effective amount of the aforementioned immunogenic composition or a vaccine therefrom, to a subject in need, wherein the cellular membrane of the outer surface of the nanoparticle in the aforementioned immunogenic composition or vaccine substantially retains its structural integrity for eliciting an immune response to the target disease cell. As used herein, the immune response is T-cell mediated immune response, B-cell mediated immune response. The present invention contemplates any diseases, disorders, or physiological or pathological conditions, including, but not limited to, an infectious disease, a parasitic disease, a neoplasm, a disease of the blood and blood-forming organs, a disorder involving the immune mechanism, endocrine, nutritional and metabolic diseases, a mental and behavioral disorder, a disease of the nervous system, a disease of the eye and adnexam, a disease of the car and mastoid process, a disease of the circulatory system, a disease of the respiratory system, a disease of the digestive system, a disease of the skin and subcutaneous tissue, a disease of the musculoskeletal system and connective tissue, a disease of the genitourinary system, pregnancy, childbirth and the puerperium, a condition originating in the perinatal period, a congenital malformation, a deformation, a chromosomal abnormality, an injury, a poisoning, a consequence of external causes, and an external cause of morbidity and mortality.

In certain embodiments, the cellular membrane of the outer surface of the nanoparticle in the aforementioned immunogenic composition or vaccine is derived from a cell line, or a disease cell of the same or different species of the subject, or the same or different subject. As used herein, the "subject" refers to non-human mammal, an animal, or a human.

The present invention further provides administering to the subject in need one or more other active ingredient, with or without a pharmaceutically acceptable carrier or excipient, along or in combination with the aforementioned immunogenic composition or vaccine. The aforementioned immunogenic composition or the vaccine of the present invention, as well as the other active ingredient, can be administered, alone or in combination, via any suitable administration route, including but not limited to oral, nasal, inhalational, parental, intravenous, intraperitoneal, subcutaneous, intramuscular, intradermal, topical, or rectal. In certain embodiments, the immunogenic composition or the vaccine of the present invention, as well as the other active ingredient, is administered via a medicament delivery system to the subject in need. The type of administration route or the type of other active ingredient used herein are not particularly limited.

The present invention is further illustrated by the following exemplary embodiments:

1. A nanoparticle comprising:
   a) an inner core comprising a non-cellular material; and
   b) an outer surface comprising a cellular membrane derived from a cell or a membrane derived from a virus.
2. The nanoparticle of embodiment 1, wherein the inner core comprises a biocompatible or a synthetic material selected from the group consisting of poly(lactic-co-glycolic acid) (PLGA), polylactic acid (PLA), polyglycolic acid (PGA), polycaprolactone (PCL), polylysine, and polyglutamic acid.
3. The nanoparticle of any of the embodiments 1-2, wherein the inner core supports the outer surface.
4. The nanoparticle of any of the embodiments 1-3, wherein the cellular membrane comprises a plasma membrane or an intracellular membrane.
5. The nanoparticle of any of the embodiments 1-4, wherein the cellular membrane is derived from a unicellular organism selected from a bacterium and a fungus, or a multicellular organism selected from a plant, a vertebrate, a non-human mammal, and a human.
6. The nanoparticle of any of the embodiments 1-5, wherein the cellular membrane is derived from a blood cell, a tumor cell, a cancer cell, an immune cell, a stem cell, an endothelial cell, an exosome, a secretory vesicle or a synaptic vesicle.
7. The nanoparticle of embodiment 6, wherein the cellular membrane comprises a plasma membrane derived from a red blood cell.
8. The nanoparticle of any of the embodiments 1-7, which further comprises a releasable cargo.
9. The nanoparticle of embodiment 8, wherein the releasable cargo is located within or on the inner core, between the inner core and the outer surface, or within or on the outer surface.
10. The nanoparticle of any of the embodiments 8-9, wherein the release of the releasable cargo is triggered by a contact between the nanoparticle and a target cell, tissue, organ or subject, or by a change of a physical parameter surrounding the nanoparticle.
11. The nanoparticle of any of the embodiments 8-10, wherein the releasable cargo is a therapeutic agent, a prophylactic agent, a diagnostic or marker agent, a prognostic agent, or a combination thereof.
12. The nanoparticle of any of the embodiments 8-11, wherein the releasable cargo is a metallic particle, a polymeric particle, a dendrimer particle, or an inorganic particle.
13. The nanoparticle of any of the embodiments 1-12, wherein the nanoparticle has a diameter from about 10 nm to about 10 μm.
14. The nanoparticle of any of the embodiments 1-13, wherein the nanoparticle substantially lacks constituents of the cell from which the cellular membrane is derived or constituents of the virus from which the viral membrane is derived.
15. The nanoparticle of embodiment 14, wherein the cellular membrane comprises a plasma membrane derived from a red blood cell and the nanoparticle substantially lacks hemoglobin.
16. The nanoparticle of any of the embodiments 1-15, wherein the nanoparticle substantially maintains natural structural integrity or activity of the cellular membrane, the membrane derived from a virus or the constituents of the cellular membrane or viral membrane.
17. The nanoparticle of any of the embodiments 1-16, wherein the nanoparticle is biocompatible or biodegradable.
18. The nanoparticle of embodiment 1, wherein the inner core comprises PLGA and the outer surface comprises a plasma membrane derived from a red blood cell.
19. The nanoparticle of embodiment 18, wherein the nanoparticle has a half-life in blood circulation in vivo for at least about 2-5 times of the half-life of a PEG-coated, comparable nanoparticle, or has a half-life in blood circulation in vivo for at least about 5 to about 40 hours.
20. The nanoparticle of any of the embodiments 1-19, wherein the nanoparticle substantially lacks immunogenicity to a species or subject from which the cellular membrane is derived.
21. The nanoparticle of any of the embodiments 1-20, wherein the outer surface comprises a naturally occurring cellular or viral membrane and further comprises a synthetic membrane.

22. A medicament delivery system, which comprises an effective amount of the nanoparticle of any of the embodiments 1-21.
23. The medicament delivery system of embodiment 22, further comprising another active ingredient, or a medically or pharmaceutically acceptable carrier or excipient.
24. A pharmaceutical composition comprising an effective amount of the nanoparticle of any of the embodiments 1-21 and a pharmaceutically acceptable carrier or excipient.
25. The pharmaceutical composition of embodiment 24 further comprising another active ingredient.
26. A method for treating or preventing a disease or condition in a subject in need comprising administering to said subject an effective amount of the nanoparticle of any of the embodiments 1-21, the medicament delivery system of any of the embodiments 22-23, or the pharmaceutical composition of any of the embodiments 24-25.
27. The method of embodiment 26, wherein the subject is a human or a non-human mammal.
28. The method of any of the embodiments 26-27, wherein the cellular membrane in the nanoparticle is derived from a cell of the same species of the subject or is derived from a cell of the subject.
29. The method of embodiment 28, wherein the cellular membrane in the nanoparticle is derived from a red blood cell of the same species of the subject and the red blood cell has the same blood type of the subject.
30. The method of any of the embodiments 26-29 further comprising administering another active ingredient, or a pharmaceutically acceptable carrier or excipient to the subject in need, or the nanoparticle is administered via a medicament delivery system.
31. Use of an effective amount of the nanoparticle of any of the embodiments 1-21 for the manufacture of a medicament for treating or preventing a disease or condition in a subject in need.
32. A process for making a nanoparticle comprising:
    a) combining an inner core comprising a non-cellular material, and an outer surface comprising a cellular membrane derived from a cell or a membrane derived from a virus; and
    b) exerting exogenous energy on the combination to form a nanoparticle comprising said inner core and said outer surface.
33. The process of embodiment 32, wherein the exogenous energy is a mechanical energy, an acoustic energy, or a thermal energy.
34. The process of embodiment 32, wherein said cellular membrane is a naturally occurring cellular membrane derived from a cell, or a membrane is a naturally occurring membrane derived from a virus.
35. The process of embodiment 33, wherein said outer surface further comprises a synthetic membrane, and the nanoparticle produced comprises said inner core and an outer surface comprising said cellular membrane or viral membrane and the synthetic membrane.
36. A neoplasm specific immunogenic composition comprising an effective amount of a nanoparticle comprising an inner core comprising a non-cellular material, and an outer surface comprising a cellular membrane derived from a neoplasm cell.
37. The neoplasm specific immunogenic composition of embodiment 36, wherein the cellular membrane is derived from a benign neoplasm cell, a potentially malignant neoplasm cell, a cancer cell, a cancer cell line, or a cancer cell of a subject.
38. The neoplasm specific immunogenic composition of embodiment 36 or 37, wherein the cellular membrane in the outer surface of the nanoparticle substantially retains its structural integrity for eliciting an immune response to the neoplasm cell.
39. The neoplasm specific immunogenic composition of any of the embodiments 36-38, wherein the inner core supports the outer surface.
40. The neoplasm specific immunogenic composition of any of the embodiments 36-39, wherein the inner core comprises PLGA and the outer surface comprises a plasma membrane derived from a neoplasm cell.
41. The neoplasm specific immunogenic composition of any of the embodiments 37-40, wherein the nanoparticle further comprises another active ingredient, or a releasable cargo.
42. The neoplasm specific immunogenic composition of any of the embodiments 37-41, wherein the nanoparticle has a diameter from about 10 nm to about 10 μm.
43. The neoplasm specific immunogenic composition of any of the embodiments 37-42, wherein the nanoparticle substantially lacks constituents of the neoplasm cell from which the cellular membrane is derived.
44. The neoplasm specific immunogenic composition of any of the embodiments 37-43 further comprising an immunogenic adjuvant or an immunopotentiator.
45. The neoplasm specific immunogenic composition of any of the embodiments 37-44, wherein the outer surface of the nanoparticle comprises a naturally occurring cellular or viral membrane and further comprises a synthetic membrane.
46. A vaccine comprising the neoplasm specific immunogenic composition of any of the embodiments 37-45.
47. A method for treating or preventing a neoplasm in a subject in need comprising administering to said subject an effective amount of the neoplasm specific immunogenic composition of any of the embodiments 37-45, or the vaccine of embodiment 46.
48. The method of embodiment 47, wherein the subject is a human or a non-human mammal.
49. The method of embodiments 47 or 48, wherein the cellular membrane is derived from a neoplasm cell of the same species of the subject, or a neoplasm cell of the subject.
50. The method of any of the embodiments 47-49 further comprising administering to said subject another active ingredient or a pharmaceutically acceptable carrier or excipient.
51. Use of an effective amount of the nanoparticle of any of the embodiments 1-21 for the manufacture of a neoplasm or cancer specific immunogenic composition, or an effective amount of the neoplasm specific immunogenic composition of any of the embodiments 37-45 for the manufacture of a vaccine for treating or protecting a subject against a neoplasm.
52. A pharmaceutical composition for treating or preventing a disease or condition associated with a cell membrane inserting toxin, wherein said pharmaceutical composition comprises an effective amount of a nanoparticle comprising an inner core comprising a non-cellular material and an outer surface comprising a cellular or plasma membrane derived from a target cell.
53. The pharmaceutical composition of embodiment 52, wherein the toxin inserts into the cellular membrane or plasma membrane of the target cell as part of the natural pathological mechanism, or the cellular membrane or plasma membrane in the outer surface of the nanoparticle substantially retains the toxin.

54. The pharmaceutical composition of embodiment 52 or 53, wherein the toxin is a bacterial, fungal, or animal toxin.

55. The pharmaceutical composition of any of the embodiments 52-54, wherein the inner core supports the outer surface, and the cellular membrane in the outer surface of the nanoparticle substantially retains its structural integrity for substantially retaining the toxin.

56. The pharmaceutical composition of any of the embodiments 52-55, wherein the outer surface of the nanoparticle comprises a naturally occurring cellular or viral membrane and further comprises a synthetic membrane.

57. The pharmaceutical composition of any of the embodiments 52-56, wherein the nanoparticle is biocompatible, biodegradable, or comprises a synthetic material.

58. The pharmaceutical composition of any of the embodiments 52-57, wherein the outer surface comprises a plasma membrane derived from a red blood cell.

59. The pharmaceutical composition of any of the embodiments 52-58 further comprising another active ingredient, or a pharmaceutically acceptable carrier or excipient.

60. A method for treating or preventing a disease or condition associated with a cell membrane inserting toxin in a subject in need comprising administering to said subject an effective amount of the pharmaceutical composition of any of the embodiments 52-59.

61. The method of embodiment 60, wherein the subject is a human or a non-human mammal.

62. The method of embodiment 60 or 61, wherein the cellular membrane or plasma membrane is derived from a cell of the same species of the subject or a cell of the subject.

63. The method of embodiment 62, wherein the plasma membrane is derived from a red blood cell of the same species of the subject and the red blood cell has the same blood type of the subject.

64. The method of any of the embodiments 60-63 further comprising administering another active ingredient or a pharmaceutically acceptable carrier or excipient to said subject.

65. Use of an effective amount of the pharmaceutical composition of any of the embodiments 52-59 for the manufacture of a medicament for treating or preventing a disease or condition associated with a cell membrane inserting toxin in a subject.

66. An immunogenic composition comprising an effective amount of a nanoparticle comprising an inner core comprising a non-cellular material, and an outer surface comprising a cellular membrane derived from a cell and a cell membrane inserting toxin.

67. The immunogenic composition of embodiment 66, wherein the cellular membrane is a plasma membrane derived from a cell.

68. The immunogenic composition of embodiment 66 or 67, wherein the toxin inserts into the cellular or plasma membrane of the target cell as part of the natural pathological mechanism, or the cellular or plasma membrane in the outer surface of the nanoparticle substantially retains the toxin.

69. The immunogenic composition of any of the embodiments 66-68, wherein the toxin in the outer surface of the nanoparticle substantially retains its natural structural integrity for eliciting an immune response to a natural toxin.

70. The immunogenic composition of any of the embodiments 66-69, wherein the toxin is a bacterial, fungal, or animal toxin.

71. The immunogenic composition of any of the embodiments 66-70, wherein the outer surface of the nanoparticle comprises a naturally occurring cellular or viral membrane and further comprises a synthetic membrane.

72. The immunogenic composition of any of the embodiments 66-71, wherein the nanoparticle is biocompatible, biodegradable, or comprises a synthetic material.

73. The immunogenic composition of any of the embodiments 66-72, wherein the inner core supports the outer surface.

74. The immunogenic composition of any of the embodiments 66-73, wherein the outer surface comprises a plasma membrane derived from a red blood cell.

75. The immunogenic composition of any of the embodiments 66-74 further comprising another active ingredient or an immunogenic adjuvant or immunopotentiator.

76. A vaccine comprising the immunogenic composition of any of the embodiments 66-75.

77. A method for eliciting an immune response to a cell membrane inserting toxin in a subject comprising administering to said subject an effective amount of the immunogenic composition of any of the embodiments 66-75.

78. A method for protecting a subject against a cell membrane inserting toxin comprising administering to said subject an effective amount of the vaccine of embodiment 76.

79. The method of embodiment 77 or 78, wherein the toxin is a bacterial, fungal, or animal toxin.

80. The method of any of the embodiments 77-79, wherein the subject is a human or a non-human mammal.

81. The method of any of the embodiments 77-80, wherein the cellular membrane or plasma membrane is derived from a cell of the same species of the subject or a cell of the subject.

82. The method of embodiment 81, wherein the plasma membrane is derived from a red blood cell of the same species of the subject and the red blood cell has the same blood type of the subject.

83. The method of any of the embodiments 77-82 further comprising administering another active ingredient or a pharmaceutically acceptable carrier or excipient to said subject.

84 The method of any of the embodiments 77-83, wherein the immune response is a T-cell mediated immune response, or a B-cell mediated immune response.

85. Use of an effective amount of a nanoparticle for the manufacture of an immunogenic composition against a cell membrane inserting toxin, wherein said nanoparticle comprises an inner core comprising a non-cellular material, and an outer surface comprising a cellular membrane derived from a cell and said cell membrane inserting toxin.

86. Use of an effective amount of the immunogenic composition of any of the embodiments 66-75 for the manufacture of a vaccine for protecting a subject against a cell membrane inserting toxin.

EXAMPLES

Aspects of the present teachings may be further understood in light of the following examples, which should not be construed as limiting the scope of the present teachings in any way. Some of the Examples described herein are also described in Hu et al., PNAS, 108(27):10980-10985 (2011), the content of which is incorporated by reference in its entirety.

Example 1

Erythrocyte Membrane-Camouflaged Polymeric Nanoparticles as a Biomimetic Delivery Platform By extruding poly(lactic-co-glycolic acid) (PLGA) particles with preformed RBC membrane-derived vesicles, inventors coat the sub-100 nm polymeric particles with the bilayered RBC membranes including both lipids and the corresponding surface proteins. This approach aims to camouflage the nanoparticle surface with the erythrocyte exterior for long circulation while retaining the applicability of the polymeric core. The inventors report the physical characterizations, physicochemical properties, protein contents, pharmacokinetics, and biodistributions of this biomimetic nanoparticle delivery platform.

The preparation process of the RBC membrane-coated nanoparticles is divided into two parts: membrane vesicle derivation from RBCs and vesicle-particle fusion (FIG. 1). The derivation of RBC membrane vesicles follows a previously reported method with slight modifications (13). Briefly, RBCs were first purified from the fresh blood of male ICR mice (6-8 wks) from Charles River Laboratories (Wilmington, MA) by centrifugation and PBS wash. The isolated RBCs then underwent membrane rupture in a hypotonic environment to remove its intracellular contents. Next, the emptied RBCs were washed and extruded through 100 nm porous membranes to create RBC membrane-derived vesicles. To synthesize the RBC membrane-camouflaged polymeric nanoparticles, PLGA particles of approximately 70 nm in diameter were first prepared from 0.67 dL/g carboxyl-terminated PLGA polymer using a solvent displacement method (14).

The resulting PLGA nanoparticles were subsequently fused with the RBC membrane-derived vesicles through mechanical extrusion. Based on calculations from PLGA polymer density, nanoparticle size, the erythrocyte lipid contents, and the estimated project area of a lipid molecule, each milligram of PLGA nanoparticles was mixed with vesicles derived from 1 mL of blood for complete particle coating. The mixture was physically extruded through an apparatus with 100 nm pores. The mechanical force facilitated the sub-100 nm PLGA nanoparticles to cross the lipid bilayers, resulting in vesicle-particle fusion. Repeated passing through the extruder overcomes previously reported issues with liposome-particle fusion, such as broad particle size distribution, incomplete particle coating, and inconsistent lipid shells (15). It should also be noted that the bilayer structure of the RBC membranes is retained throughout the entire preparation process to minimize the loss of and damages to the membrane proteins.

Figure 2B:
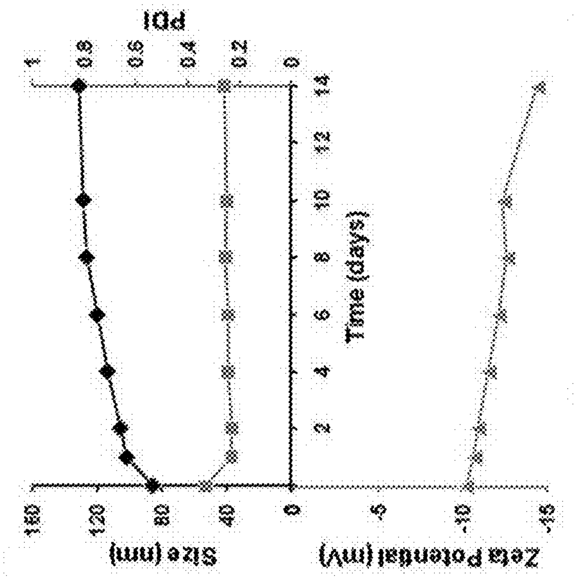
FIG. 2B. DLS measurements of the size, polydispersity index (PDI), and surface zeta potential of the nanoparticles over 14 days.
Figure 2A:
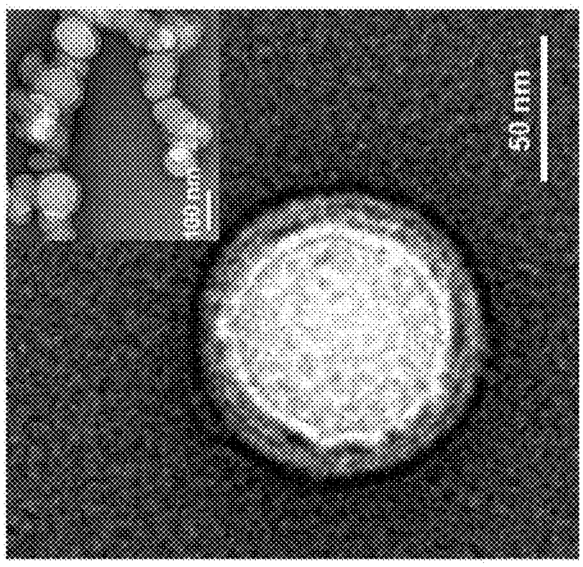
FIG. 2A. The nanoparticles were negatively stained with uranyl acetate and subsequently visualized with TEM.

To characterize the RBC membrane-coated PLGA nanoparticles, the particles were first negatively stained with uranyl acetate and then visualized using transmission electron microscopy (TEM) (FIG. 2A). The resulting image reveals a core-shell structure as expected in a lipid bilayer-coated polymeric particle. The particle size is ~80 nm and matches the hydrodynamic diameter measured by dynamic light scattering (DLS). Closer examination reveals a polymeric core approximately 70 nm in diameter and an outer lipid shell 7~8 nm in thickness. The thickness of the lipid layer is in agreement with the reported membrane width of RBCs (16), suggesting a successful membrane translocation to the polymeric particle surface.

Figure 2C:
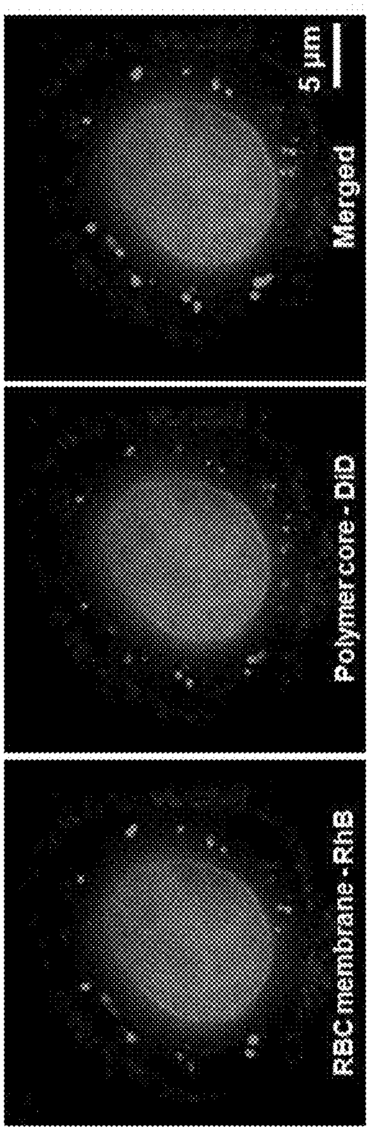
FIG. 2C. Scanning fluorescence microscopy images demonstrated the co-localization of the RBC membranes (visualized with green rhodamine-DMPE dyes) and polymeric cores (visualized with red DiD dyes) after being internalized by HeLa cells. The RBC membrane-coated nanoparticles were incubated with HeLa cells for 6 hours. The excess nanoparticles were washed out and the cells were subsequently fixed for imaging.

To examine the long-term stability of the resulting RBC-mimicking nanoparticles, they were suspended in 1×PBS at a concentration of 1 mg/mL and then monitored by DLS for the particle size, the polydispersity index (PDI), and the zeta potential (FIG. 2B). Over a span of two weeks the particle size increased from 85 to 130 nm, the zeta potential decreased from −10.2 to −12.7 mV, and the PDI remained relatively the same at 0.26. The changes in size and zeta potential are likely caused by the fusion of small amount of excess vesicles in the particle solution. To verify the integrity of the core-shell particle structure, hydrophobic DiD fluorophore (excitation/emission=644 nm/655 nm) and the lipophilic rhodamine-DMPE dye (excitation/emission=557 nm/571 nm) were loaded into the polymeric core and the RBC membrane-derived vesicles, respectively, prior to the vesicle-particle fusion. The resulting dual-fluorophore labeled nanoparticles were incubated with Hela cells for 6 hours and visualized using fluorescence microscopy. In FIG. 2C, DiD (red) and rhodamine-DMPE (green), each of which corresponds to a different particle compartment, overlap in the same locations. This fluorescence co-localization indicates an intact core-shell structure of the nanoparticles after they are internalized by the cells.

Figure 3B:
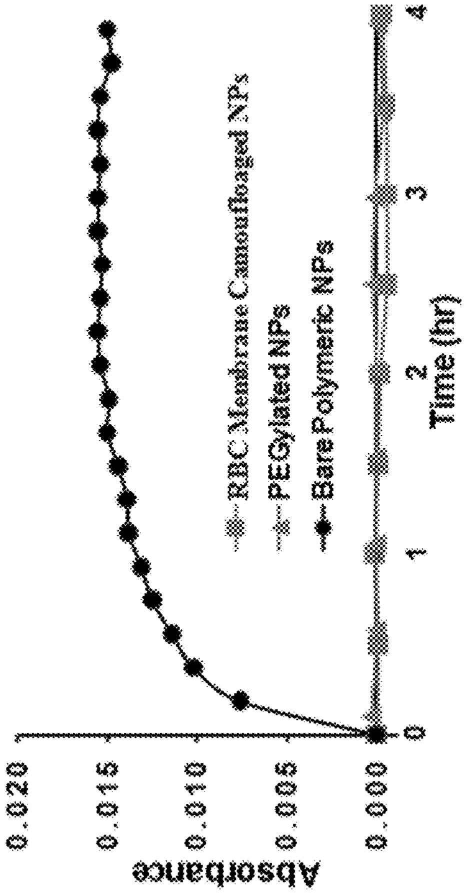
FIG. 3B. RBC membrane-coated PLGA nanoparticles, PEG-coated lipid-PLGA hybrid nanoparticles, and bare PLGA nanoparticles were incubated in 100% fetal bovine serum and monitored for absorbance at 560 nm for 4 hours.

Following the structural studies, the particles were examined for their protein contents. The RBC membrane-coated nanoparticles were dialyzed with 30 nm porous membranes for 24 hours to remove unbound proteins and subsequently treated with sodium dodecyl sulfate (SDS) to solubilize the membrane proteins. Samples of emptied RBCs and RBC membrane-derived vesicles were prepared in parallel as a comparison. Protein separation by polyacrylamide gel electrophoresis (PAGE) indicates that the composition of membrane proteins were mostly retained throughout the particle synthesis and can be identified on the RBC membrane-coated PLGA nanoparticles (FIG. 3A). This finding suggests that the translocation of the bilayered cellular membranes also transfers the associated membrane proteins to the nanoparticle surface. Since the solid PLGA core precludes protein entries and unbound proteins are filtered out by dialysis, the detected membrane proteins are most likely anchored in the bilayered lipid membranes that surround the nanoparticles. The resulting protein-containing lipid membrane-coated particles can be likened to a well-studied polymer-supported planer lipid bilayer model, which has been shown to retain the functionalities of membrane-associated proteins (15). Minor alteration in the protein makeup, however, was observed as a band near 51 kDa is noticeably fainter. The faint band likely corresponds to peripheral membrane proteins associated with spectrin cytoskeletal proteins, which are lost during the mechanical extrusion for the vesicle-particle fusion as can be observed by the missing band at ~200 kDa.

The inventors then determined the serum stability and the in vivo circulation half-life of the RBC membrane-coated nanoparticles. To put the results into perspective, similarly sized bare PLGA nanoparticles (~75 nm) and structurally analogous PEG (Mw 2000)-functionalized lipid-polymer hybrid nanoparticles (~80 nm) were used as negative and positive controls respectively. For the serum stability test, a previously cited absorbance method was used to monitor the particle size change in the presence of fetal bovine serum (FBS) (17, 18). Since larger particles induce higher light scattering, aggregation of unstable particles can be observed by monitoring the increase in the absorbance value. Each type of the nanoparticles were suspended in 100% FBS with a final nanoparticle concentration of 1 mg/mL. All samples were incubated at 37° C. and shaked gently prior to each absorbance measurement. The absorbance values measured at 560 nm suggest that the RBC-membrane coated nanoparticles have equivalent serum stability as the PEG-functionalized lipid-polymer hybrid nanoparticles as neither sample showed any observable change in absorbance within 4 hours (FIG. 3B). In contrast, the bare PLGA nanoparticles showed little stability as they immediately aggregated upon mixture with the serum solution.

To study the systemic circulation time of the each type of nanoparticles, the inventors loaded the hydrophobic DiD fluorescent dye to all three types of nanoparticles. The dye shows minimal release (<20% in 72 hours) and has been widely cited as a marker for the circulation studies of nanoparticles (19, 20). For each particle type, 150 μL of 3 mg/ml DiD-loaded nanoparticles were injected into a group of 6 mice through tail-vein injection. To avoid the immune responses associated with different blood types, the mice subject to the circulation studies are of the same strain from which the RBCs are collected to prepare the nanoparticles. At various time points following the injection, 20 μL blood were collected from the eye socket of the mice for fluorescence measurements.

Figure 3C:
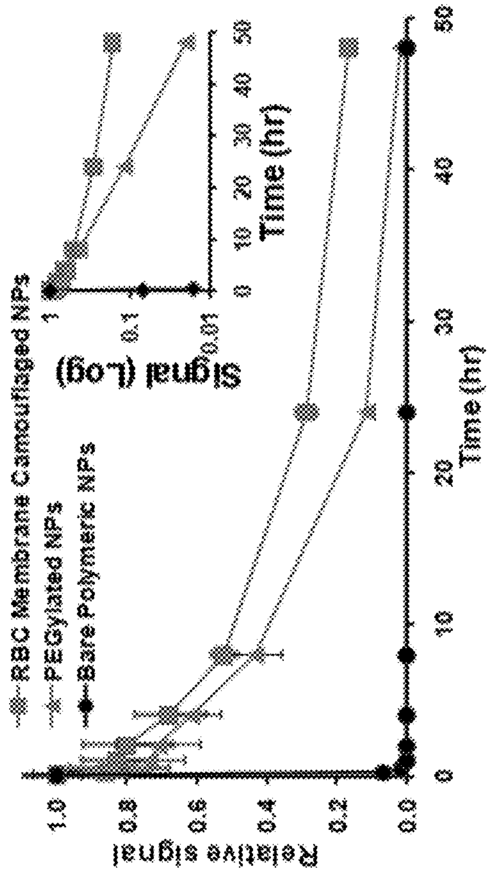
FIG. 3C. DiD-loaded nanoparticles were injected intravenously through the tail vein of mice. At various time points blood was withdrawn intraorbitally and measured for fluorescence at 670 nm to evaluate the systemic circulation lifetime of the nanoparticles (n=6 per group).
Figure 3A:
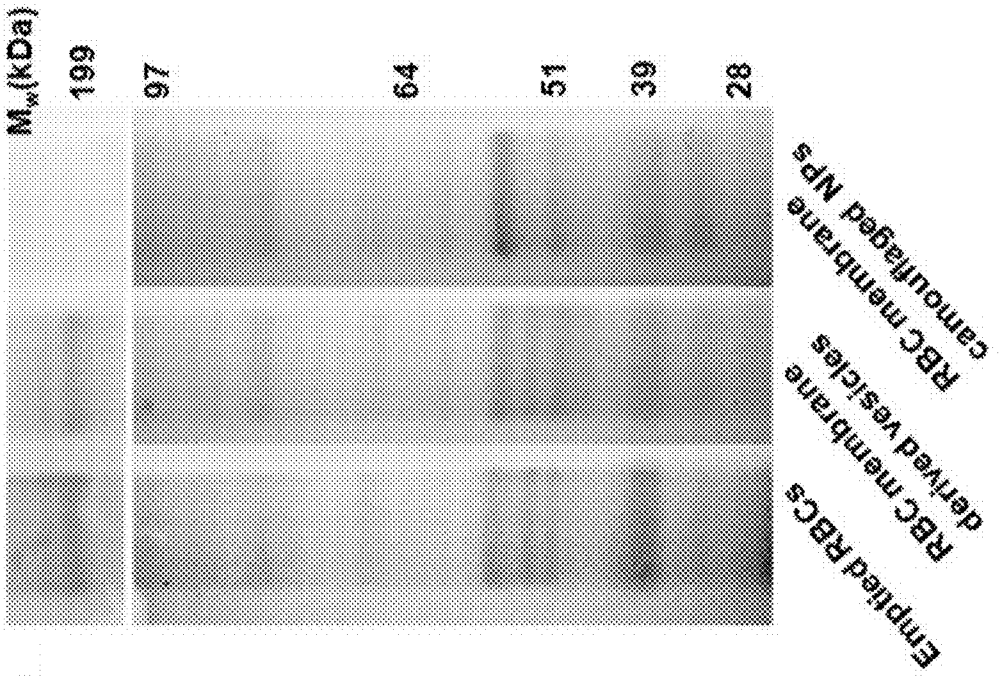
FIG. 3A. Proteins in emptied RBCs, RBC membrane-derived vesicles, and purified RBC membrane-coated PLGA nanoparticles were solubilized and resolved on a polyacrylamide gel.

FIG. 3C shows that the RBC membrane-coated nanoparticles had superior blood retention to the PEG-functionalized nanoparticles. At 24 and 48 hour marks, the RBC membrane-coated nanoparticles exhibited 29% and 16% overall retention respectively as compared to the 11% and 2% exhibited by the PEG-coated nanoparticles. The bare PLGA nanoparticles, on the other hand, showed negligible signal in the first blood withdrawal at the 2 minute mark, which was expected based on their rapid aggregations in serum. The semi-log plot in the inset of FIG. 3C better illustrates the difference in the pharmacokinetic profiles as circulation half-life can be derived from the slope of the semi-log signals. Based on a two-compartment model that has been applied in previous studies to fit the circulation results of nanoparticles (21, 22), the elimination half-life was calculated as 39.6 hours for the RBC membrane-coated nanoparticles and 15.8 hours for the PEG-coated nanoparticles.

Alternatively, the circulation data in FIG. 3C can be interpreted through a one-way non-linear clearance model, where the causes of nanoparticle clearance (i.e. availability of clearing sites and opsonin proteins) are continuously depleted to give rise to a slowing particle uptake. Simberg et al. have reported that by injecting "decoy" particles prior to the injection of primary particles, the circulation half-life of the primary particles can be prolonged by nearly 5-fold (23). It is reasonable to expect that the saturation of the RES system can retard additional particle uptake and account for a non-linear particle elimination rate. Based on this non-linear elimination model, the first apparent half-life (i.e., 50% of the particles are cleared) is 9.6 hours for the RBC membrane-coated nanoparticles and 6.5 hours for the PEG-coated nanoparticles. Regardless of the pharmacokinetic models, the RBC membrane-coated nanoparticles have longer elimination half-life, which suggests that the RBC membrane coating is superior in retarding in vivo clearance compared to the conventional PEG stealth coating. This finding further confirms that the nanoparticles were modified with the functional components on the RBC membranes, which contain immunosuppressive proteins that inhibit macrophage uptake (24). Since these membrane proteins are from the natural RBCs collected from the host blood, they are expected to stimulate negligible immune response after they are translocated to the surface of polymeric nanoparticles. With the TEM visualization, the SDS-PAGE results, and the circulation half-life study, the inventors demonstrate the transfer of cell membranes and the corresponding functional surface proteins for nanoparticle functionalization using the reported technique.

Figure 4A:
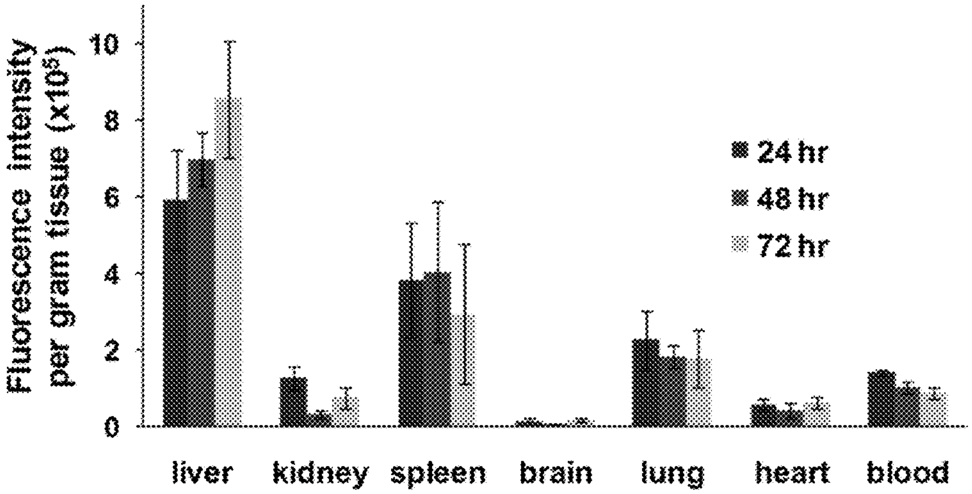
FIG. 4A. Fluorescence intensity per gram of tissue (n=6 per group).

The inventors then determined the in vivo tissue distribution of the RBC membrane-coated nanoparticles to further evaluate their potential as a delivery vehicle. For the biodistribution study, 18 mice received an injection of 150 μL of 3 mg/mL DiD-loaded nanoparticles through the tail vein. At each of the 24, 48, and 72 hour time points following the particle injection, 6 mice were euthanized and their liver, kidney, spleen, brain, lung, heart and blood were collected. For fluorescence quantification, the organs collected at different time points were washed, weighed, homogenized in 1 mL PBS, and then measured by a fluorospectrometer. FIG. 4A shows the nanoparticle content per gram of tissue. The two primary organs of the RES system, liver and spleen, contained the highest amount of nanoparticles. However, significant fluorescent level was also observed in the blood at the 3 time points.

Figure 4B:
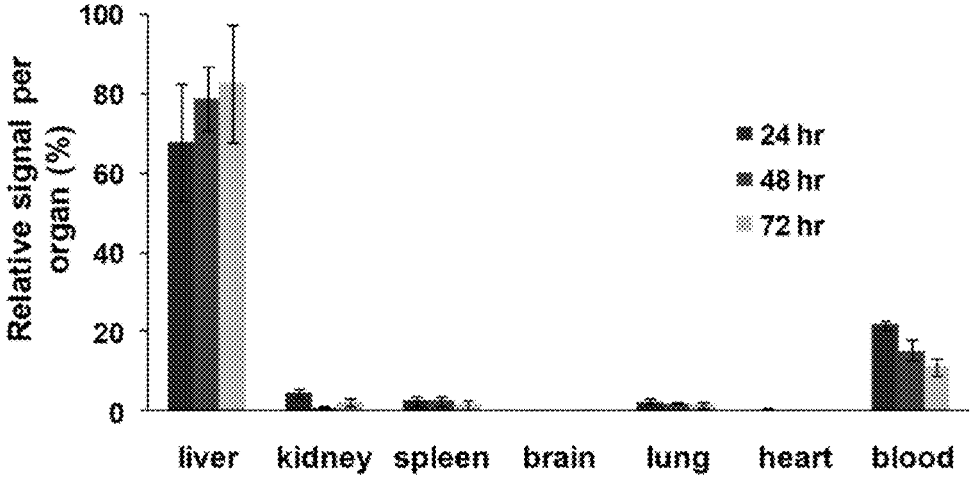
FIG. 4B. Relative signal per organ.

To better understand the overall particle distribution, the fluorescence signals were multiplied by the measured weight of the corresponding organs, with the weight of the blood being estimated as 6% of the total body weight. FIG. 4B shows relative signal in each organ normalized to the total fluorescence. After accounting for the tissue mass, it can be observed that the nanoparticles are distributed mainly in the blood and the liver. The fluorescence signals from the blood correlate well with the data from the circulation half-life study, with 21%, 15%, and 11% of nanoparticle retention at 24, 48, and 72 hour marks respectively. Also, as the blood fluorescence decreased, a corresponding increase in signal was observed in the liver, which indicates that the source of the fluorescence in the blood was eventually taken up by the RES system. This result validates that the observed blood fluorescence came from the long-circulating nanoparticles rather than leakage of the dye, which would be secreted by the kidneys and result in a reduction in the signal intensity from the liver. It is worth noting that the RBC membrane-coated polymeric nanoparticles have a significantly longer circulation time compared to previously reported RBC-derived liposomes, which are cleared from the blood circulation in less than 30 minutes (13). This prolonged circulation time by the RBC membrane-coated nanoparticles can be attributed to the higher structural rigidity, better particle stability, and the more reliable cargo/dye encapsulation. As compared to other published data on nanoparticle circulations in mice models (14, 25, 26), most of which show negligible blood retention after 24 hours, the RBC membrane-coated nanoparticles exhibit superior in vivo residence time and hold tremendous potentials for biomedical applications as a robust delivery platform.

The erythrocyte membrane-coated nanoparticles reported herein are structurally analogous to the commonly cited lipid-polymer hybrid nanoparticles, which are quickly emerging as a promising multi-functional drug delivery platform that contains the desirable characteristics of both liposomes and polymeric nanoparticles (27, 28). Lipid-polymer hybrid nanoparticles have shown a more sustained drug release profile compared to polymeric nanoparticles with similar size owing to the diffusional barrier provided by the lipid monolayer coating. The drug release kinetics from the RBC membrane-coated nanoparticles is expected to be even more gradual because the RBC membrane provides a more dense and bilayered lipid barrier against drug diffusion. The membrane coating approach in this study can also be extended to other nanostructures as the versatility of lipid coating has made its way to silica nanoparticles and quantum dots (29-31). Further particle functionalization can be achieved by inserting modified lipids, lipid derivatives, or transmembrane proteins to the lipid membranes prior to the preparation of the RBC membrane-coated nanostructures.

Regarding the translation of these RBC membrane-coated nanoparticles as a clinical drug delivery vehicle, many challenges and opportunities lie ahead. Unlike in animal studies human erythrocytes contain numerous surface antigens that can be classified to many different blood groups. To optimize the particles for long-circulating drug delivery, the particles need to be cross-matched to patients' blood as in the case of blood transfusion. For more versatile applications to broad populations of patients, the particles can be selectively depleted of those immunogenic proteins during the synthesis steps. Alternatively, this biomimetic delivery platform could be an elegant method for personalized medicine whereby the drug delivery nanocarrier is tailored to individual patients with little risk of immunogenicity by using their own RBC membranes as the particle coatings.

In conclusion, the inventors demonstrate the synthesis of an erythrocyte membrane-camouflaged polymeric nanoparticle for long-circulating cargo delivery. The adopted technique provides fabricate cell-mimicking nanoparticles through a top-down approach which bypasses the labor-intensive processes of protein identifications, purifications, and conjugations. The proposed method also provides a bilayered medium for transmembrane protein anchorage and avoids chemical modifications which could compromise the integrity and functionalities of target proteins. The inventors demonstrate that the lipid layer can be derived directly from live cells. The translocation of natural cellular membranes and their associated functionalities to the particle surface represents a unique and robust top-down approach in nanoparticle functionalization.

Materials and Methods

Figure 5:
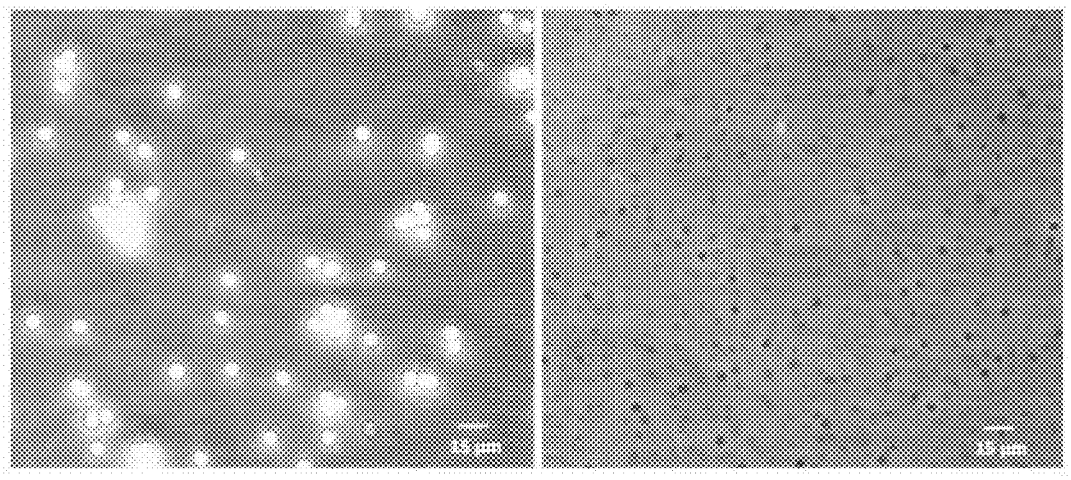
FIG. 5. Phase contrast microscopy images of mouse red blood cells (RBCs) before (left panel) and after (right panel) hemolytic treatment in hypotonic solution. Deprivation of RBC interior contents (hemoglobins) was verified by the change in phase contrast, which indicates an alteration of the medium inside the RBCs.

Red blood cell (RBC) ghost derivation. RBC ghosts devoid of cytoplasmic contents were prepared following previously published protocols with modifications (32). Whole blood was first withdrawn from male ICR mice (6-8 wks) obtained from Charles River Laboratories (Wilmington, MA) through cardiac puncture using a syringe containing a drop of heparin solution (Cole-Parmer, Vernon Hills, IL). The whole blood was then centrifuged at 2000 rpm for 5 minutes at 4° C., following which the serum and the buffy coat were carefully removed. The resulting packed RBCs were washed in ice cold 1×PBS prior to hypotonic medium treatment for hemolysis. The washed RBCs were suspended in 0.25×PBS in an ice bath for 20 minutes and were centrifuged at 2000 rpm for 5 minutes. The hemoglobin was removed whereas the pink pellet was collected. The resulting RBC ghosts were verified using phase contrast microscopy, which revealed an intact cellular structure with an altered cellular content (FIG. 5).

Figure 6:
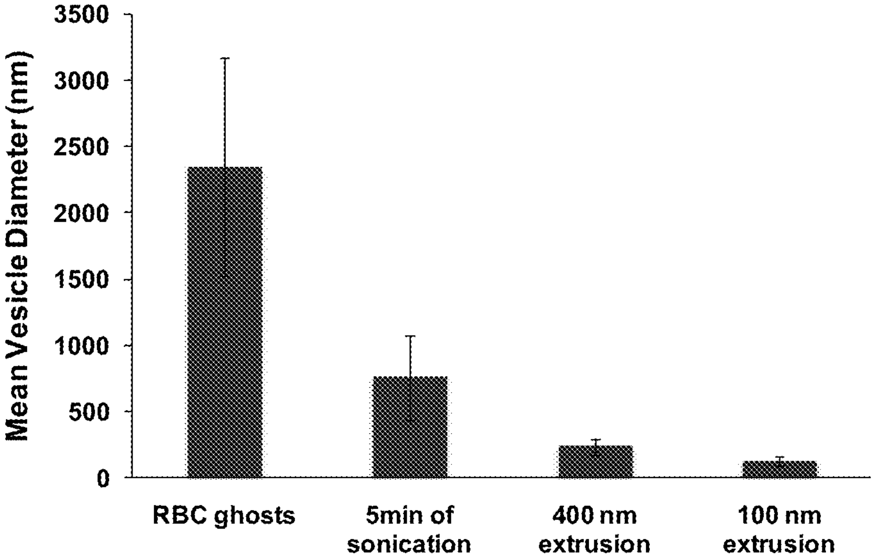
FIG. 6. The average diameter of the RBC membrane-derived vesicles following RBC ghosts derivation, 5 min of sonication, 400 nm extrusion, and 100 nm extrusion as measured by dynamic light scattering (DLS).

Preparation of RBC membrane-derived vesicles. The collected RBC ghosts were sonicated in a capped glass vial for 5 minutes using a FS30D bath sonicator (Fisher Scientific, Pittsburgh, PA) at a frequency of 42 kHz and power of 100 W. The resulting vesicles were subsequently extruded serially through 400 nm and then 100 nm polycarbonate porous membranes using an Avanti mini extruder (Avanti Polar Lipids, Alabaster, AL). To visualize the liposomal compartment in the RBC membrane-derived vesicles, 1 mL of whole blood was mixed with 20 ug of 1,2-Dimyristoyl-sn-Glycero-3-Phosphoethanolamine-N-(Lissamine Rhodamine B Sulfonyl) (Ammonium Salt) (DMPE-RhB) (Avanti Polar Lipids, Alabaster, AL) during the vesicle preparation process. The size of the RBC membrane-derived vesicles was measured by dynamic light scattering (DLS) after each preparation step (FIG. 6).

Figure 7:
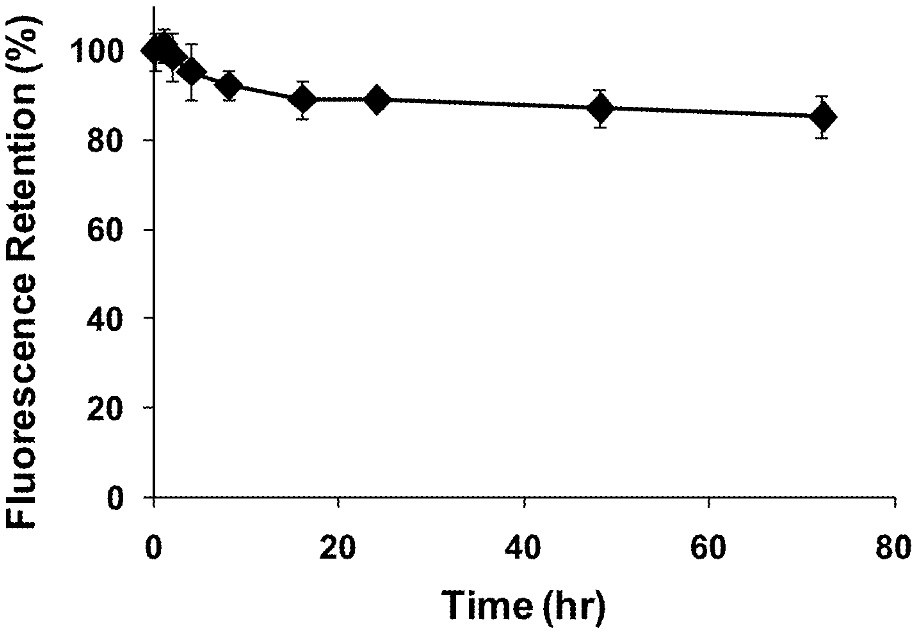
FIG. 7. The fluorescence retention of DiD dye in PEGylated lipid-PLGA hybrid nanoparticles (NPs) over a period of 72 hours.

Preparation of PLGA nanoparticles. The PLGA polymeric cores were prepared using 0.67 dL/g carboxy-terminated 50:50 poly(DL-lactide-co-glycolide) (LACTEL Absorbable Polymers, Cupertino, CA) in a solvent displacement process. The PLGA polymer was first dissolved in acetone at a 1 mg/mL concentration. To make 1 mg of PLGA nanoparticles, 1 mL of the solution was added dropwise to 3 mL of water. The mixture was then stirred in open air for 2 hours. The resulting nanoparticle solution was filtered with 10K MWCO Amicon Ultra-4 Centrifugal Filters (Millipore, Billerica, MA) and resuspended in 1 mL PBS (1×, pH=7.4). For fluorescence microscopy imaging and in vivo particle tracking purposes, 2 μg of 1,1'-dioctadecyl-3,3,3',3'-tetramethylindodicarbocyanine, 4-chlorobenzenesulfonate salt (DiD) dye (Invitrogen, Carlsbad, CA) were added to the PLGA acetone solution prior to PLGA nanoparticle synthesis. The release of DiD dye from PLGA nanoparticles was examined using a dialysis method in which 100 μL of the prepared nanoparticle solutions were loaded into a Slide-A-Lyzer MINI dialysis microtube with a molecular weight cutoff of 3.5 kDa (Pierce, Rockford, IL). The nanoparticles were dialyzed in PBS buffer at 37° C. The PBS solution was changed every 12 hours during the dialysis process. At each predetermined time point, nanoparticle solutions from three mini dialysis units were collected separately for dye quantification using an Infinite M200 multiplate reader (TeCan, Switzerland) (FIG. 7). As a control particle, the PEG-coated lipid-PLGA hybrid nanoparticles were prepared through a nanoprecipitation method.

Tissue culture and nanoparticle endocytosis. The human epithelial carcinoma cell line (HeLa) was maintained in RPMI (Gibco BRL, Grand Island, NY) supplemented with 10% fetal bovine albumin, penicillin/streptomycin (Gibco-BRL), L-glutamine (Gibco-BRL), MEM nonessential amino acids (Gibco-BRL), sodium bicarbonate (Cellgro, Herndon, VA), and sodium pyruvate (Gibco-BRL). The cells were cultured at 37° C. with 5% $CO_2$ and were plated in chamber slides (Cab-Tek II, eight wells; Nunc, Rochester, NY) with the aforementioned media. On the day of experiment, cells were washed with pre-warmed PBS and incubated with pre-warmed RPMI media for 30 minutes before adding 100 μg of DMPE-RhB and DiD labeled RBC membrane-coated PLGA nanoparticles. The nanoparticles were incubated with cells for 4 hours at 37° C. The cells were then washed with PBS 3 times, fixed with tissue fixative (Millipore, Billerica, MA) for 30 minutes at room temperature, stained with 4',6-diamidino-2-phenylindole (DAPI, nucleus staining), mounted in ProLong Gold antifade reagent (Invitrogen), and imaged using a deconvolution scanning fluorescence microscope (DeltaVision System, Applied Precision, Issaquah, WA). Digital images of blue, green, and red fluorescence were acquired under DAPI, FITC, and CY5 filters respectively using a 100× oil immersion objective. Images were overlaid and deconvoluted using soft WoRx software.

Figure 8:
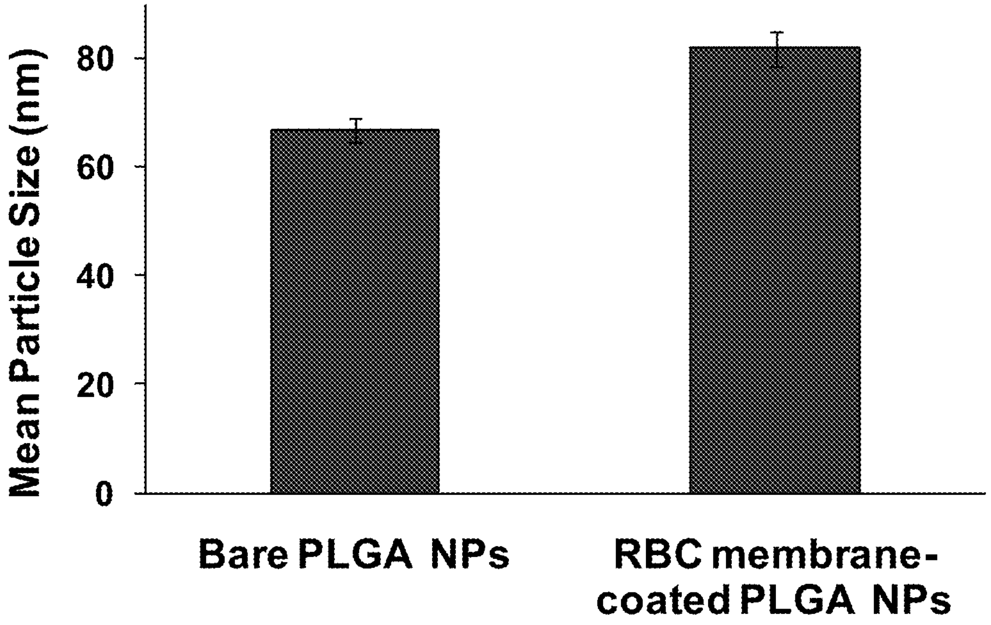
FIG. 8. The mean particle diameter of PLGA nanoparticles (NPs) prior to (left) and following (right) RBC membrane coating as measured by DLS.

Fusion of RBC membrane-derived vesicles with PLGA nanoparticles. To fuse the RBC membrane-derived vesicles with the PLGA nanoparticles, 1 mg of PLGA nanoparticles was mixed with RBC membrane-derived vesicles prepared from 1 mL of whole blood and then extruded 7 times through a 100 nm polycarbonate porous membrane using an Avanti mini extruder. The mixture ratio was estimated based on the membrane volume of RBCs and the total membrane volume required to fully coat 1 mg of PLGA nanoparticles. Parameters used for the estimation include mean surface area of mouse RBCs (75 $\mu m^2$) (34), membrane thickness of RBC (7 nm), density of 50:50 PLGA nanoparticles (1.34 $g/cm^3$) (35), red blood cell concentration in mouse blood (7 billion per mL) (36), and the mean particle size as measured by DLS before and after the RBC membrane coating (FIG. 8). An excess of blood was used to compensate for the membrane loss during RBC ghost derivation and extrusion. The resulting RBC membrane-coated PLGA nanoparticles were dialyzed against 30 nm porous membranes (Avanti Polar Lipids) for 24 hours and concentrated through nitrogen purging. The particle size and polydispersity remained identical following dialysis and concentration.

Characterization of RBC membrane-coated PLGA nanoparticles. Nanoparticle size (diameter, nm), polydispersity, and surface charge (zeta potential, mV) were measured by DLS using Nano-ZS, model ZEN3600 (Malvern, U.K.). Nanoparticles (~500 μg) were suspended in 1×PBS (~1 mL) and measurements were performed in triplicate at room temperature for 2 weeks. Serum stability tests were conducted by suspending the nanoparticles in 100% fetal bovine serum (FBS) (Hyclone, Logan, UT) with a final nanoparticle concentration of 1 mg/mL. The particles were first concentrated to 2 mg/mL and a concentrated 2×FBS was then added at equal volume. Absorbance measurements were conducted using an Infinite M200 multiplate reader. Samples were incubated at 37° C. with light shaking prior to each measurement. The absorbance at 560 nm was taken approximately every 30 minutes over a period of 4 hours.

Transmission electron microscopy imaging. The structure of the RBC membrane-coated nanoparticles was examined using a transmission electron microscope. A drop of the nanoparticle solution at a concentration of 4 μg/mL was deposited onto a glow-discharged carbon-coated grid. Five minutes after the sample was deposited the grid was rinsed with 10 drops of distilled water. A drop of 1% uranyl acetate stain was added to the grid. The grid was subsequently dried and visualized using a FEI 200 KV Sphera microscope.

Protein characterization using SDS-PAGE. The RBC ghosts, the RBC membrane-derived vesicles, and the dialyzed RBC membrane coated PLGA nanoparticles were prepared in SDS sample buffer (Invitrogen). The samples were then run on a NuPAGE® Novex 4-12% Bis-Tris 10-well minigel in 3-(N-morpholino) propanesulfonic acid (MOPS) running buffer using NovexSureLockXcell Electrophoresis System (Invitrogen). The samples were run at 150 V for 1 hour, and the resulting polyacrylamide gel was stained in SimplyBlue (Invitrogen) overnight for visualization.

Pharmacokinetics and biodistribution studies. All the animal procedures complied with the guidelines of University of California San Diego Institutional Animal Care and Use Committee. The experiments were performed on male ICR mice (6-8 wks) from Charles River Laboratories (Wilmington, MA). To evaluate the circulation half-life of RBC membrane-coated nanoparticles, 150 μL of DiD-loaded nanoparticles were injected into the tail vein of the mice. 20 μL blood was collected at 1, 5, 15, 30 minutes, and 1, 2, 4, 8, 24, 48, and 72 hours following the injection. The same dose of DiD containing PEG-coated lipid-PLGA hybrid nanoparticles and bare PLGA nanoparticles were also tested in parallel as controls. Each particle group contained 6 mice. The collected blood samples were diluted with 30 μL PBS in a 96-well plate before fluorescence measurement. Pharmacokinetics parameters were calculated to fit a two-compartment model.

To study the biodistribution of the nanoparticles in various tissues, 18 mice received an injection of 150 μL of 3 mg/mL DiD-loaded nanoparticles through the tail vein. At each of the 24, 48, and 72 hour time points following the particle injection, 6 mice were randomly selected and euthanized. Their liver, kidney, spleen, brain, lung, heart and blood were collected. The collected organs were carefully weighed and then homogenized in 1 mL PBS. Total weight of blood was estimated as 6% of mouse body weight. The fluorescence intensity of each sample was determined by an Infinite M200 multiplate reader.

REFERENCES

1. Moghimi S M, Hunter A C, Murray J C (2001) Long-circulating and target-specific nanoparticles: theory to practice. *Pharmacol Rev* 53:283-318.
2. Davis M E, Chen Z G, Shin D M (2008) Nanoparticle therapeutics: an emerging treatment modality for cancer. *Nat Rev Drug Discov* 7:771-782.
3. Peer D, et al. (2007) Nanocarriers as an emerging platform for cancer therapy. *Nat Nanotechnol* 2:751-760.
4. Yoo J W, Chambers E, Mitragotri S (2010) Factors that control the circulation time of nanoparticles in blood: challenges, solutions and future prospects. *Curr Pharm Des* 16:2298-2307.
5. Geng Y, et al. (2007) Shape effects of filaments versus spherical particles in flow and drug delivery. *Nat Nanotechnol* 2:249-255.
6. Alexis F, Pridgen E, Molnar L K, Farokhzad O C (2008) Factors affecting the clearance and biodistribution of polymeric nanoparticles. *Mol Pharm* 5:505-515.
7. Knop K, Hoogenboom R, Fischer D, Schubert U S (2010) Poly(ethylene glycol) in drug delivery: pros and cons as well as potential alternatives. *Angew Chem Int Ed* 49:6288-6308.
8. Jiang S Y, Cao Z Q (2010) Ultralow-fouling, functionalizable, and hydrolyzable zwitterionic materials and their derivatives for biological applications. *Adv Mater* 22:920-932.
9. Yang W, Zhang L, Wang S, White A D, Jiang S (2009) Functionalizable and ultra stable nanoparticles coated with zwitterionic poly(carboxybetaine) in undiluted blood serum. *Biomaterials* 30:5617-5621.
10. Doshi N, Zahr A S, Bhaskar S, Lahann J, Mitragotri S (2009) Red blood cell-mimicking synthetic biomaterial particles. *Proc Natl Acad Sci USA* 106:21495-21499.
11. Tsai R K, Rodriguez P L, Discher D E (2010) Self inhibition of phagocytosis: the affinity of 'marker of self' CD47 for SIRPalpha dictates potency of inhibition but only at low expression levels. *Blood Cells Mol Dis* 45:67-74.
12. Merkel T J, et al. (2011) Using mechanobiological mimicry of red blood cells to extend circulation times of hydrogel microparticles. *Proc Natl Acad Sci USA* 108:586-591.

13. Desilets J, Lejeune A, Mercer J, Gicquaud C (2001) Nanoerythrosomes, a new derivative of erythrocyte ghost: IV. Fate of reinjected nanoerythrosomes. *Anticancer Res* 21:1741-1747.
14. Cheng J, et al. (2007) Formulation of functionalized PLGA-PEG nanoparticles for in vivo targeted drug delivery. *Biomaterials* 28:869-876.
15. Tanaka M, Sackmann E (2005) Polymer-supported membranes as models of the cell surface. *Nature* 437:656-663.
16. Hochmuth R M, Evans C A, Wiles H C, Mccown J T (1983) Mechanical measurement of red cell membrane thickness. *Science* 220:101-102.
17. Fang R H, Aryal S, Hu C M, Zhang L (2010) Quick synthesis of lipid-polymer hybrid nanoparticles with low polydispersity using a single-step sonication method. *Langmuir* 26:16958-16962.
18. Popielarski S R, Pun S H, Davis M E (2005) A nanoparticle-based model delivery system to guide the rational design of gene delivery to the liver. 1. Synthesis and characterization. *Bioconjug Chem* 16:1063-1070.
19. Goutayer M, et al. (2010) Tumor targeting of functionalized lipid nanoparticles: assessment by in vivo fluorescence imaging. *Eur J Pharm Biopharm* 75:137-147.
20. Xiao K, et al. (2009) A self-assembling nanoparticle for paclitaxel delivery in ovarian cancer. *Biomaterials* 30:6006-6016.
21. Gratton S E, et al. (2007) Nanofabricated particles for engineered drug therapies: a preliminary biodistribution study of PRINT nanoparticles. *J Control Release* 121:10-18.
22. Peracchia M T, et al. (1999) Stealth PEGylated polycyanoacrylate nanoparticles for intravenous administration and splenic targeting. *J Control Release* 60:121-128.
23. Simberg D, et al. (2007) Biomimetic amplification of nanoparticle homing to tumors. *Proc Natl Acad Sci USA* 104:932-936.
24. Oldenborg P A, et al. (2000) Role of CD47 as a marker of self on red blood cells. *Science* 288:2051-2054.
25. Gu F, et al. (2008) Precise engineering of targeted nanoparticles by using self-assembled biointegrated block copolymers. *Proc Natl Acad Sci USA* 105:2586-2591.
26. Avgoustakis K, et al. (2003) Effect of copolymer composition on the physicochemical characteristics, in vitro stability, and biodistribution of PLGA-mPEG nanoparticles. *Int J Pharm* 259:115-127.
27. Zhang L. (2010) Lipid-polymer hybrid nanoparticles: synthesis, characterization and applications. *Nano LIFE* 1:163-173.
28. Sengupta S, et al. (2005) Temporal targeting of tumour cells and neovasculature with a nanoscale delivery system. *Nature* 436:568-572.
29. Valencia P M, et al. (2010) Single-step assembly of homogenous lipid-polymeric and lipid-quantum dot nanoparticles enabled by microfluidic rapid mixing. *ACS Nano* 4:1671-1679.
30. Liu J, Stace-Naughton A, Jiang X, Brinker C J (2009) Porous nanoparticle supported lipid bilayers (protocells) as delivery vehicles. *J Am Chem Soc* 131:1354-1355.
31. van Schooneveld M M, et al. (2010) Imaging and quantifying the morphology of an organic-inorganic nanoparticle at the sub-nanometre level. *Nat Nanotechnol* 5:538-544.
32. Dodge J T, Mitchell C, Hanahan D J (1963) The preparation and chemical characteristics of hemoglobin-free ghosts of human erythrocytes. *Arch Biochem Biophys* 100:119-130.
33. Zhang L, et al. (2008) Self-assembled lipid-polymer hybrid nanoparticles: A robust drug delivery platform. *ACS Nano* 2:1696-1702.
34. Waugh R E, Sarelius I H (1996) Effects of lost surface area on red blood cells and red blood cell survival in mice. Am J Physiol 271:C1847-1852.
35. Arnold M M, Gorman E M, Schieber L J, Munson E J, Berkland C (2007) NanoCipro encapsulation in monodisperse large porous PLGA microparticles. *J Control Release* 121:100-109.
36. Jacobs R L, Alling D W, Cantrell W F (1963) An evaluation of antimalarial combinations against Plasmodium berghei in the mouse. *J Parasitol* 49:920-925.
37. Lund, R.; Leth-Larsen, R.; Jensen, O. N.; Ditzel, H. J., Efficient isolation and quantitative proteomic analysis of cancer cell plasma membrane proteins for identification of metastasis-associated cell surface markers. *J Proteome Res* 2009, 8 (6), 3078-3090.
38. Graham, J. M., Isolation of membranes from tissue culture cells. *Methods Mol Biol* 1993, 19, 97-108.
39. Vayro, S.; Kemp, R.; Beechey, R. B.; Shirazi-Beechey, S., Preparation and characterization of basolateral plasma-membrane vesicles from sheep parotid glands. Mechanisms of phosphate and D-glucose transport. *Biochem J* 1991, 279 (Pt 3), 843-848.
40. Navas, P.; Nowack, D. D.; Morre, D. J., Isolation of purified plasma membranes from cultured cells and hepatomas by two-phase partition and preparative free-flow electrophoresis. *Cancer Res* 1989, 49 (8), 2147-2156.
41. Henon, M.; Bedouin, A.; Polonovski, J., [Isolation, identification and characterization of a plasma membrane preparation of guinea pig macrophages]. *C R Acad Sci Hebd Seances Acad Sci D* 1977, 285 (1), 121-122.
42. Boone, C. W.; Ford, L. E.; Bond, H. E.; Stuart, D. C.; Lorenz, D., Isolation of plasma membrane fragments from HeLa cells. *J Cell Biol* 1969, 41 (2), 378-392.

Example 2

Erythrocyte Membrane-Cloaked Polymeric Nanoparticles for Controlled Drug Loading and Release Polymeric nanoparticles (NPs) cloaked by red blood cell membrane (RBCm) confer combined advantages of long circulation lifetime and controlled drug retention and releases. Toward the development of this cell-mimicking NP platform for advanced drug delivery applications, herein, the inventor carried out studies to gain better understandings on its drug loading, drug release kinetics, and cell-based efficacy. Specifically, to study drug releases from RBCm-cloaked NPs, the inventor compared two strategies for loading doxorubicin (DOX), a model anti-cancer drug, into RBCm-cloaked NPs: physical encapsulation and chemical conjugation. In vitro efficacy was examined by using acute myeloid leukemia (AML) Kasumi-1 cell line.

The inventors found that chemical conjugation strategy resulted in a more sustained drug release profile. Furthermore, by formulating PEGylated NPs of the same polymeric cores as RBCm-cloaked NPs but different surface coatings, the inventors demonstrated that the RBCm cloak provided a barrier retarding the outward diffusion of encapsulated drug molecules. Efficacy study on AML Kasumi-1 cell line, RBCm-cloaked NPs exhibited higher toxicity in comparison to free DOX. These results indicate that the RBCm-cloaked NPs are a valuable delivery platform for controlled and sustained delivery of therapeutic agents for the treatment of various diseases such as blood cancers.

Introduction

In the past decades, advances in engineering materials at the nanometer scale have resulted in a myriad of nanoparticle (NP)-based drug delivery systems in clinical applications [1, 2]. The unique advantages of these nanomedicines, particularly their improvement on existing therapeutic agents through altered pharmacokinetics and biodistribution profiles, hinge on their ability to circulate in the blood stream for a prolonged period of time [3, 4]. As a result, considerable research interest has been focused on the search of novel materials, both naturally and synthetically made, that allow NPs to bypass macrophage uptake and systemic clearance [5, 6]. Meanwhile, strategies aimed at extending particle residence time in vivo through modifying NP physicochemical properties including size, shape, deformity, and surface characteristics have also been extensively explored [7, 8].

In this perspective, the inventor recently developed a red blood cell membrane (RBCm)-cloaked NP drug delivery system with combined advantages of a long circulation lifetime from RBCs and controlled drug retention and releases from polymeric particles [9]. The top-down approach, based on the extrusion of polymeric particles mixed with preformed RBCm-derived vesicles, translocated the entire RBCm with preserved membrane proteins to the surface of sub-100-nm polymeric cores, resulting in NPs cloaked by the erythrocyte exterior for long systemic circulation. This cell-mimicking strategy provides a cellular membrane medium surrounding polymeric cores for transmembrane protein anchorage, hence avoiding chemical modifications in conventional NP surface fictionalizations that could compromise the integrity and functionalities of the proteins.

In the continuing efforts to further develop this cell-mimicking NP platform for advanced drug delivery applications, herein, the inventors report formulation strategies of loading small-molecule chemotherapy drugs such as doxorubicin (DOX), a model anti-cancer drug, into the NPs and study drug release kinetics with an emphasis on the role played by RBCm cloak in drug retention. Specifically, to load DOX molecules into NP core, the inventors explored two distinct strategies: physically encapsulating drug molecules into the polymer matrix and chemically conjugating drug molecules to the polymer backbones, and showed that they resulted in distinct drug loading yields and release kinetics. The inventors further formulated NPs with the same polymer cores as RBCm-cloaked NPs, but coated by poly(ethylene glycol) (PEG, PEGylated NPs) rather than RBCm. Comparison of drug release profiles of the two delivery systems demonstrated that RBCm cloak provides a barrier retarding the outward diffusion of encapsulated drug molecules, and therefore can be potentially exploited to better control drug releases. Additionally, in examining the therapeutic potential of the RBCm-cloaked NPs, the inventors chose an acute myeloid leukemia (AML) Kasumi-1 cell line and showed that DOX-loaded RBCm-cloaked NPs exhibited higher toxicity in comparison to the same amount of free DOX.

Materials and Methods 2.1. RBC Ghost Derivation

RBC ghosts devoid of cytoplasmic contents were prepared following previously published protocols [9, 10]. Briefly, whole blood, withdrawn from male ICR mice (6-8 weeks, Charles River Laboratories) through cardiac puncture with a syringe containing a drop of heparin solution (Cole-Parmer), was centrifuged (800× g for 5 min at 4° C.) to remove serum and buffy coat. The packed RBCs were washed in ice cold 1×PBS, treated by hypotonic medium for hemolysis, and then suspended in 0.25×PBS in an ice bath for 20 min. The hemoglobin was removed by centrifuging the suspension at 800×g for 5 min. RBC ghosts in the form of a pink pellet were collected.

2.2. Preparation of RBCm-Derived Vesicles

The collected RBC ghosts were sonicated in a capped glass vial for 5 min using a FS30D bath sonicator (Fisher Scientific) at a frequency of 42 kHz and power of 100 W. The resulting vesicles were subsequently extruded repeatedly through 400 nm and then 200 nm polycarbonate porous membranes by using an Avanti mini extruder (Avanti Polar Lipids). After each extrusion, the size of the RBCm-derived vesicles was monitored by dynamic light scattering (DLS, Nano-ZS, model ZEN3600).

2.3. Ring-Opening Polymerization of L-Lactide

DOX-poly(lactide acid) (PLA) conjugates were synthesized based on a published protocol [11, 12]. Briefly, ring-opening polymerization of L-lactide (Sigma-Aldrich, USA) was catalyzed by an alkoxy complex (BDI)ZnN$(SiMe_3)_2$ in a glove-box filled with argon at room temperature. (BDI) ZnN$(SiMe_3)_2$ (6.4 mg, 0.01 mmol) and DOX (Jinan Wedo Co., Ltd., Jinan, China) (5.4 mg, 0.01 mmol) were mixed in anhydrous tetrahydrofuran (THF, 0.5 mL), where L-lactide (101 mg, 0.7 mmol) dissolved in 2 mL of anhydrous THF was added dropwise. After the L-lactide was completely consumed as indicated by $^1$H NMR (Varian Mercury 400 MHZ spectrometer), the crude product was precipitated in cold diethyl ether and purified by multiple dissolution-precipitation cycles. The conjugation was confirmed by $^1$H NMR and conjugates had a molecular weight of ~10,000 g/mol determined by gel permeation chromatography (GPC, Viscotek, USA).

2.4. Preparation of NP Core and Loading of DOX

The DOX-PLA conjugate was first dissolved in acetonitrile to form 1 mg/ml solution and 1 mL of such solution was added dropwise to 3 mL of water. The mixture was then stirred in open air for 2 hours, allowing acetonitrile to evaporate. The resulting solution of NP cores was filtered by Amicon Ultra-4 Centrifugal Filters (Millipore, 10 kDa cut-off) and then resuspended in 1 mL distilled water. To physically encapsulate DOX, 1 mg poly(lactic-co-glycolic acid) (PLGA, 0.67 dL/g, carboxy-terminated, LACTEL Absorbable Polymers) was first dissolved into 1 mL acetonitrile, followed by the addition of DOX pre-dissolved in 25 µL of dimethyl sulfoxide (DMSO). Similar procedures as described above were followed to generate suspensions containing NP cores.

2.5. Fusion of RBCm-Derived Vesicles with NP Cores

To fuse the RBCm-derived vesicles with the aforementioned NP cores, suspensions containing 1 mg of NP cores was first mixed with RBCm-derived vesicles prepared from 1 mL of whole blood. The mixture was then extruded 11 times through a 100-nm polycarbonate porous membrane with an Avanti mini extruder. To fully coat 1 mg of NP cores, an excess of blood was used to compensate for the membrane loss during RBC ghost derivation and extrusion [9].

2.6. Preparation of PEGylated NPs

The DOX-PLA conjugate and PLA-PEG-COOH (10 kDa, PDI=1.12) at a weight ratio of 1:1 was first dissolved in acetonitrile at a concentration of 1 mg/mL, followed by the same procedures as described above to produce NP suspensions. To physically encapsulate DOX into PEGylated NPs, 1 mg poly(lactic-co-glycolic acid) (PLGA, 0.67 dL/g, carboxy-terminated, LACTEL Absorbable Polymers) was first dissolved into 1 mL acetonitrile, followed by the addition of 100 μg DOX dissolved in 25 μL of DMSO. Same procedures as described above were used to produce NP suspensions.

2.7. NP Stability Studies

NP stability in PBS was assessed by monitoring particle size using DLS. Specifically, 500 μg NPs were suspended in 1 mL 1×PBS and the sizes were measured in triplicate at room temperature every 24 hours over a period of one week. Between measurements, samples were incubated at 37° ° C. with gentle shaking. NP serum stability was evaluated by monitoring the UV-absorbance at the wavelength of 560 nm. Specifically, NPs were first concentrated to 2 mg/ml in PBS, followed by the addition of 2× fetal bovine serum (FBS, Hyclone) of equal volume. The absorbance was measured by using an Infinite M200 multiplate reader at 37° C. approximately every 1 minute over a period of 2 hours.

2.8. Measurement of Drug Loading Yield and Releases

The concentration of DOX in a solution was determined by measuring florescence intensities at 580 nm with excitation wavelength of 480 nm. To determine DOX loading yield of NPs, the above fluorescent measurement was carried out after incubating 100 μL NP solution with 100 μL 0.1 M HCl in acetonitrile for 24 hours. To plot DOX release profiles, 200 μL NP solution (1 mg/mL) was loaded into a Slide-A-Lyzer MINI dialysis microtube (Pierce, Rockford, IL, molecular weight cutoff=3.5 kDa) and then dialyzed against 2 L of PBS (pH=7.4) at 37° C. PBS buffer was changed every 12 hours during the whole dialysis process. At each predetermined time point, NP solutions from three mini dialysis units were collected and DOX concentration was measured.

2.9. Cell Viability Assay

Cytotoxicity of free DOX and DOX-loaded NPs was assessed against Kasumi-1 cell line established from the peripheral blood of an acute myeloid leukemia (AML) patient using MTT assay (Promega Corporation, Madison, WI, USA). Cells were first seeded (~5× 103 per well) in 96-well plates and then incubated for 24 hours. After the addition of free DOX or DOX-loaded NPs, the cells were incubated for additional 72 hours. Cell viability was then determined by using MTT assay following a protocol provided by the manufacturer.

Results and Discussion 3.1. Preparation of RBCm-Cloaked NPs

Figure 9:
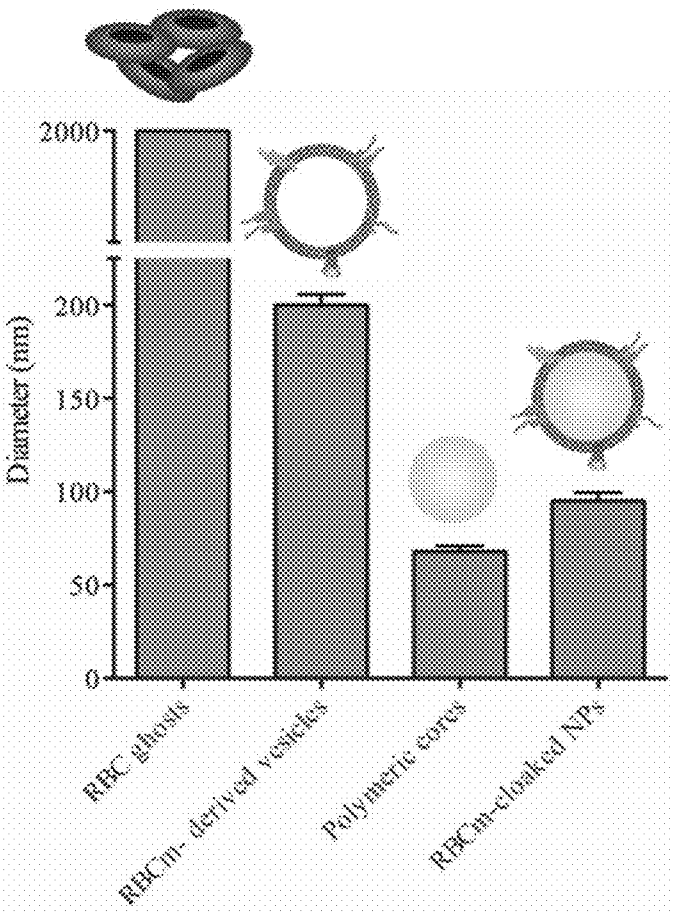
FIG. 9. Schematic illustration of building materials and the preparation process of RBCm-cloaked NPs. The hydrodynamic size of RBC ghosts, RBCm-derived vesicles, polymeric cores, and RBCm-cloaked NPs were measured by DLS.

The preparation process of RBCm-cloaked NPs was based on the previously published protocol and schematically illustrated in FIG. 9 [9]. Briefly, purified RBCs first underwent membrane rupture in a hypotonic environment to remove its intracellular contents. Next, the emptied RBCs (~2 μm in diameter) were washed and extruded through 100-nm porous membranes to create RBC-membrane derived vesicles (~200 nm in diameter). Meanwhile, polymeric cores (~70 nm in diameter), such as those made from PLA or PLGA, were prepared by using a solvent displacement method. The resulting polymeric cores were subsequently mixed with RBC-membrane derived vesicles and the mixture was physically extruded through 100-nm pores, where the two components fused under the mechanical force and formed RBCm-cloaked NPs (~90 nm in diameter).

3.2. Loading of Doxorubicin (DOX) into RBCm-Cloaked NPs

Figure 10:
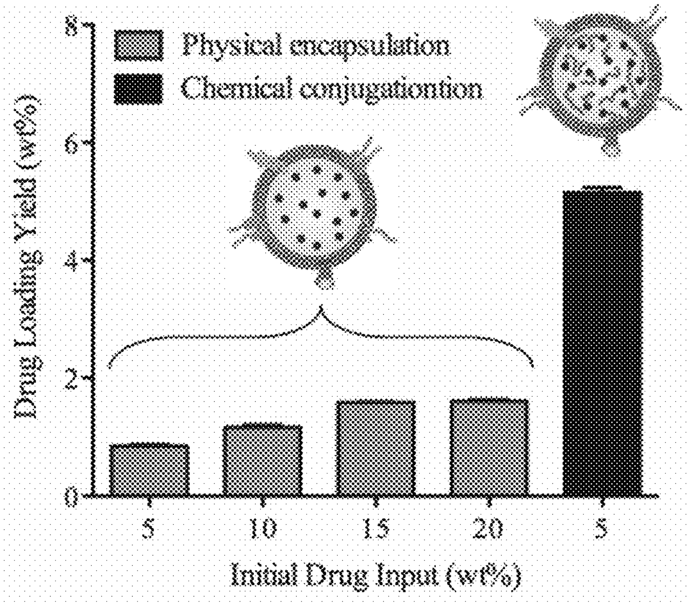
FIG. 10. Doxorubicin (DOX) loading yields in the RBCm-cloaked NPs at various initial drug inputs. Drug molecules were loaded into the NPs through two distinct loading mechanisms: physical encapsulation and chemical conjugation, respectively.

In this study, the inventors examined two distinct methods to load DOX as a model drug into the RBCm-cloaked NPs: physical encapsulation and chemical conjugation. Physical encapsulation is achieved by first mixing DOX and polymers in acetonitrile, followed by precipitation into water. In this case, drug loading yield can be varied through different formulation parameters. For example, when varying initial DOX to PLGA weight ratio from 5% to 20%, the loading yield increased from 0.9% to 1.8% (see FIG. 10).

Alternatively, DOX molecules can be loaded into NP cores by covalently conjugating drug molecules to polymer backbones. Intuitively, DOX molecules can be directly conjugated to carboxyl terminated PLA chains through hydroxyl groups; however, this approach causes heterogeneities for polymer-drug conjugates, owing largely to the polydispersity of the polymer chains, the lack of control over the regio- and chemoselective conjugation of the DOX molecules containing multiple hydroxyl groups, and the lack of control over the conjugation efficiency. Therefore, the inventors adopted an alternative approach, where the hydroxyl group of the DOX, with the presence of L-lactide monomer and $(BDI)ZnN(SiMe_3)_2$ as a catalyst, were utilized to initiate the ring opening polymerization (ROP) and led to the formation of PLA-DOX conjugates [11, 12]. In this approach, as the polymerization reaction is initiated by the drug molecule itself, a conjugation efficiency of near 100% can be achieved. In addition, the metal amido catalyst $(BDI)ZnN(SiMe_3)_2$ preferentially allows for PLA propagation at $C_{14}$—OH position of DOX instead of its more sterically hindered $C_4$'- and $C_9$—OH positions. After the reaction was terminated, products were purified by using repeated dissolution-precipitation cycles and then characterized by using $^1$H-NMR spectroscopy. Proton resonance peaks corresponding to both DOX molecules and PLA backbones are present, including the aromatic protons of DOX between δ=7.5 and 8.0 ppm, protons of —$CH_3$ group of PLA at δ=1.5 ppm, and —CH group of PLA at δ=5.2 ppm, hence confirming the formation of PLA-DOX conjugates [11].

In contrast to physical encapsulation, where the drug loading yield primarily depends on formulation parameters, in chemical conjugation, drug loading yield is dictated by polymer chain length, which is in turn determined by polymerization conditions such as initiator (DOX)-to-monomer ratio. For example, the PLA-DOX conjugates synthesized in our study were found to have a molecular weight of 10 kDa and a narrow polydispersity index (PDI) of 1.16, corresponding to an approximately 5% loading yield of DOX after the conjugates were formulated into the NPs (see FIG. 10).

3.3. In Vitro Stability of DOX-Loaded RBCm-Cloaked NPs

Figure 11A:
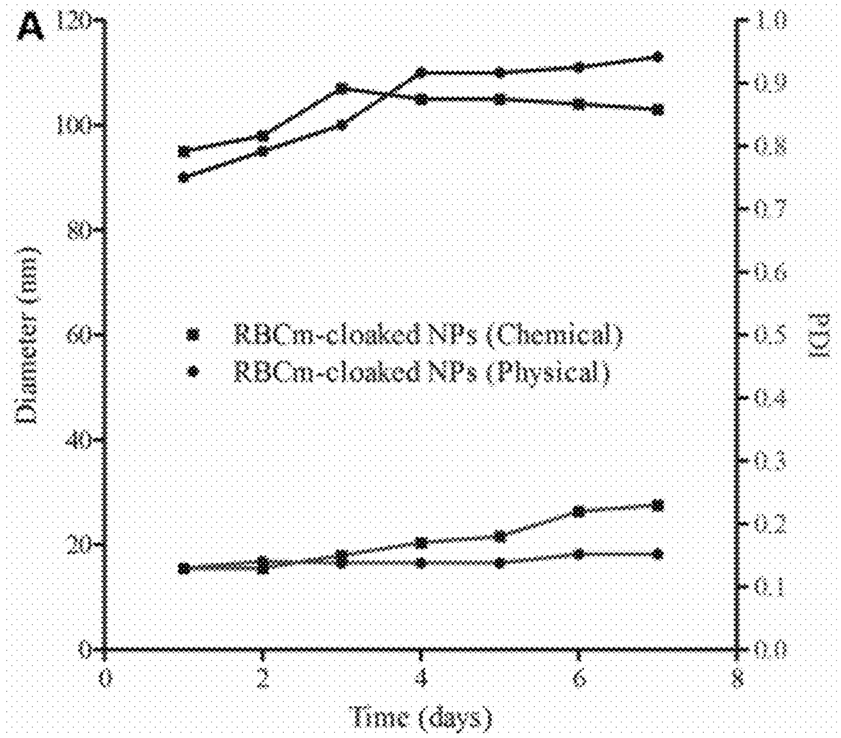
FIG. 11(A) Long-term stability of DOX-loaded RBCm-cloaked NPs in terms of particle size (diameter, nm) and polydispersity index (PDI) in PBS buffer, which were monitored for a period of 7 days at room temperature.
Figure 11B:
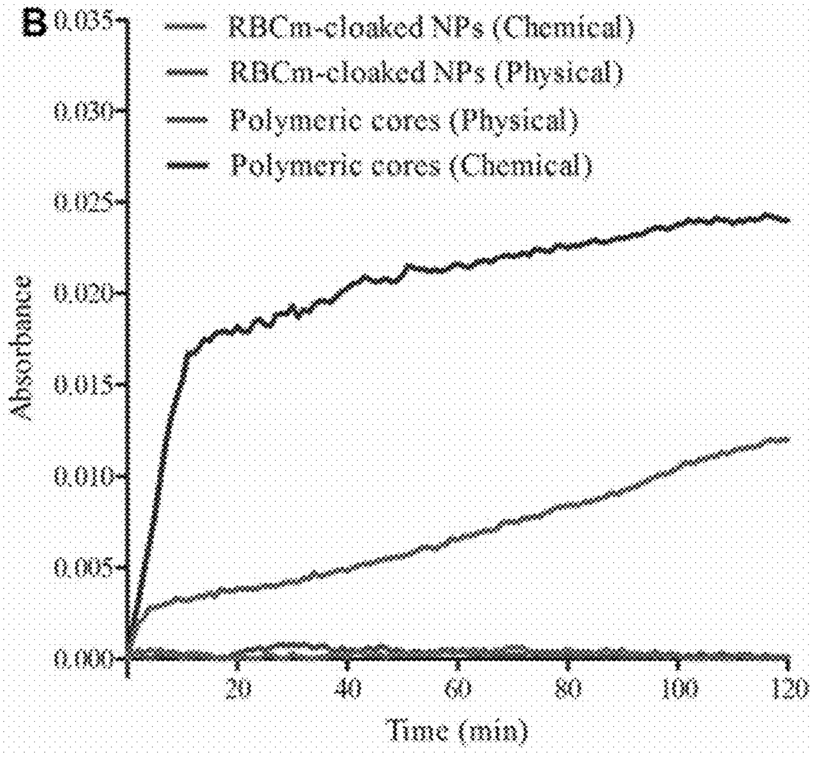
FIG. 11(B) Stability of DOX-loaded RBCm-cloaked NPs and bare NP cores (without RBCm cloak) in 100% FBS was assessed by measuring the UV-absorbance at the wavelength of 560 nm.

Next, the inventor studied the stability of DOX-loaded RBCm-cloaked NPs in physiologically relevant buffer solutions. In PBS, NP stability is monitored by measuring NP sizes at different time points, as unstable particles tend to aggregate and their sizes increase. In this study (FIG. 11A), NPs loaded with DOX molecules by using both physical encapsulation and chemical conjugation showed similar initial diameters of ~90 nm without significant size increase over the span of one week. Similarly, only a slight change in the PDIs of the NPs was observed over the same time span, indicating a high stability of DOX-loaded RBCm-cloaked NPs in PBS. NP stability was further examined in serum by monitoring UV absorbance at 560 nm, a characteristic wavelength reflecting the extent of particle aggregation [14, 15]. RBCm-cloaked NPs, loaded with DOX molecules by either physical encapsulation or chemical conjugation, showed a nearly constant absorbance at 560 nm over a time span of two hours (FIG. 11B), suggesting that the NPs are highly stable in 100% fetal bovine serum (FBS). In contrast, absorbance of bare polymeric cores made from PLGA or PLA-DOX conjugates without RBCm cloaks immediately increased upon addition into FBS. These results showed that the RBCm cloak played a significant in stabilizing NPs in both buffer solutions and serum. From a practical perspective, the fast aggregation of uncoated polymeric particles in buffer solutions provided a way of selective precipitation and removal of uncoated particles from RBCm-cloaked NPs after their preparation.

3.4. Release Kinetics of DOX from RBCm-Cloaked NPs

Figure 12A:
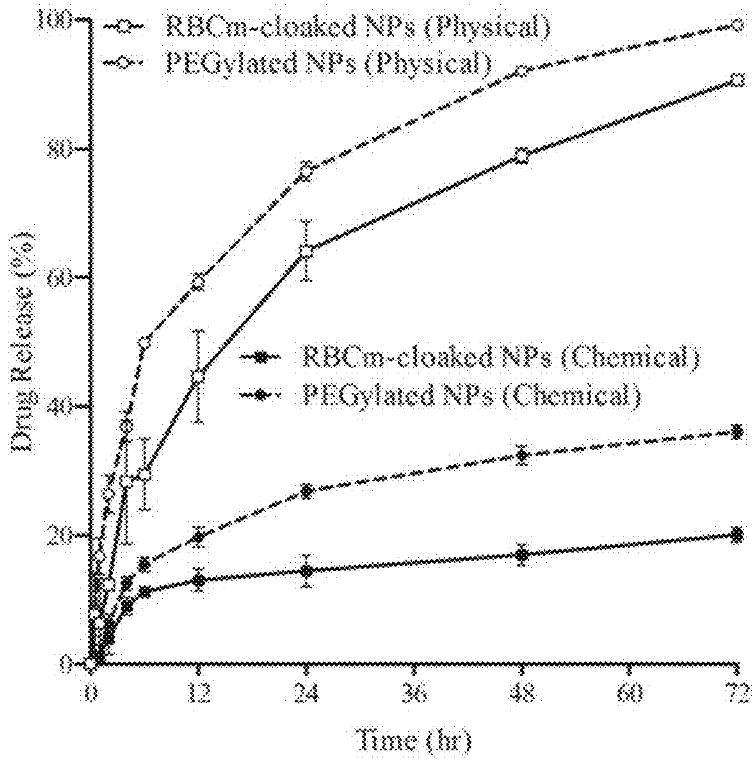
FIG. 12(A) DOX release profiles of RBCm-cloaked NPs and PEGylated NPs. For these release studies, initial DOX concentration inside the NPs was 5 wt % for chemical conjugation and 1.8 wt % for physical encapsulation, respectively.

Following the formulation of stable DOX-loaded RBCm-cloaked NPs, the inventors proceeded to investigate their DOX release kinetics (FIG. 12). The inventors first examined how different drug loading mechanisms would affect DOX releases from RBCm-cloaked NPs. The results showed that, when DOX molecules were physically encapsulated into the polymer matrix, the drug release rate was significantly faster, as 20% of DOX molecules were released within the first two hours from the RBCm-cloaked NPs. In contrast, when formulations of chemical conjugation were examined, within the first two hours, only 5% of DOX molecules were released. Such difference has been attributed to the fact that covalent bonding of DOX molecules to the polymer backbone requires drug molecules first be hydrolyzed from the polymer by bulk erosion before they can diffuse out of the polymeric matrix for release [11, 12, 16]. A more sustained release profile resulted from drug-polymer covalent conjugation also suggests that chemical linkers responsive to environmental triggers can achieve better-controlled drug releases when developing RBCm-cloaked NPs for advanced drug delivery applications [13, 17].

In order to gain a better understanding on the role played by RBCm cloak in drug retention, the inventors followed an established procedure to generate NPs by blending PLA-PEG di-block copolymers and resulted in PEGylated NPs, where NP cores were coated and stabilized by a surrounding PEG layer instead of RBCm cloak [18]. If two formulations have similar NP cores, the difference in drug releases is primarily caused by the different abilities of RBCm cloak and surface PEG coating in drug retention. By comparing DOX release from RBCm-cloaked NPs to that from PEGylated NPs, the inventors found that the release rate of the RBCm-cloaked NPs was lower: approximately 20% of DOX was released within of the first 72 hours in the RBCm-cloaked NPs, whereas 40% of DOX was released from the PEGylated NPs over the same time span. In fact, by using NPs formulated by PLGA-PEG di-block copolymers, surface PEG molecules have been found to hinder drug release from NP cores [19].

Hence, the observation, where DOX is released at a higher rate from PEG-coated NPs compared to RBCm-cloaked NPs, indicates that RBCm indeed acts as a diffusion barrier for DOX release. This observation also in accordance with previous studies showing that phospholipid coating can act as a barrier to drug diffusion [20]. Such a role played by RBCm cloak further suggests that strategies aimed at engineering lipid membrane coatings may allow for responsive drug releases from RBCm-cloaked NPs under certain environmental cues in addition to those achieved by chemical conjugations embedded in polymer cores [21].

Figure 12B:
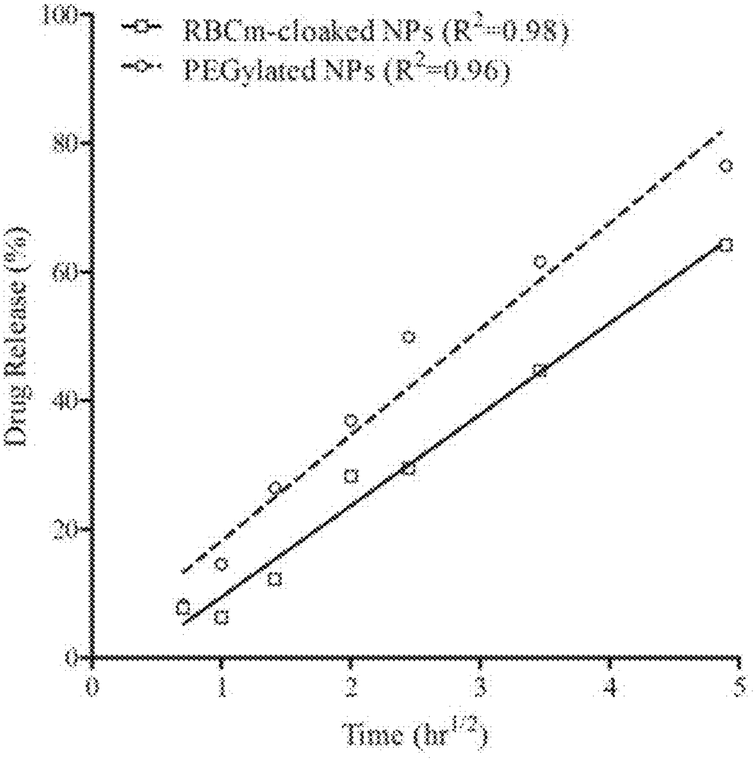
FIG. 12(B) For the physical encapsulation systems, the drug release percentage was plotted against the square root of time, which yielded linear fittings using a diffusion-dominant Higuchi model.

To gain a quantitative understanding on the membrane coating effect on drug retention, the drug release profiles were analyzed using mathematic models established in pervious particle drug release studies. Since the degradation of PLGA is on the order of weeks [22, 23], markedly slower than the observed drug release for the physically loaded systems, a diffusion-dominant Higuchi model was applied to both RBCm-coated and PEGylated NPs containing physically encapsulated DOX. Plotting the drug release percentage against the square root of time yielded linear fittings with $R^2$=0.98 and 0.96 for the RBCm-cloaked and the PEGylated NPs, respectively (FIG. 12B). The goodness of the fit implies a diffusion-controlled drug release mechanism and further allows for the derivation of the diffusion coefficient through the following Higuchi equations [24, 25]:

$$M_t = Kt^{1/2} \quad (1)$$

$$K = A(2C_{ini}DC_s)^{1/2} \quad (2)$$

where, $M_t$ is drug release at time t in hours, K is the Higuchi constant, $C_{ini}$ is the initial drug concentration, $C_s$ is the drug solubility, A is the total surface area of the particles, and D is the diffusion coefficient. Given the particle dimensions, the drug loading yield, the solubility of DOX in water (1.18 g/L), and the drug release data, the diffusion coefficients were determined to be $6.6\times10^{-16}$ $cm^2$/sec and $8.2\times10^{-16}$ $cm^2$/sec for the RBCm-clocked and PEGylated NPs, respectively, which are also consistent with previously reported drug diffusivities from PLGA/PLA NPs [26]. In our study, the bilayered membrane coating reduced the drug diffusivity by 1.2 times. This retardation effect by the RBCm cloak would likely vary with different particle sizes, polymer types, and therapeutic cargoes.

On the other hand, applying zero order, first order, and Higuchi models to the drug release profiles of chemically conjugated DOX yielded poor fittings (data not shown), indicating complex release kinetics when additional drug cleavage is coupled with drug diffusion out of the polymer matrix. Precise modeling of retardation effect imposed by the RBCm cloak on the chemically conjugated DOX is beyond the scope of this study.

Nevertheless, as identical particle cores are present in both RBCm-cloaked and PEGylated NPs, polymer matrix relaxation and hydrolytic cleavage of the linkage are not dominant factors contributing to the difference observed in DOX release profiles. Instead, the inventors contribute the slower release rate of the RBCm-cloaked NPs to two diffusion-dominated components: the diffusion of water into the polymer matrix and the diffusion of the cleaved drugs outward across the polymer matrix [27]. As the membrane coating was shown to decrease the drug diffusivity in the physical entrapment system, it likely affected both the influx of water and the efflux of cleaved drugs in the covalent conjugate system, thereby resulting in a more sustained drug release profile.

3.5. Cytotoxicity of DOX-Loaded RBCm-Cloaked NPs

Figure 13:
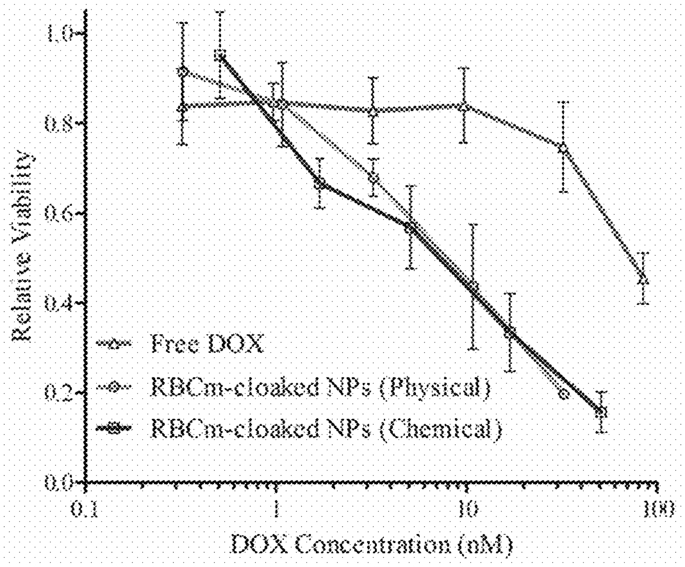
FIG. 13. A comparative cytotoxicity study against Kasumi-1 cell line established from the peripheral blood of an AML patient, where squares represent RBCm-cloaked NPs with chemically conjugated DOX, circles represent RBCm-cloaked NPs with physically encapsulated DOX, and triangles represent free DOX. All samples were incubated with Kasumi-1 cells for 72 hours prior to MTT assay (n=4).

Lastly, the inventors examined the therapeutic potential of the DOX-loaded RBCm-cloaked NPs against an AML Kasumi-1 cell line. AML, an illness characterized by uncontrolled growth and accumulation of leukemia blasts in the blood stream, was chosen as a disease target because of the RBCm-cloaked NPs' long circulation lifetime in the blood stream and their sustained drug release profiles. The current standard of care for AML is high-dose anthracyclines, which raises serious concerns for cardiac toxicity [28]. Long-circulating NPs releasing therapeutic compounds in a sustained manner offer the opportunity to reduce the necessary dosing and improve on the treatment efficacy. RBCm-cloaked NPs, where DOX were either physically loaded or covalently conjugated, exhibited higher toxicity in comparison to free DOX over a 72-hour incubation period (FIG. 13). This enhancement in efficacy can be likely attributed to endocytic uptake of NPs, which enables a high payload of drugs to enter the intracellular region [29]. The free DOX, in contrast, relies on passive membrane diffusion for cellular entry, which is less efficient and susceptible to membrane-bound drug efflux pumps [30-32]. This study suggests that RBCm-cloaked NPs, with a prolonged circulation lifetime, sustained drug release, and improved cell internalization, are a platform toward the treatment of blood cancer. Further studies are warranted to investigate the therapeutic potential of these NPs in vivo.

CONCLUSIONS

In summary, herein, the inventors examined two strategies for loading drugs into an RBCm-cloaked NP delivery system: physical encapsulation and chemical conjugation. Release studies suggested that chemical conjugation strategy resulted in a more sustained drug release profile. The inventors further formulated PEGylated NPs that had the same NP cores but different surface coatings compared to RBCm-cloaked NPs. By comparing drug release profiles of these two delivery systems, the inventors demonstrated that RBCm cloak provided a barrier slowing down the outward diffusion of encapsulated drug molecules. These results provide that chemical modifications on drug-polymer linkage in the NP core and engineering on the NP surface coatings can gain better controls over drug releases of RBCm-cloaked NPs. In a following efficacy study by using AML Kasumi-1 cell line, RBCm-cloaked NPs exhibited higher toxicity in comparison to free DOX. The previously observed long systemic circulation lifetime in the blood stream and the sustained drug release kinetics reported hereby indicate that this biomimetic drug delivery system provides a viable systemic delivery of payloads for the treatment of various diseases such as blood cancers. These RBCm-cloaked NPs provide a robust drug delivery system that combines the advantages of both synthetic polymers and natural cellular membranes.

RBCm-cloaked NPs represent a novel class of NP formulations bringing together both the long circulation lifetime of RBC and controlled drug retention and releases of synthetic polymers. This NP formulation can be further tailored by engineering both parts to improve systemic delivery of therapeutic payloads. This formulation provides a robust delivery platform and make significant impacts on both biomedical applications and nanotechnology research.

The executive summary of this example is provided as follows:

To combine the advantages of a long circulation lifetime from RBCs and controlled drug retention and releases from polymeric particles, the inventors formulated RBCm-cloaked NPs in sub-100-nm sizes, which contained: Sub-100-nm polymeric cores made from PLA or PLGA, and An erythrocyte exterior made from RBCm with preserved membrane proteins.

The inventors examined two distinct methods to load DOX as a model drug to the RBCm-cloaked NPs: Physical encapsulation, resulting loading yields ranging from 0.9% to 1.8%; and Covalent conjugation, resulting an approximate loading yield of 5%.

By monitoring NP sizes and UV absorbance, the inventors found that RBCm-cloaked NPs had a superior stability when compared to bare polymeric cores without RBCm cloaks, implying that the RBCm cloak played a significant role in stabilizing NPs in biological solutions.

Release studies showed drug-polymer covalent conjugation approach has a more sustained release profile than physical encapsulation, demonstrating that the chemical linkers responsive to environmental triggers could achieve better-controlled drug releases when developing RBCm-cloaked NPs for advanced drug delivery applications.

By comparing RBCm-cloaked NPs with PEGylated NPs, the inventors found that RBCm acted as a diffusion barrier for DOX release. This observation was consistent with quantitative analysis using Higuchi equations. Therefore, strategies aimed at engineering lipid membrane coatings can also enable responsive drug releases from RBCm-cloaked NPs under certain environmental cues.

DOX-loaded RBCm-cloaked NPs enhanced the efficacy against AML Kasumi-1 cells when compared to free DOX. This enhancement in efficacy can be likely attributed to endocytic uptake of NPs, which enables a high payload of drugs to enter the intracellular region.

REFERENCES

1. Davis M E, Chen Z, Shin D M. Nanoparticle therapeutics: an emerging treatment modality for cancer. *Nat. Rev. Drug Discov.* 7(9), 771-782 (2008).
2. Petros R A, DeSimone J M. Strategies in the design of nanoparticles for therapeutic applications. *Nat. Rev. Drug Discov.* 9(8), 615-627 (2010).
3. Peer D, Karp J M, Hong S, FaroKhzad O C, Margalit R, Langer R. Nanocarriers as an emerging platform for cancer therapy. *Nat. Nanotechnol.* 2(12), 751-760 (2007).
4. Farokhzad O C, Langer R. Impact of Nanotechnology on Drug Delivery. *ACS Nano* 3(1), 16-20 (2009).
5. Alexis F, Pridgen E, Molnar L K, Farokhzad O C. Factors affecting the clearance and biodistribution of polymeric nanoparticles. *Mol. Pharm.* 5(4), 505-515 (2008).
6. Knop K, Hoogenboom R, Fischer D, Schubert U S. Poly(ethylene glycol) in Drug Delivery: Pros and Cons as Well as Potential Alternatives. *Angew. Chem. Int. Edit.* 49(36), 6288-6308 (2010).
7. Geng Y, Dalhaimer P, Cai S et al. Shape effects of filaments versus spherical particles in flow and drug delivery. *Nat. Nanotechnol.* 2(4), 249-255 (2007).
8. Yoo J-W, Chambers E, Mitragotri S. Factors that Control the Circulation Time of Nanoparticles in Blood: Challenges, Solutions and Future Prospects. *Curr. Pharm. Design* 16(21), 2298-2307 (2010).
9. Hu C M, Zhang L, Aryal S, Cheung C, Fang R H, Zhang L. Erythrocyte membrane-camouflaged polymeric nanoparticles as a biomimetic delivery platform. *Proc. Natl. Acad. Sci. USA* 108(27), 10980-10985 (2011).
10. Dodge J T, Mitchell C, Hanahan D J. The preparation and chemical characteristics of hemoglobin-free ghosts of human erythrocytes. *Arch. Biochem. Biophys.* 100, 119-130 (1963).
11. Aryal S, Hu C M, Zhang L. Polymeric nanoparticles with precise ratiometric control over drug loading for combination therapy. *Mol. Pharm.* 8(4), 1401-1407 (2011).
12. Tong R, Cheng J. Ring-opening polymerization-mediated controlled formulation of polylactide-drug nanoparticles. *J. Am. Chem. Soc.* 131(13), 4744-4754 (2009).
13. Aryal S, Hu C M, Zhang L. Polymer—cisplatin conjugate nanoparticles for acid-responsive drug delivery. *ACS Nano* 4(1), 251-258 (2010).
14. Popielarski S R, Pun S H, Davis M E. A nanoparticle-based model delivery system to guide the rational design of gene delivery to the liver. 1. Synthesis and characterization. *Bioconjug. Chem.* 16(5), 1063-1070 (2005).
15. Fang R H, Aryal S, Hu C M, Zhang L. Quick synthesis of lipid-polymer hybrid nanoparticles with low polydispersity using a single-step sonication method. *Langmuir* 26(22), 16958-16962 (2010).

16. Tong R, Cheng J. Controlled Synthesis of Camptothecin-Polylactide Conjugates and Nanoconjugates. *Bioconjug. Chem.* 21(1), 111-121 (2010).

17. Gao W, Chan J M, Farokhzad O C. pH-Responsive Nanoparticles for Drug Delivery. *Mol. Pharm.* 7(6), 1913-1920 (2010).

18. Gu F, Zhang L, Teply B A et al. Precise engineering of targeted nanoparticles by using self-assembled biointegrated block copolymers. *Proc. Natl. Acad. Sci. USA* 105(7), 2586-2591 (2008).

19. Takae S, Miyata K, Oba M et al. PEG-detachable polyplex micelles based on disulfide-linked block catiomers as bioresponsive nonviral gene vectors. *J. Am. Chem. Soc.* 130(18), 6001-6009 (2008).

20. Zhang L, Chan J M, Gu F X et al. Self-assembled lipid-polymer hybrid nanoparticles: A robust drug delivery platform. *ACS Nano* 2(8), 1696-1702 (2008).

21. Pornpattananangkul D, Zhang L, Olson S et al. Bacterial Toxin-Triggered Drug Release from Gold Nanoparticle-Stabilized Liposomes for the Treatment of Bacterial Infection. *J. Am. Chem. Soc.* 133(11), 4132-4139 (2011).

22. Avgoustakis K, Beletsi A, Panagi Z, Klepetsanis P, Karydas A G, Ithakissios D S. PLGA-mPEG nanoparticles of cisplatin: in vitro nanoparticle degradation, in vitro drug release and in Vivo drug residence in blood properties. *J. Control. Release* 79(1-3), 123-135 (2002).

23. Li J, Jiang G, Ding F. The effect of pH on the polymer degradation and drug release from PLGA-mPEG microparticles. *J. Appl. Polym. Sci.* 109(1), 475-482 (2008).

24. Higuchi T. Rate of release of medicaments from ointment bases containing drugs in suspension. *J. Pharm. Sci.* 50, 874-875 (1961).

25. Siepmann J, Peppas N A. Higuchi equation: derivation, applications, use and misuse. *Int. J. Pharm.* 418(1), 6-12 (2011).

26. Budhian A, Siegel S J, Winey K I. Controlling the in vitro release profiles for a system of haloperidol-loaded PLGA nanoparticles. *Int. J. Pharm.* 346(1-2), 151-159 (2008).

27. Pitt C G, Schindler A. The kinetics of drug cleavage and release from matrices containing covalent polymer-drug conjugates. *J. Control. Release* 33(3), 391-395 (1995).

28. Lowenberg B, Ossenkoppele G J, van Putten W et al. High-Dose Daunorubicin in Older Patients with Acute Myeloid Leukemia. *New Engl. J. Med.* 361(13), 1235-1248 (2009).

29. Hu C-MJ, Zhang L. Therapeutic Nanoparticles to Combat Cancer Drug Resistance. *Curr. Drug Metab.* 10(8), 836-841 (2009).

30. Huwyler J, Cerletti A, Fricker G, Eberle A N, Drewe J. By-passing of P-glycoprotein using immunoliposomes. *J. Drug Target.* 10(1), 73-79 (2002).

31. Rapoport N, Marin A, Luo Y, Prestwich G D, Muniruzzaman M. Intracellular uptake and trafficking of pluronic micelles in drug-sensitive and MDR cells: Effect on the intracellular drug localization. *J. Pharm. Sci.* 91(1), 157-170 (2002).

32. Sahoo S K. Labhasetwar V. Enhanced anti proliferative activity of transferrin-conjugated paclitaxel-loaded nanoparticles is mediated via sustained intracellular drug retention. *Mol. Pharm.* 2(5). 373-383 (2005).

Example 3

Nanoparticles with Cancer Cell Membranes for Personalized Immunotherapy

The present example provides a immunotherapeutic system that has several advantages over existing approaches.

1) Current strategies concentrate only on individual tumor associated antigens (TAAs) that are expressed by the general cancer type in question. Cancer is a heterogeneous disease, and one limitation of such an approach is that the antigen expression of one patient's cancer could be completely different from another's. This leads to a less than optimal percentage of patients who are actual candidates for receiving such treatments. Another concern is that targeting a single TAA leads to a weak overall immune response against the cancer, allowing it to ultimately mutate and develop resistance. The described invention solves these problems by tailoring the treatment towards each individual patient via the collection of membrane material from their autologous tumors. This approach allows the accurate recreation of the antigen expression profile onto the nanoparticle, which gives the immune system a chance to mount a strong, multi-pronged response against the cancer.

2) Another limitation of current strategies is that they for the most part require the chemical conjugation of the TAAs to the immunological adjuvant. This is done in order to co-localize the antigen with the adjuvant, which ultimately allows the immune system to mount a response against self-antigens that would otherwise have low immunogenicity. The problem with such an approach is that chemical conjugations can often distort the antigens, resulting in poor presentation by the APCs. Additionally, the random nature of chemical conjugations can lead to low yields and results in the inability to generalize such a system for use with different kinds of TAAs at the same time. The described invention addresses both of these aforementioned problems. By translocating the entire cell membrane onto the nanoparticle, all of the surface membrane TAAs are in their native environment and are therefore faithfully presented by APCs in their native form. The use of a nanoparticle core allows for the co-delivery of immunological adjuvant with the antigenic material at tunable adjuvant to antigen ratios, something that cannot be done with traditional chemically conjugated systems.

3) Most current cancer vaccines are small compounds with unfavorable pharmacokinetics and biodistributions. Once injected in vivo these compounds can diffuse away from the target site or be degraded before uptake by APCs. The described invention overcomes this in a variety of ways. First, because the membrane is supported by a nanoparticle surface, it is much less likely to fuse with unwanted targets. In this way, the antigens can be preserved and stabilized in their optimal form until uptake by APCs. Additionally, nanoparticle systems are orders of magnitude larger than small compounds; the size of the nanoparticles can also be fine-tuned over a large range. By controlling the nanoparticle core size to be around 200-300 nm, diffusion away from the target site can be prevented, allowing APCs to come in and take up the particles efficiently. At the same time, the small size of the nanoparticles also allows for the maximization of surface area on which the membrane material can reside, leading to the delivery of more antigenic material per dosage.

Figure 14:
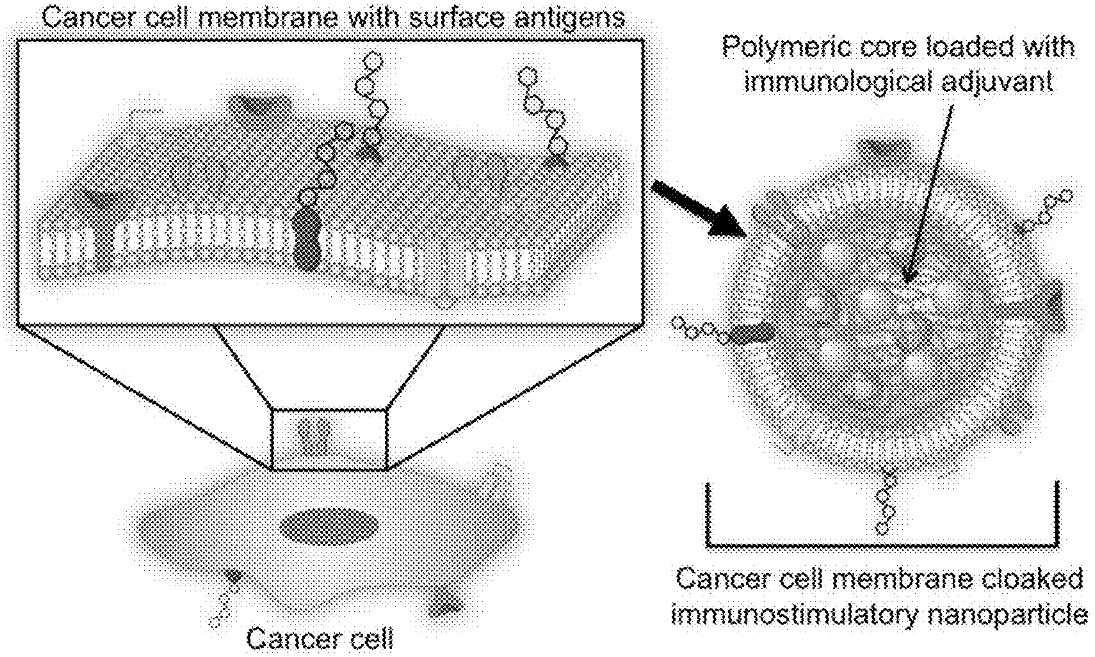
FIG. 14. Schematic illustration of cancer cell membrane cloaked immunostimulatory nanoparticle as a cancer treatment vaccine.

The present example provides that cancer cell membrane material is derived from a patient's tumor or from an established cell line and is used to coat nanoparticles with immunological adjuvant loaded inside in order to create a potent cancer vaccine (FIG. 14). Using this platform, it is possible to deliver all of the antigenic material from a cancer cell's surface to antigen presenting cells (APCs). Additionally, the co-delivery of an immunological adjuvant will allow the immune system to mount a strong response against otherwise weakly immunogenic material. This strategy can be used to treat a wide array of cancer types including, but not limited to: bladder cancer, bone cancer, brain cancer, breast cancer, cervical cancer, colorectal cancer, gastric cancer, liver cancer, ovarian cancer, pancreatic cancer, lung cancer, skin cancer, and prostate cancer.

The described cancer vaccine can be used for both preventative and therapeutic purposes. Using established cancer cell lines as the membrane source, patients can be vaccinated against cancers expressing common antigen motifs. On the other hand, using membrane material derived from an individual patient's tumor, a strong immune response can be mounted against the exact cancer type of the patient. This would have broad implications for the treatment of cancer given the heterogeneity of the disease from patient to patient.

Figure 15:
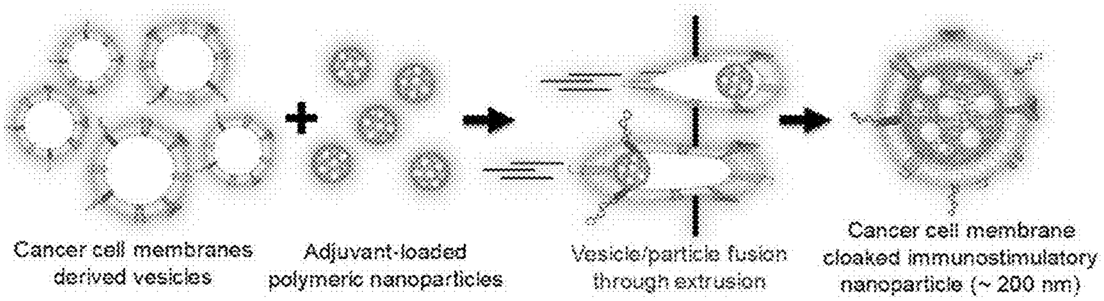
FIG. 15. Illustration of a three-step process to prepare cancer cell membranes cloaked polymeric nanoparticles: synthesizing adjuvant-loaded polymeric nanoparticles, making cancer cell membrane derived vesicles, and fusing the polymeric nanoparticles with the vesicles.

Treatment Preparation:

1) Cancer cells are derived from a patient's resected tumor or from a common cancer cell line,
2) The membrane material is derived from the cells using a method such as fractionation. An example is as follows:
   - The cancer cells are mechanically homogenized to disrupt the membrane,
   - The homogenate is spun down to pellet the intracellular contents and the supernatant with membrane is collected.
3) Nanoparticles loaded with adjuvant are prepared using a method such as nanoprecipitation. An example is as follows:
   - Polymer (e.g. PLGA) and adjuvant (e.g. monophosphoryl lipid A) are dissolved in an organic phase,
   - The organic phase is nanoprecipitated into an aqueous phase to form nanoparticles of the desired size.
4) The final immunotherapeutic particles are made as follows:
   - The membrane material collected from cancer cells is physically extruded to make smaller membrane vesicles,
   - The premade adjuvant-loaded cores are extruded along with the vesicles to form the final particles (FIG. 15).

Figure 16:
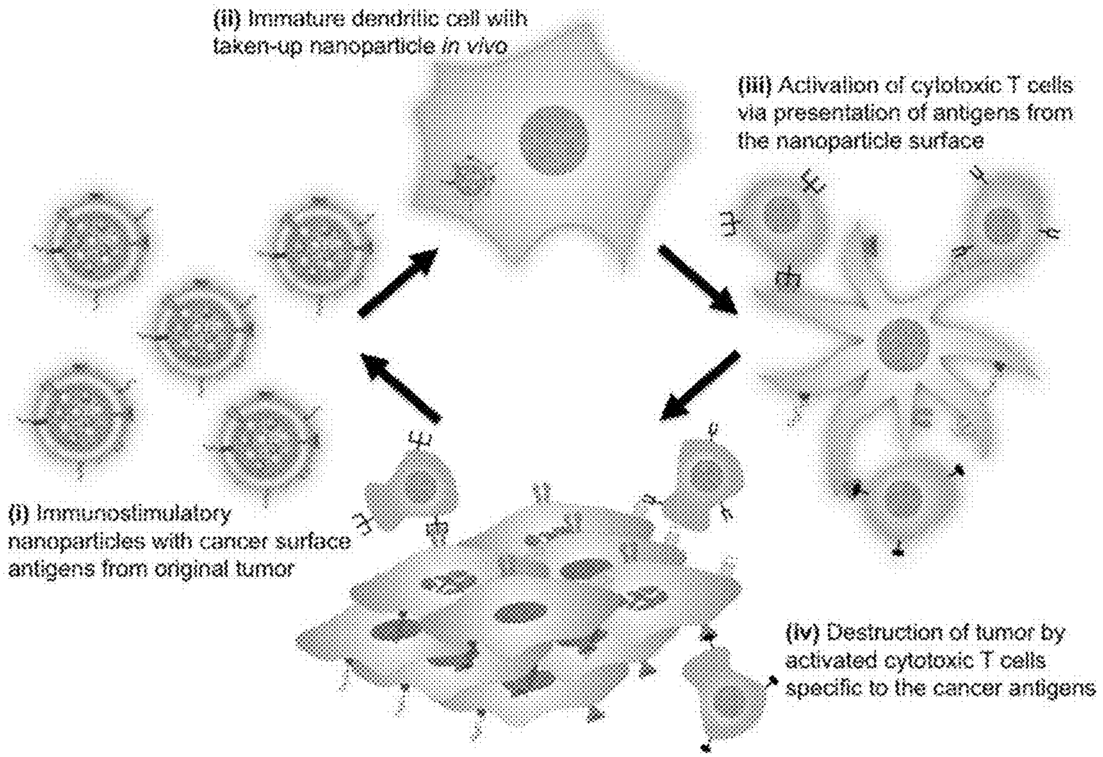
FIG. 16. Schematic illustrating the working mechanism of the proposed personalized cancer treatment vaccine: (i) cancer cells are collected from individual patient's tumor and the natural cancer cell membranes are used to wrap adjuvant-loaded nanoparticles; (ii) these immunostimulatory nanoparticles are taken up by immature dendritic cells and thus trigger their maturation; (iii) the matured dendritic cells present the cancer antigens to cytotoxic T cells and activate an immune response against the antigens; (iv) the activated cytotoxic T cells destroy the tumor expressing the specific cancer antigens.
Figure 17A:
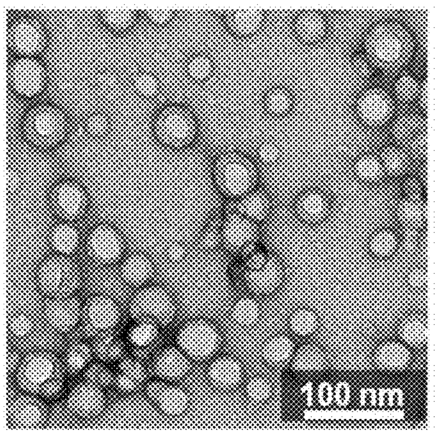
FIG. 17A TEM image show the core-shell structure of the cancer cell membrane cloaked PLGA nanoparticles.
Figure 17B:
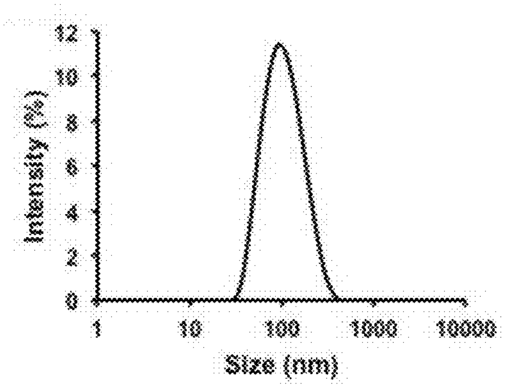
FIG. 17B Nanoparticle diameter as measured by DLS.
Figure 17C:
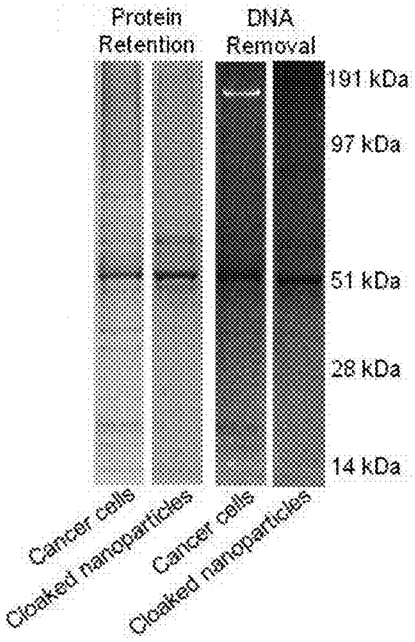
FIG. 17C SDS-PAGE of protein and DNA contents of dialyzed cancer cell membrane cloaked nanoparticles in comparison to whole cancer cells.
Figure 17D:
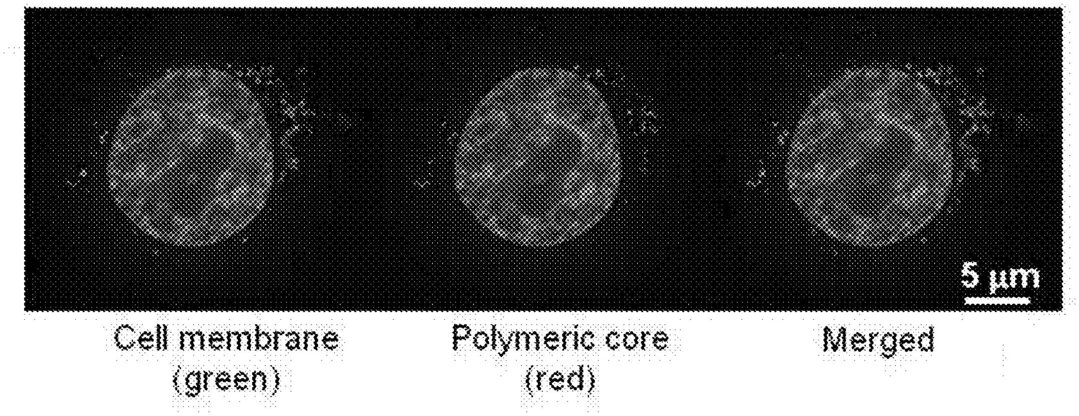
FIG. 17D Deconvolution fluorescence microscopy images demonstrate co-delivery of membrane materials with PLGA cores. The cancer cell membrane is stained with NBD dye (green greyscales), the polymeric core is loaded with DiD dye (red greyscales), and the nucleus is stained with DAPI (blue greyscales).

Treatment Administration:

1) The nanoparticle formulation is administered subcutaneously
2) Alternatively, the treatment is administered intravenously Mechanism of Action (FIG. 16):

1) Upon injection into the patient, a primary immune response is triggered,
2) APCs migrate to the inflammation site and take up the particles,
3) Upon uptake, the particles are degraded, releasing the immunological adjuvant,
4) Upon detecting the immunological adjuvant, the APCs mature,
5) The antigenic material that was on the nanoparticle surface is now presented on the exterior of the APCs,
6) The antigens on the mature APCs are presented to CD8+ T cells,
7) Upon interfacing with cancer-specific antigens, the CD8+ T cells activate and become cytotoxic T cells, and
8) Cytotoxic T cells against the cancer cell antigens proliferate and attack the tumor.

The present example provides a cancer cell-coated nanoparticle-based immunotherapeutic vaccine, and the feasibility of manufacturing such a vaccine (FIG. 17). The inventors have confirmed that it is possible to manufacture cancer cell membrane coated nanoparticles with encapsulated payloads. Membrane material derived from the cancer cells are devoid of large intracellular content and are efficiently translocated to the nanoparticle surface. Additionally, the inventors have confirmed that, upon uptake by a cell, the contents of the nanoparticle core and the outer membrane material are co-localized, which represents the most important data in verifying a successful design. Herein, the inventors conduct the in vitro and in vivo experiments that are required to prove the efficacy of the platform. These experiments include: 1) confirming the presentation of cancer cell antigenic material through the pulsing of immature dendritic cells with our nanoparticle formulation, 2) confirming the activation of CD8+ T cells upon co-culture with mature dendritic cells from the first experiment, 3) determination of therapeutic efficacy in vivo using a C57BL/6 with B16 melanoma murine model and observing for a reduction in tumor size upon direct administration of the treatment.

The described invention holds enormous potential for commercialization. Because it is easy to manufacture, is personalizable to each individual patient, and can be generalized to almost any form of cancer, such technology could eventually reside on the frontline of cancer treatment. On the therapeutic side, this immunotherapeutic treatment can be used along with surgery. Material from resected tumors is used to make the vaccine, which is administered to the patient to destroy any tumor remains and prevent tumor recurrence. On the preventative side, the treatment can be generalized to use established cell lines of common cancers to vaccinate against many cancer types.

REFERENCES

1. Cho, Nam-Hyuk et al. "A Multifunctional Core-Shell Nanoparticle for Dendritic Cell-Based Cancer Immunotherapy." *Nature Nanotechnology:* 6, 675-82 (2011).
2. Li, Haiyan et al. "Alpha-Alumina Nanoparticles Induce Efficient Autophagy-Dependent Cross-Presentation and Potent Antitumour Response." *Nature Nanotechnology* 6, 645-650 (2011).
3. Moon, James J et al. "Interbilayer-Crosslinked Multilamellar Vesicles as Synthetic Vaccines for Potent Humoral and Cellular Immune Responses." *Nature Materials* 10.3 (2011): 243-251.
4. Tongchusak, S et al. "Induction of Anti-Tumor Cytotoxic T Cell Responses Through PLGA-Nanoparticle Mediated Antigen Delivery." *Biomaterials* (2011), 32(14):3666-78.

Example 4

Biomimetic Toxin Nanosponges

Antitoxin treatments offer the potential to cleanse the body of virulence factors that underlie numerous health threats including bacterial infections, venomous injuries, and biological weaponry. Yet despite growing efforts in antitoxin development, safe and effective treatment options remain limited. Herein, the inventors construct a biomimetic nanosponge and demonstrate its ability to absorb and neutralize α-toxin from *Staphylococcus aureus*. Consisting of polymeric nanoparticle-supported RBC membrane bilayers, these nanosponges readily take in the membrane-damaging toxin and divert them away from their cellular targets. In a mouse model, the nanosponges markedly reduce the toxicity of the toxin. This biologically inspired nanoformulation presents an advance in nanomedicine for antitoxin treatments.

The growing awareness of toxin-mediated diseases and injuries has motivated the search for safer and more effective antitoxin solutions. Moreover, toxin-targeted anti-virulence therapy is emerging as a compelling strategy against infectious diseases amidst the rising threat of antibiotic-resistant bacteria (1). Existing antitoxin platforms, such as anti-sera (2), monoclonal antibodies (3, 4), small-molecule inhibitors (5, 6), and molecularly imprinted polymers (7, 8) neutralize toxins by targeting their molecular structures. However, factors including high immunogenicity, low biocompatibility, poor pharmacokinetics, as well as the need for toxin-specific custom synthesis limit their clinical adoption. Using a biodegradable PLGA polymer and the membrane components of red blood cells, the inventors construct a biomimetic nanosponge that targets the action mechanism of pore-forming toxins (PFTs).

PFTs are the most common protein toxins found in nature (9, 10). These toxins disrupt cells by forming pores in cellular membranes and altering their permeability. In bacterial infections, the attack by PFTs constitutes a major virulence mechanism by playing a key role in microbial defense and nourishment (10). It has been found that, in *Staphylococcus aureus*, the level of the membrane-damaging α-toxin expression correlates directly with the virulence of the strain (11). Studies have demonstrated that the inhibition of α-toxin can reduce the severity of *S. aureus* infections (11, 12), and similar PFT-targeted strategies have shown therapeutic potential against other pathogens including *Clostridium perfringens, Escherichia coli* (13), *Listeria monocytogenes* (14, 15), *Bacillus anthracis* (16), and *Streptococcus pneumoniae* (17, 18).

Figure 18A:
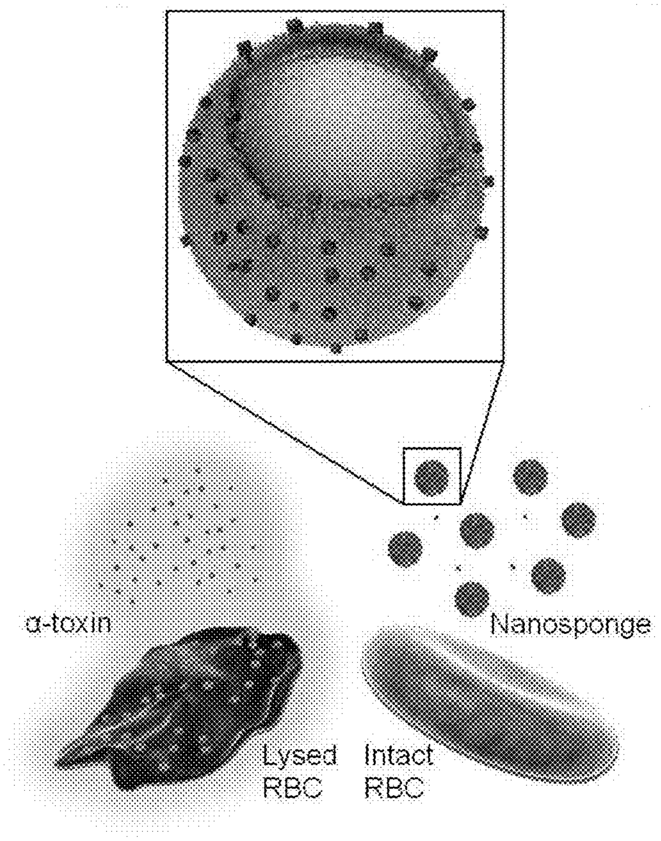
FIG. 18A Schematic of the toxin nanosponges in neutralizing PFTs. The nanosponges consist of substrate-supported RBC bilayer membranes into which PFTs can incorporate.

Aside from their roles in bacterial pathogenesis, PFTs are commonly employed in venomous attacks by animals, including those of sea anemones, scorpions, and snakes (19). It has become evident that effective treatments against these widespread cytolytic toxins would address a multitude of health issues. Over 80 families of PFTs have been identified, displaying diverse molecular structures and distinctive epitopic targets. Despite these differences, the functional similarity among these toxins in perforating cellular membranes provides the design cue for a mechanism-targeted antitoxin platform with a broad applicability. In general, PFTs disrupt cellular membranes through spontaneous incorporation into phospholipid bilayers. This propensity to interact with lipid membranes has inspired a number of applications based on bilayered membrane platforms (20-22). Herein, the inventors apply the use of nanoparticle-stabilized RBC membranes to absorb and arrest membrane-damaging proteins. Using staphylococcal α-toxin as the PFT model, the inventors demonstrate that these nanosponges can neutralize the toxin's virulent pore-forming activity (FIG. 18A).

Figure 18B:
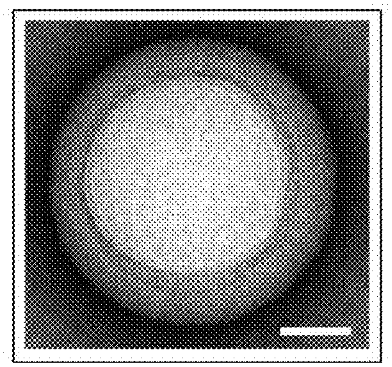
FIG. 18B TEM visualization of a single nanosponge in the presence of α-toxin. The sample was negatively stained in uranyl acetate (scale bar=20 nm).
Figure 18C:
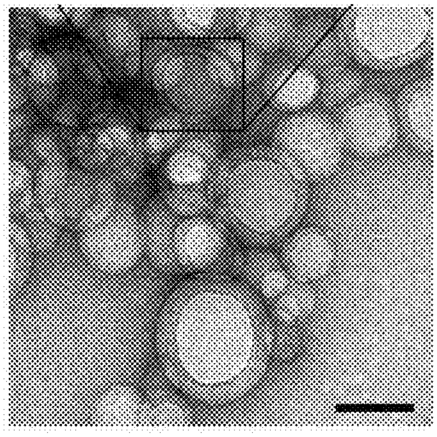
FIG. 18C TEM visualization of nanosponges mixed with α-toxin (scale bar=80 nm).
Figure 22:
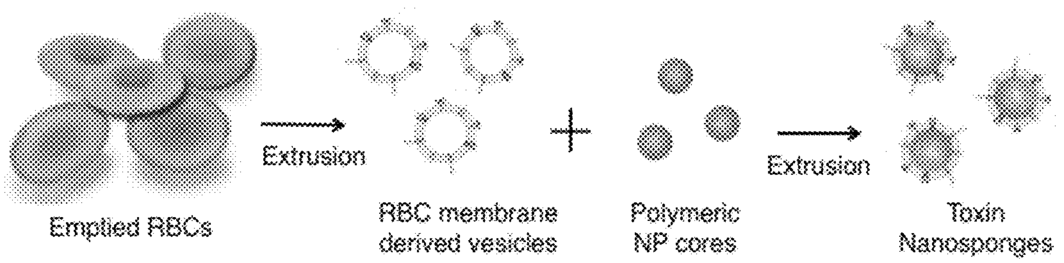
FIG. 22. Schematic of the preparation process of the toxin nanosponges.

The toxin nanosponges were prepared by extruding red blood cell membrane vesicles with 70 nm PLGA nanoparticles (FIG. 22), yielding a core-shell nanostructure approximately 85 nm in diameter (FIG. 18B, 18C). The RBC membrane vesicles were derived from RBCs purified from the whole blood of mice, and the PLGA particles were prepared from a nanoprecipitation process. This red-blood cell membrane coating technique was previously reported to camouflage nanoparticles, improving their serum stability and extending their in vivo circulation half-life (23). In the present study, the interaction between these particle-supported RBC membranes and hemolytic α-toxin is visited. Under transmission electron microscopy, the nanosponges revealed a core-shell structure, consisting of a polymeric core wrapped in RBC bilayers (FIG. 18C).

Figure 19A:
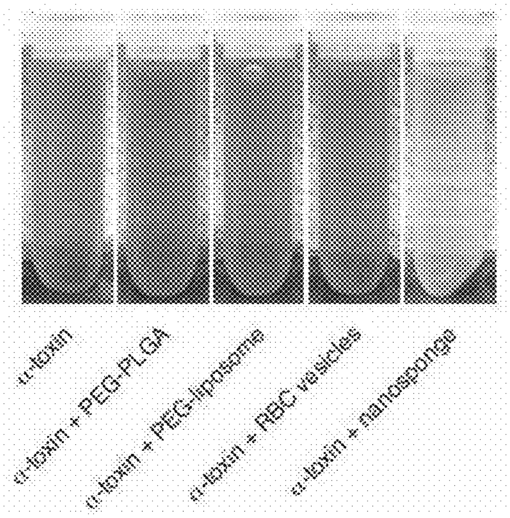
FIG. 19A Centrifuged RBCs after 30 min incubation with α-toxin prepared in PBS, PEGylated PLGA nanoparticle, PEGylated liposome, RBC membrane vesicles, and toxin nanosponges solutions. Each tube contained 5% purified RBCs, 3 μg of α-toxin, and 200 μg of the corresponding nanoformulation in a final volume of 2 mL PBS.
Figure 19B:
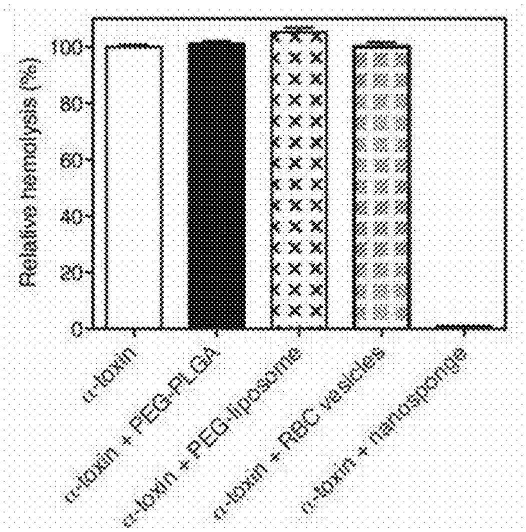
FIG. 19B Quantification of the RBC hemolysis based on the absorbance at 540 nm.

To establish the nanosponges' ability to neutralize α-toxin, 200 μg of nanosponges was mixed with 3 μg of α-toxin in PBS for 30 min. The mixture was subsequently mixed with 5% of purified mouse RBCs. As a comparison, an equivalent amount of PEGylated PLGA particles, PEGylated liposomes, and RBC membrane vesicles of comparable sizes were mixed with the toxin. Following 30 min of incubation, the solutions were centrifuged and the supernatant was observed for released hemoglobin. As shown in FIG. 19A, the nanosponge sample was noticeably different from the other samples, exhibiting a clear supernatant that indicated the RBCs were undamaged. Using toxin-treated and PBS-treated RBC solutions as positive and negative controls, the degree of hemolysis was quantified by measuring the absorbance of the supernatant at 540 nm. While PEGylated PLGA nanoparticles, PEGylated liposomes, and RBC membrane vesicles failed to deter the hemolytic activity of the toxin, the sample with nanosponges showed complete toxin inhibition.

Figure 19C:
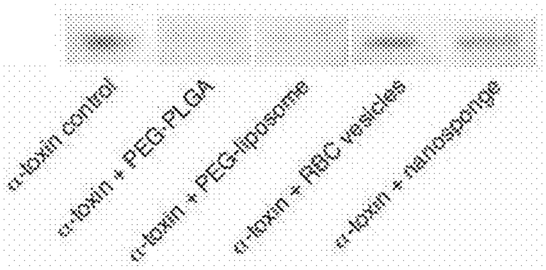

To better elucidate the mechanism behind the α-toxin inhibition, the nanoformulations/toxin mixtures were filtered through a Sepharose® CL-4B column to separate out free-floating, unbound toxin. Given α-toxin's tendency to spontaneously incorporate into erythrocyte membranes (24) and to substrate-supported membrane bilayers (25), the RBC membrane vesicles and the nanosponges were expected to retain the toxin after being run through the filtration column. Following SDS-PAGE analysis, it was found that the both the RBC membrane vesicles and the nanosponges retained the majority of the α-toxin (95.3 and 90.2% respectively) as indicated by the 34 kDa protein band of similar intensity to the toxin reference (FIG. 19C). On the other hand, the toxin protein band was almost nonexistent in the PEGylated PLGA NPs and the PEGylated liposome samples (3.4 and 4.7% respectively), which suggested that the PEGylated formulations had little interaction with the toxin. This lack of toxin retention can be attributed to the hydrophilic PEG coating, which precludes protein interactions through steric repulsions. The nanosponges, which are stabilized by a solid core and camouflaged by RBC membrane components, can interact directly with toxin targets.

Figure 19D:
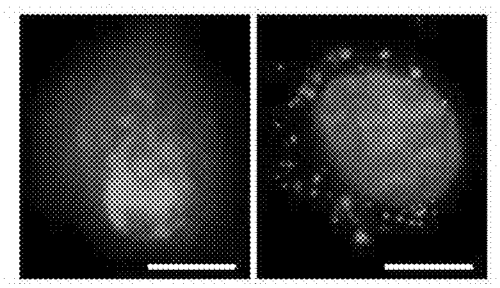
FIG. 19D A lipophilic dye, DMPE-rhodamine (red), was incorporated with the nanoformulations to indicate the distributions of the membrane materials upon incubation with cells. Following 1 h of incubation with human umbilical vein endothelial cells, the broad distribution of the dye (left) suggested that the membrane vesicles likely fused with the cellular membrane, and the distinctive particulates (right) indicated that the membrane materials of the nanosponges were taken up intracellularly.

Even though the RBC membrane vesicles also absorbed α-toxin, their failure to reduce the toxin's hemolytic activity highlights the role of the polymeric core in the nanosponges. To better understand the disparity between the neutralization capabilities of the RBC membrane vesicles and the nanosponges, a cellular uptake study was conducted using the two nanoformulations prepared with a membrane dye, DMPE-rhodamine. Fluorescence microscopy tellingly revealed the different fates of the two nanoformulations upon incubation with cells (FIG. 19D). In the sample with RBC membrane vesicles, a broadly distributed red fluorescence was cast over the entire cellular area, which can be explained by the fusion of these unstabilized vesicles with the cellular membrane. This observation is consistent with previous studies on liposomal RBC membrane vesicles, which were readily absorbed onto cell membranes and did not undergo cellular endocytosis (26). In contrast, the nanosponges showed up as distinct fluorescent particles within the intracellular region, demonstrating the ability of the polymeric cores to stabilize the RBC membrane component and enable its cellular uptake. These findings help to justify the results from the hemolysis study, in which case the RBC vesicles with bound α-toxin likely fused with the RBCs and thus failed to deter hemolysis. The nanosponges, on the other hand, were able to arrest the toxin and keep them away from the other RBC membranes. In addition, FIG. 19D suggests that the nanosponges could facilitate the endocytic uptake of membrane-bound toxin. This nanoparticle-induced entry mechanism would enhance the endolysosomal digestion of the absorbed proteins, preventing further damages that the toxin could inflict.

Figure 19E:
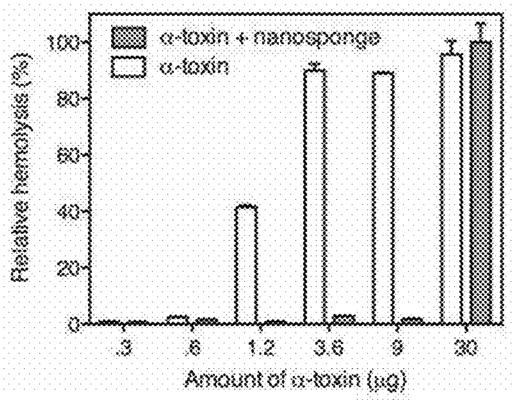
FIG. 19E Hemolytic activity of varying amounts of α-toxin with or without prior mixture with nanosponges. The overall nanosponge content was fixed at 200 μg and hemolysis was examined in 2 mL of PBS solution containing 5% of RBCs.
Figure 19F:
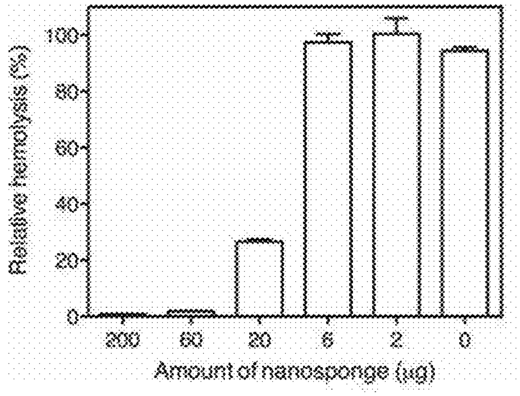
FIG. 19F Inhibition of α-toxin hemolysis with varying amounts of nanosponges. The overall toxin content was fixed at 9 μg and hemolysis was examined in 2 mL of PBS solution containing 5% of RBCs.

To further characterize the nanosponges, their toxin absorption capacity was examined through titration studies. Different amounts of α-toxin were incubated with 200 μl of 1 mg/ml nanosponges in PBS for 30 min. As a control, the same concentrations of α-toxin were prepared in the absence of the nanosponges. The toxin/nanosponge mixtures were subsequently added to 1.8 mL of PBS solution containing 5% of RBCs, and hemolysis was monitored following 30 min of incubation (FIG. 19E). In the absence of the nanosponges, significant hemolysis was observed with 1.2 μg of α-toxin (42%) and near complete hemolysis was achieved with 3.6 μg of α-toxin. With nanosponge treatment, however, negligible hemolysis was observed with up to 9 μg of α-toxin and complete hemolysis was achieved with 30 μg of the toxin. This data indicates that the nanosponges significantly reduced the α-toxin activity but had a capacity limit. An additional titration study of the nanosponges with the overall toxin content fixed at 9 μg revealed that the inhibition of the hemolytic activity correlated directly with the amount of nanosponges (FIG. 19F). It was approximated that 9 μg of the toxin could be completely neutralized by 200 μg of the nanosponges. Based on the titration data, the size of the nanosponge, the density of PLGA, and the molecular weight of the toxin, the absorption capacity of the nanosponge was estimated to be 173 toxin monomers per particle. As a comparison, the theoretical capacity of approximately 2000 toxin monomers per particle was estimated from the surface area of the nanosponges and the projection area of the toxin proteins. The lower experimental value can be attributed to steric hindrance among toxin molecules and the presence of RBC membrane proteins on the surface of the nanosponges.

Figure 20A:
FIG. 20A Representative skin lesions were observed on the toxin-injected mice 3 days following the injection.
Figure 20B:
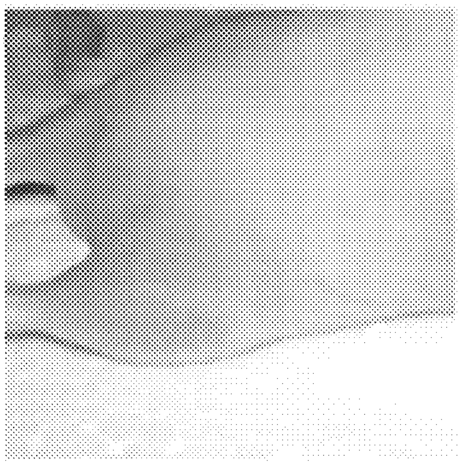
FIG. 20B Nanosponge-neutralized toxin injection showed no observable effect on the skin.
Figure 20C:
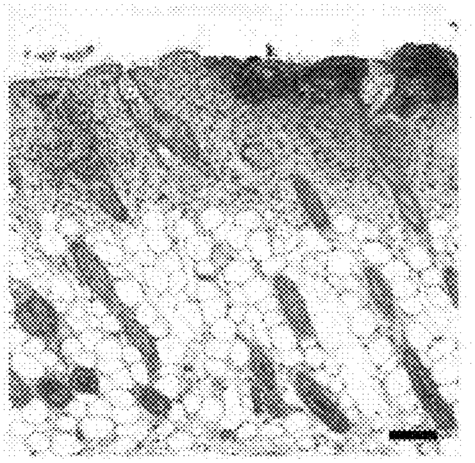
FIG. 20C Histological sectioning revealed that the toxin inflicted demonstrable inflammatory infiltrate, apoptosis, necrosis and edema in the epidermis. (Scale bar=80 μm) FIG. 20D No abnormality was observed in the epidermis following the injection of nanosponge-neutralized toxin. (Scale bar=80 μm) FIG. 20E Tears on muscle fibers, interfibril edema, and extravasation of neutrophils from surrounding vasculatures revealed the toxin damages on the muscles. (Scale bar=20 μm) FIG. 20F Normal muscle fiber structures and the lack of inflammatory signs suggest toxin neutralization by the nanosponges. (Scale bar=20 μm).
Figure 20D:
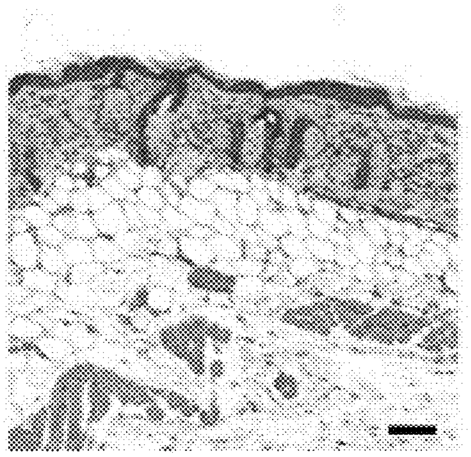
FIG. 20. 150 μL of 12 μg/mL α-toxin and the same formulation neutralized by 100 μg of nanosponges were injected into the flank region of mice subcutaneously.
Figure 20E:
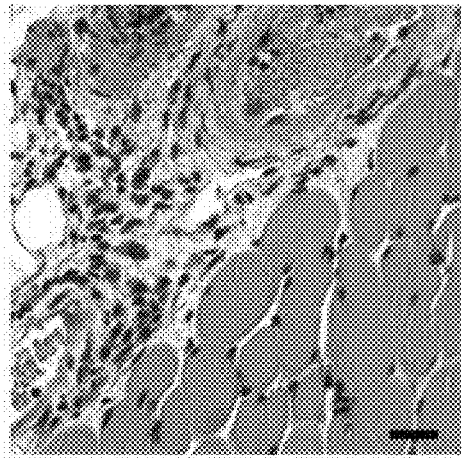
Figure 20F:
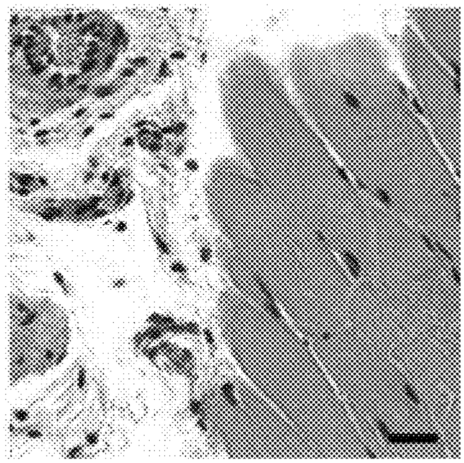

The ability of the nanosponges to neutralize α-toxin was tested in vivo by subcutaneous administration. Skin lesion formation in mice was compared 72 hours after the injection of α-toxin or α-toxin/nanosponge mixture beneath the right flank skin. Following a 150 μL injection at a concentration of 12 μg/mL, the α-toxin alone induced severe skin lesions with demonstrable edema and inflammation in the control group (FIG. 20A). However, mixing with 100 μg of the nanosponges (~69:1 toxin to particle ratio) appeared to neutralize the toxin, as there was no observable damage on the mice (FIG. 20B). Closer examination of the skin tissue harvested from the control group showed necrosis, apoptosis and inflammatory infiltrate of neutrophils with dermal edema (FIG. 20C). Moreover, the toxin inflicted damages to the underlying muscle tissue as evidenced by interfibril edema, tears on muscles fibers, and significant number of extravasating neutrophils from the surrounding vasculature (FIG. 20E). This contrasted strongly with what was observed in the tissue samples of mice receiving the toxin/nanosponge mixture (FIGS. 20D and 20F), which showed normal epithelial structures in skin histology and intact fibrous structures with no visible infiltrate in the muscle histology (FIGS. 20D, 20F).

Figure 21:
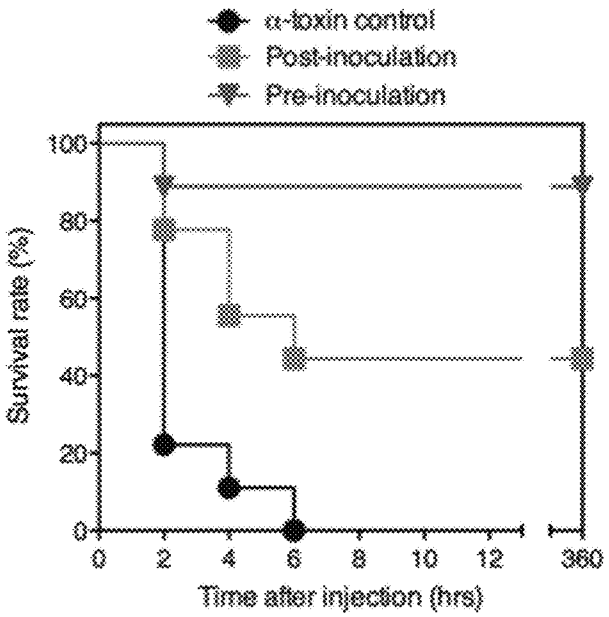
FIG. 21. Survival rates of mice over a 15-day period following intravenous injections of 75 μg/kg α-toxin (black); 80 mg/kg of nanosponges was administered intravenously 2 min either after (red greyscales) or before (blue greyscales) the toxin injection. p values were obtained using the log-rank test. The mice injected with toxin only had a 0% survival rate; the mice post-inoculated with the nanosponges had a 44% survival rate (p=0.0091); the mice pre-inoculated with the nanosponges had an 89% survival rate (p<0.0001). All injections were performed through the intravenous route via the tail vein (n=9).

The detoxification ability of the nanosponges was evaluated through systemic administration in mice. The safety of the nanosponges was first verified by injecting mice with 80 mg/kg of the nanosponges intravenously. The dose was well tolerated, as the inoculated group exhibited no mortality over a 2-week period (data not shown). Upon confirming the safety of the formulation, treatments through both pre- and post-inoculation were examined. A bolus lethal dose of α-toxin (75 μg/kg), known to induce acute death in mice, was injected through the tail vein. In the two experimental groups, 80 mg/kg of the nanosponges was injected either 2 min before or 2 min after the toxin injection. A 100% mortality rate was observed within 6 h of the toxin injection in the control group (n=9, FIG. 21). In the group that was post-inoculated with the nanosponges, the mortality rate was reduced markedly to 56% (p value is 0.0091; n=9). The survival rate was further improved in the pre-inoculation group, in which only an 11% mortality rate was observed (p value<0.0001; n=9). The results suggest that the nanosponges confer protection against the α-toxin in vivo. The benefit of the nanosponges was found to be higher when given prophylactically, which is unsurprising given the rapid kinetics of α-toxin hemolysis (27). In both treatment groups, no additional death was observed past the 6 h mark, suggesting that the absorbed toxin was detoxified rather than merely having its toxicity delayed. These results indicate the potential clinical applications of these nanosponges in both preventive and palliative settings.

In conclusion, the nanosponge, which consists of a PLGA nanoparticle-supported RBC membrane, was constructed as an antitoxin solution in light of the functional property of PFTs. The inventors demonstrated that membrane accessibility and structural stability are the key aspects that enable toxin neutralization via this platform. The nanosponges inhibited the hemolytic activity of α-toxin in vitro and greatly reduced the toxin's damage in mice. This toxin-absorbing platform presents a new paradigm in both therapeutic nanoparticles and antitoxin treatments. Unlike conventional stealthy strategies that preclude protein interactions through hydrophilic coatings, the RBC membrane-covered nanosponges can interact with toxic proteins and function as a toxin decoy in vivo. And unlike other structure-specific antitoxin platforms, the nanosponges address a common membrane-disrupting mechanism and have the potential to treat a variety of PFT-induced injuries and diseases. More importantly, the platform poses little risk of complication upon topical or systemic administration, as it is comprised entirely of biocompatible and biodegradable materials. The polymeric core could also be substituted with other therapeutic cargoes to create multimodal treatments against infectious diseases. As PFTs are the most common toxin, the nanosponge platform has tremendous therapeutic implications in clinics.

Experimental Absorption Capacity of Nanosponges

Density of PLGA: $\rho$=1.2 g/mL

Radius of the polymer core: r=35 nm

Mass of nanosponges:

$$M_{ns} = \rho \times \frac{4}{3}\pi r^3 = 2.2 \times 10^{-16}\text{g per particle} = 1.30 \times 10^8\text{g per mole}$$

Mass of α-toxin: $M_t$=34,000 g per mole

Based on the observation that 9 μg of toxin can be fully absorbed by 200 μg of NPs:

200 μg of nanosponges ~$1.5\times10^{-12}$ mole

9 μg of α-toxin ~$2.6\times10^{-10}$ mole

Toxin: NP=173:1

Theoretical Absorption Capacity of Nanosponges

Average diameter of the nanosponges: $r_{ns}$=42.5 nm

Nanosponge surface area: $A_{ns}=4\pi\, r_{ns}^2=22697$ nm$^2$

Assume fully packed heptameric rings of α-toxin on the nanosponges.

Based on 10 nm outer diameter of an oligomerized α-toxin ring (1), the projection area of the ring is:

$$A_{toxin\ heptamer} = \pi r_{ring}^2 = 78.5\ \text{nm}^2$$

Number of oligomerized rings per nanosponge=22697/78.5=289 heptameric rings

α-toxin monomers per nanosponge=289×7=2024

Materials and Methods

Preparation of Toxin Nanosponges

Nanosponge particles were synthesized as previously reported (2). Whole blood collected from 6 week-old male ICR mice (Charles River Laboratories) was centrifuged at 800× g for 5 min in order to isolate the RBCs. The RBCs were then subjected to hypotonic treatment and the RBC ghosts were collected by centrifuging at 800×g for 5 min. The resulting ghosts were serially extruded through 400 nm and 100 nm polycarbonate porous membranes using a mini extruder (Avanti Polar Lipids). PLGA polymeric cores were concurrently prepared using 0.67 dL/g carboxy-terminated 50:50 poly($_{DL}$-lactide-co-glycolide) (LACTEL Absorbable Polymers) using a solvent displacement process. PLGA was dissolved in acetonitrile at 1 mg/mL. To make 1 mg of particles, 1 mL of the PLGA solution was added dropwise into 3 mL of water. The resulting mixture was stirred in open air for 2 h and concentrated using 10 kDa molecular weight cutoff Amicon Ultra-4 Centrifugal Filters (Millipore). The final RBC nanosponges were synthesized by extruding the PLGA nanoparticles with vesicles prepared from fresh blood (1 mg PLGA per 1 mL blood) through a 100 nm polycarbonate membrane. Nitrogen purging was used to concentrate the nanoparticles as necessary. The weight of PLGA polymer is used for all subsequent mass values quoted for the nanosponges. The size of the nanosponges was obtained from three repeat dynamic light scattering measurements using a Malvern ZEN 3600 Zetasizer, which showed an average size of 85 nm.

Transmission Electron Microscopy of Toxin Nanosponges

100 μg of RBC nanosponges was incubated with 3 μg of *Staphylococcus aureus* α-toxin (Sigma Aldrich) for 15 min. A drop of nanoparticle solution was deposited onto a glow-discharged carbon-coated grid at a nanosponge concentration of 4 μg/mL. A minute after deposition, the droplet was washed away with 10 drops of distilled water and stained with 1% uranyl acetate. The sample was imaged under an FEI Sphera Microscope at 200 kV.

Preparation of PEGylated PLGA Nanoparticles, PEGylated Liposomes, and RBC Membrane Vesicles The PEGylated nanoparticles were prepared following a nanoprecipitation method. Briefly, 1 mg of PEG-PLGA diblock copolymer was dissolved in 1 mL of acetonitrile and added to a vial containing 3 mL of water under constant stirring. The organic solvent was then evaporated in the hood for 2 h. The NP solutions were then washed three times using an Amicon Ultra-4 centrifugal filter (Millipore) with a molecular weight cutoff of 10 kDa. The PEGylated liposomes were prepared from mechanical extrusion. Briefly, 1 mg of Egg PC and 200 μg of DSPE-PEG-carboxy (Avanti Polar Lipids) were dissolved in 1 mL of chloroform. The organic solvent was then evaporated by to form a dried lipid film. The lipid film was rehydrated with 1 mL of PBS, followed by vortexing for 1 min and sonicating for 3 min in an FS30D bath sonicator (Fisher Scientific). The formulation was subsequently extruded through a 100 nm pore-sized polycarbonate membrane 11 times in order to form narrowly distributed liposomes. The RBC membrane vesicles were prepared following the RBC purification and membrane extrusion protocols as described for the nanosponge preparation. The size of the nanoformulations were obtained from three repeat measurements using dynamic light scattering, which showed an average size of 90, 105, and 120 nm for the PEGylated PLGA nanoparticles, the PEGylated liposomes, and the RBC membrane vesicles, respectively.

RBC Nanosponges Competitive Neutralization Assay

3 μg of α-toxin was incubated for 30 min with 200 μL PBS solutions containing 1 mg/mL of RBC nanosponges, PEGylated PLGA nanoparticles, PEGylated liposomes, and RBC membrane vesicles. A negative control was prepared with 9 μg of α-toxin in PBS. Solutions were then incubated for an additional 30 min with 1.8 mL of 5% purified mouse RBCs. Following the incubation, each sample was spun down at 14,000 rpm in a Beckman Coulter Microfuge® 22R Centrifuge for 10 min. The absorbance of the hemoglobin in the supernatant was analyzed at 540 nm using a Tecan Infinite M200 Multiplate Reader to assay for the degree of RBC lysis. Experiments were performed in triplicate.

RBC Nanosponges Binding Study

9 μg of α-toxin was incubated for 30 min with 200 μL PBS solutions containing 1 mg/mL of RBC nanosponges, PEGylated PLGA nanoparticles, PEGylated liposomes, and RBC membrane vesicles. After incubation, the samples were filtered through a Sepharose® CL-4B size-exclusion column to remove unbound toxin. The samples were then lyophilized and prepared in SDS sample buffer (Invitrogen). 9 μg of pure α-toxin was prepared alongside the filtered samples as a reference. The prepared samples were separated on a 4-12% Bis-Tris 10-well minigel in MOPS running buffer using a Novex® XCell SureLock Electrophoresis System (Invitrogen). The samples were run at 200 V for 50 min, and the resulting polyacrylamide gel was stained in SimplyBlue (Invitrogen) overnight for visualization. To quantify the toxin retention, the band intensity at 34 kDa was analyzed using ImageJ with toxin standard prepared from 0.3, 1, 3, and 9 μg of pure α-toxin.

α-Toxin Titration Study

200 μL of 1 mg/mL nanosponges in PBS was incubated for 30 min with 30, 9, 3.6, 1.2, 0.6, and 0.3 μg of α-toxin. As a control group, solutions containing the same concentrations of α-toxin were also prepared in the absence of the nanosponges. The sample and the control solutions were then incubated with 1.8 mL of 5% mouse RBC in PBS for 30 min. Each sample was spun down at 14,000 rpm for 10 min. The absorbance of the hemoglobin in the supernatant was analyzed at 540 nm to assay for the degree of RBC lysis. Experiments were performed in triplicate.

Nanosponges Titration Study

PBS solutions were prepared to contain various amounts of toxin nanosponges at 200, 60, 20, 6, and 2 μg. Each nanosponge solution was mixed with 9 μg of α-toxin in PBS and diluted to a final volume of 200 μL. Following 30 min of incubation, the solutions were added to 1.8 mL of 5% mouse RBC in PBS and incubated for 30 min. The solution was then spun down at 14,000 rpm for 10 min. The absorbance of the hemoglobin in the supernatant was analyzed at 540 nm to assay for the degree of RBC lysis. Experiments were performed in triplicate.

Cellular Uptake of RBC Nanosponges

To examine the membrane materials of the nanosponges and of the RBC membrane vesicles following cellular uptake, 10 μg of DMPE-rhodamine (Avanti Polar Lipids) was added to the RBC ghosts derived from 1 mL of whole blood prior to mechanical extrusion into membrane vesicles. The resulting dye-loaded RBC membrane vesicles were used to prepare the nanosponges. The fluorescent nanosponges and membrane vesicles were incubated for 1 hour with Human Umbilical Vein Endothelial Cells (HUVEC) (ATCC #CRL-1730) at a concentration of 300 μg/mL in Medium 199 with Hanks' BSS, with L-glutamine, HEPES, and 1.4 g/L $NaHCO_3$(Lonza) supplemented with 100 U/mL Penicillin with 100 μg/mL Streptomycin (Invitrogen) and 50 μg/mL Endothelial Cell Growth Supplement (Biomedical Technologies, Inc.). The media was then aspirated and the cells were incubated in fresh media for 1 h. Following the second incubation period, the cells were washed with PBS, fixed with 10% formalin (Millipore), and mounted with DAPI-containing Vectashield® (Invitrogen). The cells were imaged using a 60× oil immersion objective on an Applied Precision Delta Vision Deconvolution Scanning Fluorescence Microscope.

Toxin Neutralization Through Subcutaneous Route

RBC nanosponges were incubated with α-toxin at a final concentration of 0.67 mg/mL nanosponge and 12 μg/mL α-toxin in PBS for 15 min. A volume of 150 μL of the mixture was then injected subcutaneously into the flank region of 6 week-old female nu/nu nude mice (Charles River Laboratories). At day 3 after the injections the mice were imaged. Skin and muscles samples were cut at 5 μm and stained using H&E for histology.

Toxin Neutralization Through Systemic Route

RBC nanosponges at a concentration 20 mg/mL and α-toxin at a concentration of 60 μg/mL were prepared beforehand in distilled water. For the pre-inoculation studies, 6 week-old male ICR mice were injected intravenously through the tail vein with 80 mg/kg (dose per body weight) of the nanosponges followed by a 75 μg/kg injection of α-toxin 2 min later. For the post-inoculation studies, 6 week-old male ICR mice were injected first with 75 μg/kg of α-toxin followed by 80 mg/kg of nanosponge 2 min later. The controls were injected with 75 μg/kg of α-toxin solution only. The sample size for each group was 9.

1. A. E. Clatworthy, E. Pierson, D. T. Hung, Targeting virulence: a new paradigm for antimicrobial therapy. *Nat Chem Biol* 3, 541 (September, 2007).
2. D. G. Beghini et al., Anti-sera raised in rabbits against crotoxin and phospholipase A2 from Crotalus durissus cascavella venom neutralize the neurotoxicity of the venom and crotoxin. *Toxicon* 44, 141 (August, 2004).
3. Z. Chen et al., Potent neutralization of anthrax edema toxin by a humanized monoclonal antibody that competes with calmodulin for edema factor binding. *Proc Natl Acad Sci U SA* 106, 13487 (Aug. 11, 2009).
4. W. W. Kum, A. W. Chow, Inhibition of staphylococcal enterotoxin A-induced superantigenic and lethal activities by a monoclonal antibody to toxic shock syndrome toxin-1. *J Infect Dis* 183, 1739 (Jun. 15, 2001).
5. C. C. McCormick, A. R. Caballero, C. L. Balzli, A. Tang, R. J. O'Callaghan, Chemical inhibition of alpha-toxin, a key corneal virulence factor of *Staphylococcus aureus. Invest Ophthalmol Vis Sci* 50, 2848 (June, 2009).
6. D. T. Hung, E. A. Shakhnovich, E. Pierson, J. J. Mekalanos, Small-molecule inhibitor of *Vibrio cholerae* virulence and intestinal colonization. *Science* 310, 670 (Oct. 28, 2005).
7. Y. Hoshino et al., The rational design of a synthetic polymer nanoparticle that neutralizes a toxic peptide in vivo. *Proc Natl Acad Sci USA* 109, 33 (Jan. 3, 2012).
8. Y. Hoshino et al., Recognition, neutralization, and clearance of target peptides in the bloodstream of living mice by molecularly imprinted polymer nanoparticles: a plastic antibody. *J Am Chem Soc* 132, 6644 (May 19, 2010).
9. R. J. Gilbert, Pore-forming toxins. *Cell Mol Life Sci* 59, 832 (May, 2002).
10. C. J. Rosado et al., The MACPF/CDC family of pore-forming toxins. *Cell Microbiol* 10, 1765 (September, 2008).
11. J. Bubeck Wardenburg, O. Schneewind, Vaccine protection against Staphylococcus aureus pneumonia. *J Exp Med* 205, 287 (Feb. 18, 2008).
12. M. Shoham, Antivirulence agents against MRSA. *Future Med Chem* 3, 775 (May, 2011).
13. P. O'Hanley, G. Lalonde, G. Ji, Alpha-hemolysin contributes to the pathogenicity of piliated digalactoside-binding *Escherichia coli* in the kidney: efficacy of an alpha-hemolysin vaccine in preventing renal injury in the BALB/c mouse model of pyelonephritis. *Infect Immun* 59, 1153 (March, 1991).
14. B. T. Edelson, E. R. Unanue, Intracellular antibody neutralizes Listeria growth. *Immunity* 14, 503 (May, 2001).
15. B. T. Edelson, P. Cossart, E. R. Unanue, Cutting edge: paradigm revisited: antibody provides resistance to Listeria infection. *J Immunol* 163, 4087 (Oct. 15, 1999).
16. A. Nakouzi, J. Rivera, R. F. Rest, A. Casadevall, Passive administration of monoclonal antibodies to anthrolysin O prolong survival in mice lethally infected with *Bacillus anthracis. BMC Microbiol* 8, 159 (2008).
17. J. E. Alexander et al., Immunization of mice with pneumolysin toxoid confers a significant degree of protection against at least nine serotypes of *Streptococcus pneumoniae. Infect Immun* 62, 5683 (December, 1994).
18. L. A. Kirkham et al., Construction and immunological characterization of a novel nontoxic protective pneumolysin mutant for use in future pneumococcal vaccines. *Infect Immun* 74, 586 (January, 2006).
19. I. Andreeva-Kovalevskaya Zh, A. S. Solonin, E. V. Sineva, V. I. Ternovsky, Pore-forming proteins and adaptation of living organisms to environmental conditions. *Biochemistry* (*Mosc*) 73, 1473 (December, 2008).
20. G. Ma, Q. Cheng, Vesicular polydiacetylene sensor for colorimetric signaling of bacterial pore-forming toxin. *Langmuir* 21, 6123 (Jul. 5, 2005).
21. D. Pornpattananangkul et al., Bacterial toxin-triggered drug release from gold nanoparticle-stabilized liposomes for the treatment of bacterial infection. *J Am Chem Soc* 133, 4132 (Mar. 23, 2011).
22. D. Branton et al., The potential and challenges of nanopore sequencing. *Nat Biotechnol* 26, 1146 (October, 2008).
23. C. M. Hu, L. Zhang, S. Aryal, C. Cheung, R. H. Fang, Erythrocyte membrane-camouflaged polymeric nanoparticles as a biomimetic delivery platform. *Proc Natl Acad Sci USA* 108, 10980 (Jul. 5, 2011).
24. A. S. Klainer, M. A. Madoff, L. Z. Cooper, L. Weinstein, Staphylococcal Alpha-Hemolysin: Detection on the Erythrocyte Membrane by Immunofluorescence. *Science* 145, 714 (Aug. 14, 1964).

25. J. Chalmeau, N. Monina, J. Shin, C. Vieu, V. Noireaux, alpha-Hemolysin pore formation into a supported phospholipid bilayer using cell-free expression. *Biochim Biophys Acta* 1808, 271 (January, 2011).
26. M. Moorjani et al., Nanoerythrosomes, a new derivative of erythrocyte ghost II: identification of the mechanism of action. *Anticancer Res* 16, 2831 (September-October, 1996).
27. S. Vandana, M. Raje, M. V. Krishnasastry, The role of the amino terminus in the kinetics and assembly of alpha-hemolysin of *Staphylococcus aureus*. *J Biol Chem* 272, 24858 (Oct. 3, 1997).
28. A. Valeva et al., *J Biol Chem* 276, 14835 (May 4, 2001).
29. C. M. Hu, L. Zhang, S. Aryal, C. Cheung, R. H. Fang, *Proc Natl Acad Sci USA* 108, 10980 (Jul. 5, 2011).

Example 5

Cell Membrane-Coated Nanoparticles for Active Immunization of Toxins

Currently, the primary method in toxin vaccination is through the use of denatured toxins. This method, however, can be ineffective in neutralizing the toxin virulence and could disrupt the native structures that is imperative to the antigenicity of the toxin proteins. Genetically engineered toxins with reduced toxicity has been administered for toxin vaccination. These formulations, however, need to be tailored made toward specific toxin species and are be expensive to manufacture.

A toxin-neutralizing particle for safe toxin immunization is unique and was not previously described. Existing toxin immunization approaches entail either denaturation through heat or chemicals, which can influence the immunogenicity of the toxins, or engineered non-virulent proteins counterparts, which can be costly and cumbersome. The trade off between reducing toxin toxicity and preserving vaccine antigenicity has presented a significant challenge in toxin immunization. The present invention provides a major advantage over existing art as it is neutralizes toxin virulence without disrupting their native structures. It is easy to prepare and is applicable to a large number of toxin species.

Figure 23:
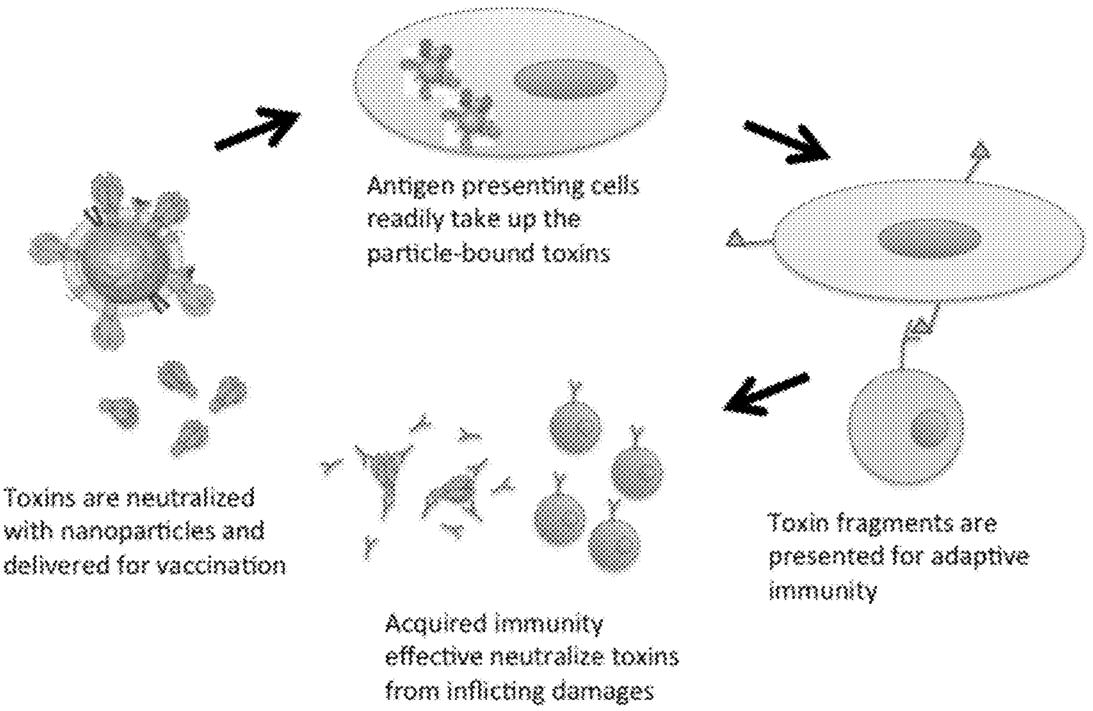
FIG. 23. Schematic illustration of membrane coated nanoparticles for active immunization of toxins.

Nanoparticles coated in cell membranes are used to as a platform to deliver antigens of interest for active immunization. It has been shown the membrane bilayer coated particle can absorb and detoxify bacterial toxins. These neutralized, particle-bound proteins are deprived of their virulence and yet retain their immunogenicity and are delivered in vivo to induce an immune response. This strategy is used to passivate toxins for active immunization, upon which the subject acquires the defense against the initial toxin target (FIG. 23). The technique treats a wide array of infections and diseases, including, but not limited to *Clostridium perfringens, Escherichia coli, Listeria monocytogenes, Bacillus anthracis, Streptococcus pneumoniae, Staphylococcus aureus*, and *Streptococcus pyogenes*. The submicron size of the particles make the platform readily uptaken by antigen-presenting cells.

Figure 24:
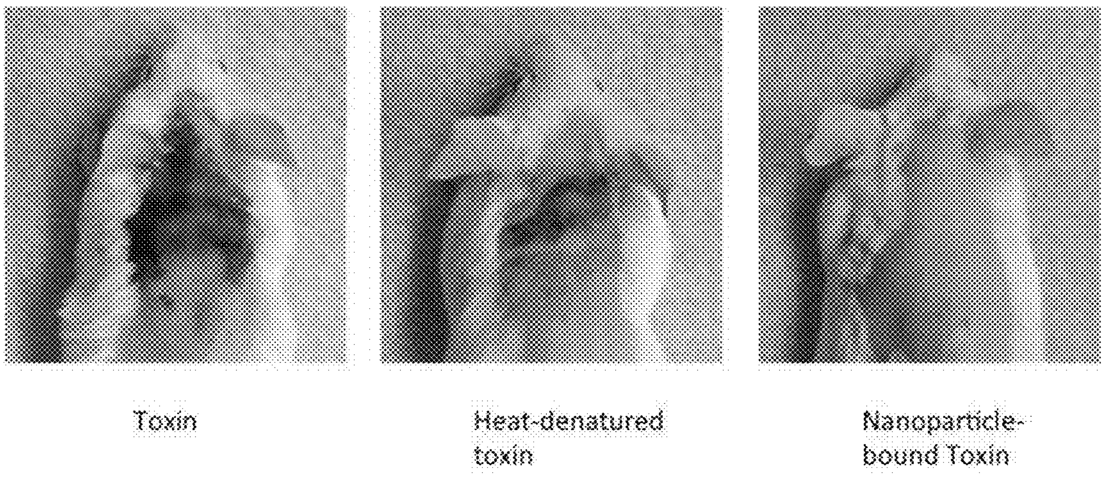
FIG. 24. Representative images of mice inoculated with either staphylococcal alpha-hemolysins, heat-denatured toxins, or nanoparticle-neutralized toxins subcutaneously in the neck region. 72 hours after the inoculation, the mice were examined and no skin lesions were observed on the particle/toxin inoculated mice.

Pore-forming toxins such as alpha-hemolysin from *Staphylococcus aureus* cause cellular damages by puncturing the cellular membranes. The toxin nanosponge described herein consisted of a polymeric core that is coated in the membrane materials of red blood cells. The membranes on the nanoparticles interact with toxins similarly to real cells. Once the toxins adhere to the nanosponges, they are locked in by the stable structure and therefore cannot inflict further damage (FIG. 24). The neutralize toxins retains their natural structure and conformation to induce adaptive immunity against the toxin target.

Figure 25:
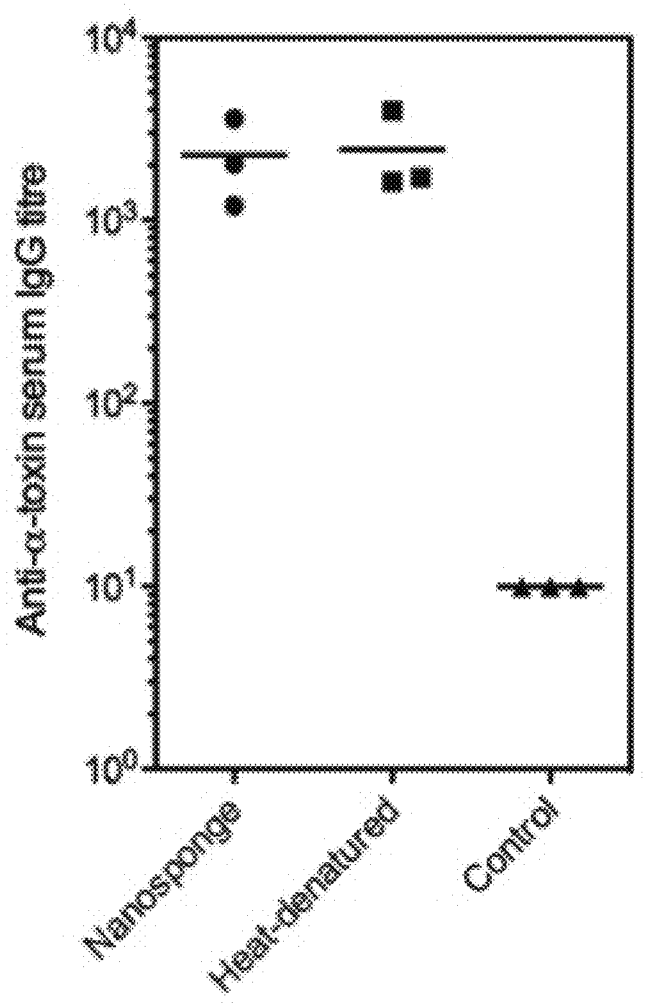
FIG. 25. Following 3 weekly inoculations of either the heat-denatured toxins or the nanoparticle-neutralized toxins, serum of inoculated mice were extracted and examined for antibody titres against alpha hemolysin using ELIZA. The nanoparticle/toxin group showed equivalent antibody titre to the heat-denatured toxin group.
Figure 26:
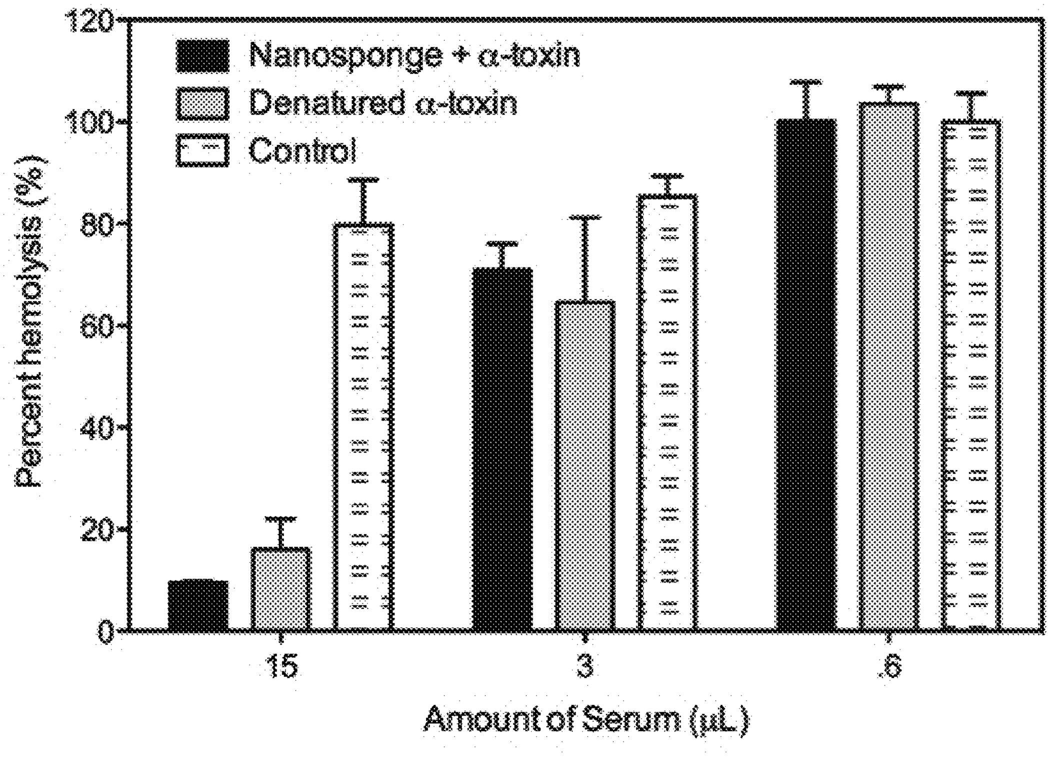
FIG. 26. Red blood cell hemolysis assay was conducted by first incubating toxins with dilutions of serum from the inoculated mice. The mixture was subsequently mixed with RBCs and examined for hemolytic activity. The serum from the nanoparticle/toxin inoculated mice showed significant inhibition of toxin activity.
Figure 27:
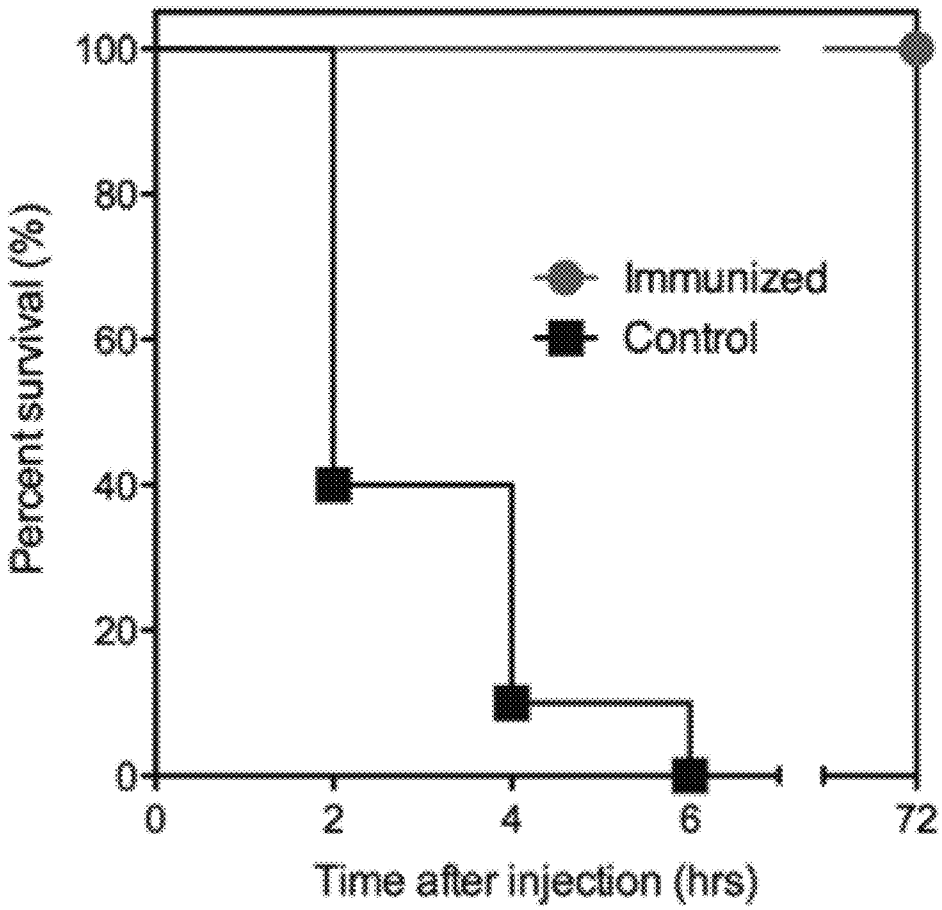
FIG. 27. Mice were inoculated with nanoparticle-neutralized alpha hemolysin weekly for 3 times prior to undergoing a toxin challenge in which a lethal dose of alpha hemolysins were injected intravenously. Non-immunized mice were injected with the same dose of toxin as a control. The particle/toxin immunized mice showed 100% survival at the 72 hour mark whereas the none of the non-immunized mice survived past the 6 hr mark (n=10).
Figure 28:
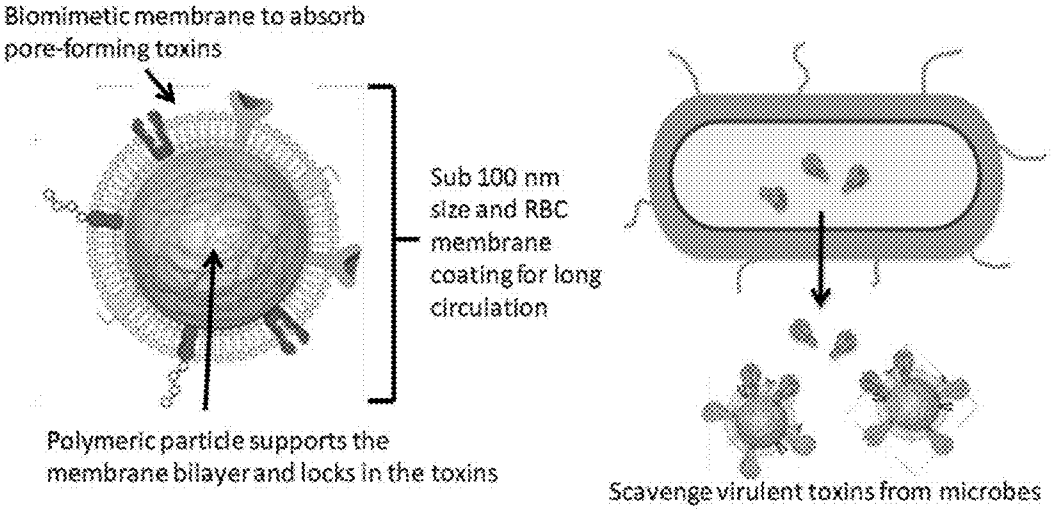
FIG. 28. Schematic illustration of membrane coated nanoparticles for toxin neutralization.

The present example provides cell membrane-coated nanoparticles for active immunization of toxins. Using nanoparticles prepared from red blood cells of mice and PLGA polymers, the inventors have successfully neutralized alpha hemolysins of *S. aureus* and delivered them subcutaneously in mice without inflicting any observable damages (FIG. 25). Upon 3 courses of inoculations with the particle/toxin formulation, the mice exhibit serum titre against the toxin target on the same level as those inoculated with heat-denatured toxin (FIG. 26). The inventors, thus, have demonstrated that the serum of particle/toxin immunized mice could inhibit the hemolytic activity of the alpha-hemolysins (FIG. 27). In a toxin challenge where a group of 10 mice were injected intravenously with a lethal dose of toxins, the particle/toxin immunized mice showed 100% survival whereas the none of the non-immunized mice survived past the 6 hr mark (FIG. 28).

Pore-forming toxins are the key virulence factors in many major infectious diseases, including but not limited to staph infection, pneumonia, anthrax, gas gangrene, and strep throat. The invention can be used as an toxin vaccination to treat or prevent these infections.

REFERENCES

Denatured Toxins for Immunization

1. Eaton M., "Chemical Modification of Purified Diphtheria Toxin." The Journal of Immunology. 1937 (33): 419-436.
2. Goshi K, Cluff L, Johnson J. "Studies on the Pathogenesis of Staphylococcal Infection." The Journal of Experimental Medicine. 1961, 113(2): 259-270.

Engineering Inactive Toxins for Immunization

1. Heveker N, Kiessig S T, Glaser R, Hungerer K D, Von Baehr R., "Anti-Alpha-Hemolysin Monoclonal Antibodies Mediate Protection against *Staphylococcus aureus* Pneumonia." Infection and Immunity. 2009, 77(7):2712-2718.
2. Wardenburg B, Schneewind O., "Vaccine protection against *Staphylococcus aureus* pneumonia." The Journal of Experimental Medicine. 2008, 205(2): 287-294.

Example 6

Platelet-Membrane-Coated Nanoparticles

Figure 29:
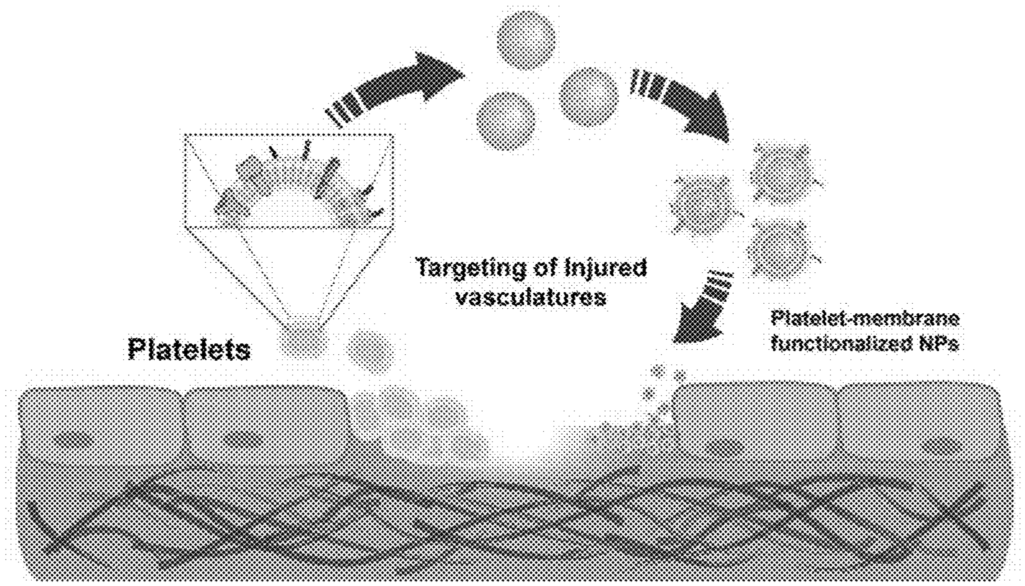
FIG. 29. Schematic of platelet-membrane-coated nanoparticles. Nanoparticles coated in platelet membranes are functionalized with platelet's immunoevasive properties and targeting properties to bind to diseased vasculatures.
Figure 30:
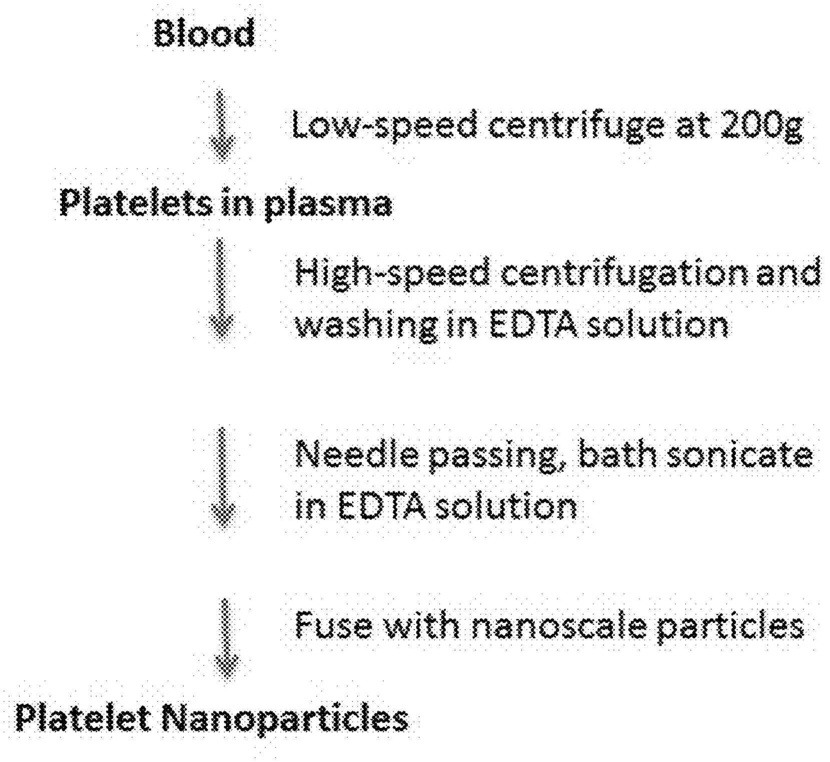
FIG. 30. Preparation process of platelet membrane coated nanoparticles. Platelets collected from blood were first washed and broken down to produce platelet membrane vesicles. The vesicles were then fused with nanoparticles to form platelet-membrane-coated nanoparticles.

Nanoparticles coated in platelet membranes are functionalized with platelet's immunoevasive properties and targeting properties to bind to diseased vasculatures. FIG. 29 illustrates a schematic of platelet-membrane-coated nanoparticles. Platelets collected from blood were first washed and broken down to produce platelet membrane vesicles. The vesicles were then fused with nanoparticles to form platelet-membrane-coated nanoparticles. A more detailed preparation process of platelet membrane coated nanoparticles is provided in FIG. 30.

Figure 31:
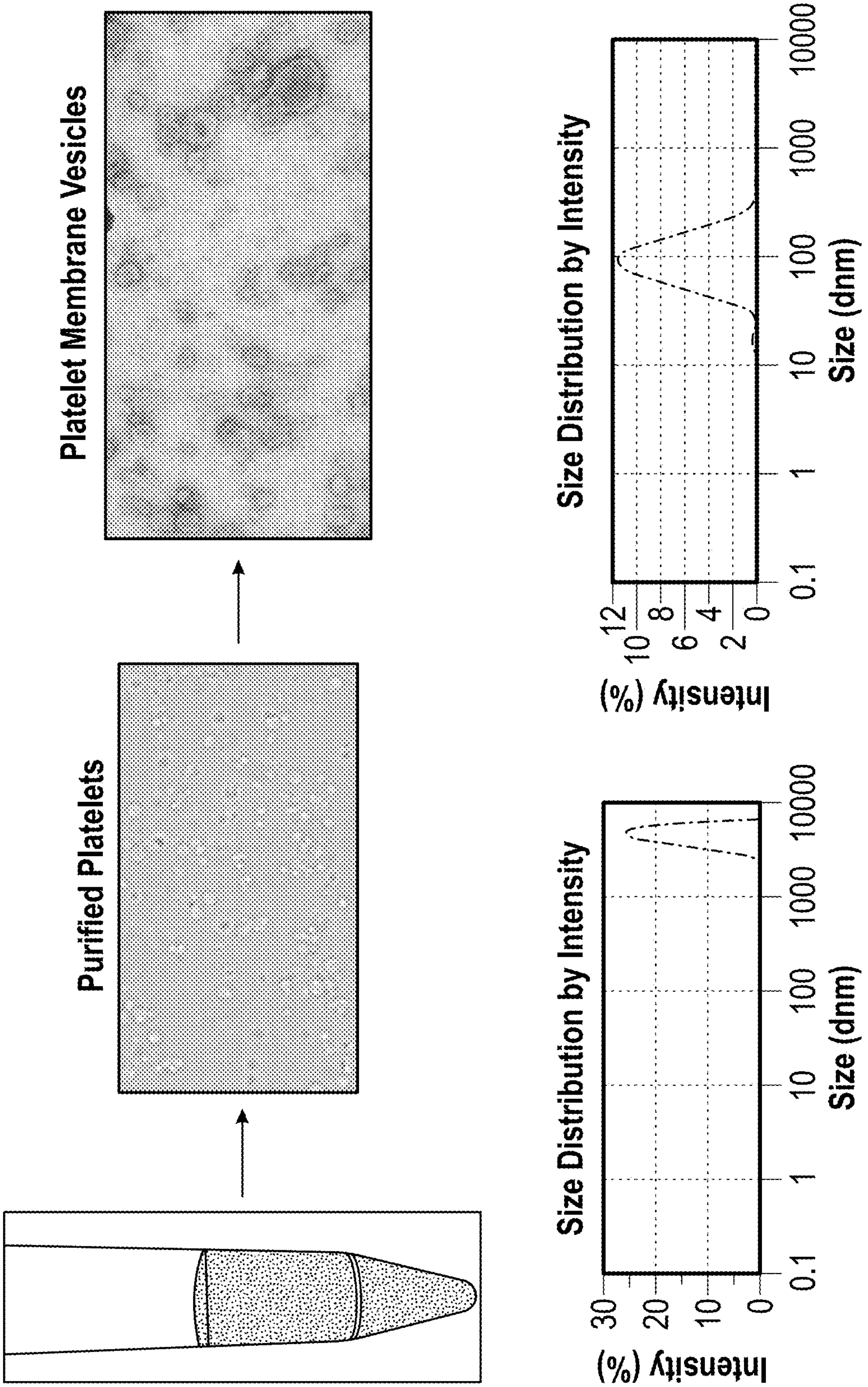
FIG. 31. Platelets isolated from whole blood were first purified to be rid of plasma content. The purified platelets can then be processed to form nanoscale membrane vesicles. Dynamic light scattering measurements showed that following platelet processing, micron-sized platelets can be turned into nanoscale platelet membrane vesicles.
Figure 32A:
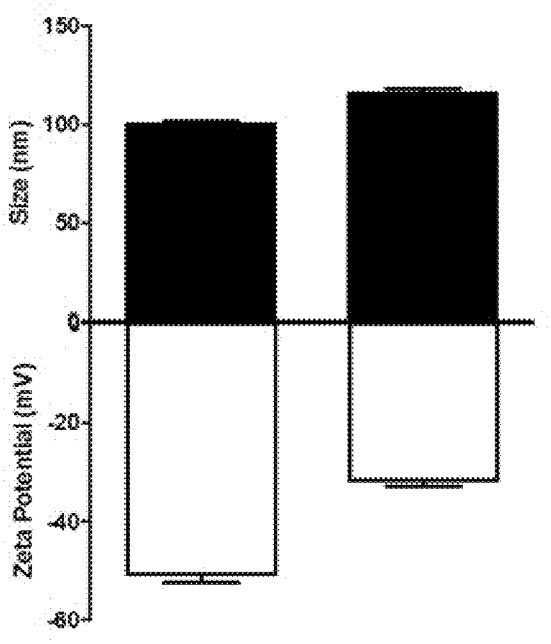
FIG. 32A Dynamic light scattering showed that the membrane coating increased the particle diameter by ~15 nm and reduced the surface charge.
Figure 32B:
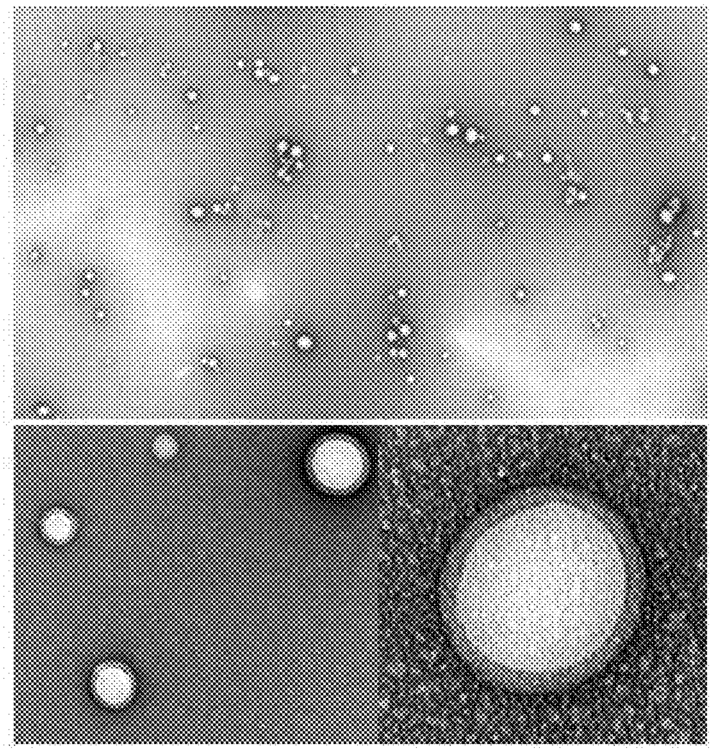
FIG. 32B Transmission electron microscopy showed the morphology of the platelet membrane coated nanoparticles. Individualized particulates were observed. The particles possess a clear core-shell structure with a unilamellar membrane coating ~7 nm in thickness.

Platelets isolated from whole blood were first purified to be rid of plasma content. The purified platelets can then be processed to form nanoscale membrane vesicles. Dynamic light scattering measurements showed that following platelet processing, micron-sized platelets can be turned into nanoscale platelet membrane vesicles (FIG. 31). In this example, 100 nm polymeric nanoparticles were coated with platelet membranes. Dynamic light scattering showed that the membrane coating increases the particle diameter by ~15 nm and reduced the surface charge (FIG. 32A). Transmission electron microscopy shows the morphology of the platelet membrane coated nanoparticles (FIG. 32B). Individualized particulates were observed, and the particles possess a clear core-shell structure with a unilamellar membrane coating ~7 nm in thickness (FIG. 32B).

Figure 33:
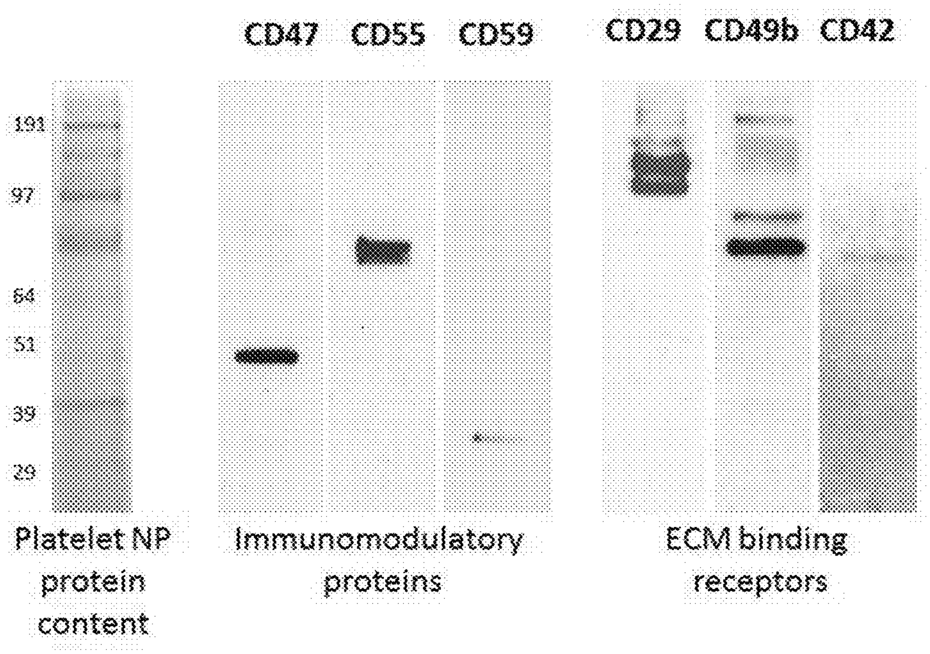
FIG. 33. Resolving the platelet nanoparticles (NPs) on an SDS-PAGE revealed that the particles are functionalized with membrane proteins from platelets. Identification of proteins on platelet NPs using western blotting confirmed the presence of immunomodulatory proteins (CD47, CD55, and CD59) and extracellular matrix binding receptors (CD29, CD49b, and CD42).
Figure 34:
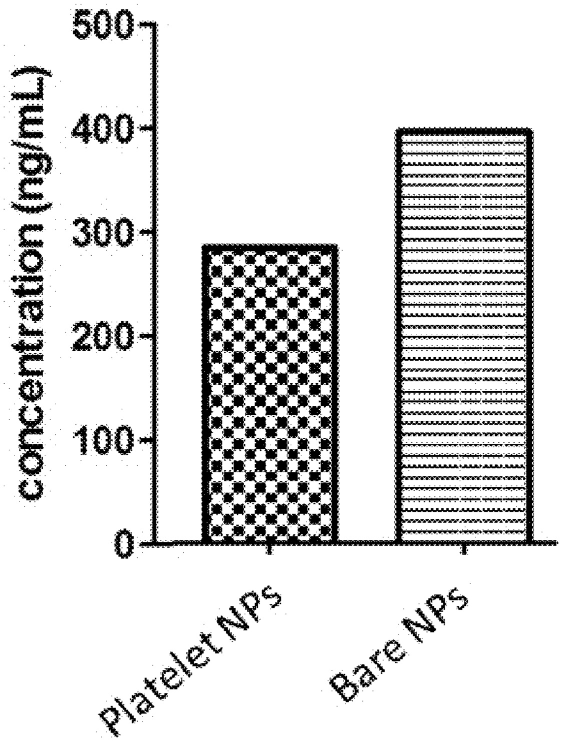
FIG. 34. In autologous plasma, platelet membrane coated NPs resulted in reduced complement activation as compared to bare uncoated NPs. The plasma and platelets were sourced from the same blood sample. Plasma/nanoparticle mixtures were examined for C4d content, which is a marker of classical complement activation.

Resolving the platelet nanoparticles (NPs) on an SDS-PAGE revealed that the particles are functionalized with membrane proteins from platelets (FIG. 33). Identification of proteins on platelet NPs using western blotting confirmed the presence of immunomodulatory proteins (CD47, CD55, and CD59) and extracellular matrix binding receptors (CD29, CD49b, and CD42) (FIG. 33). In autologous plasma, platelet membrane coated NPs resulted in reduced complement activation as compared to bare uncoated NPs (FIG. 34).

Figure 35:
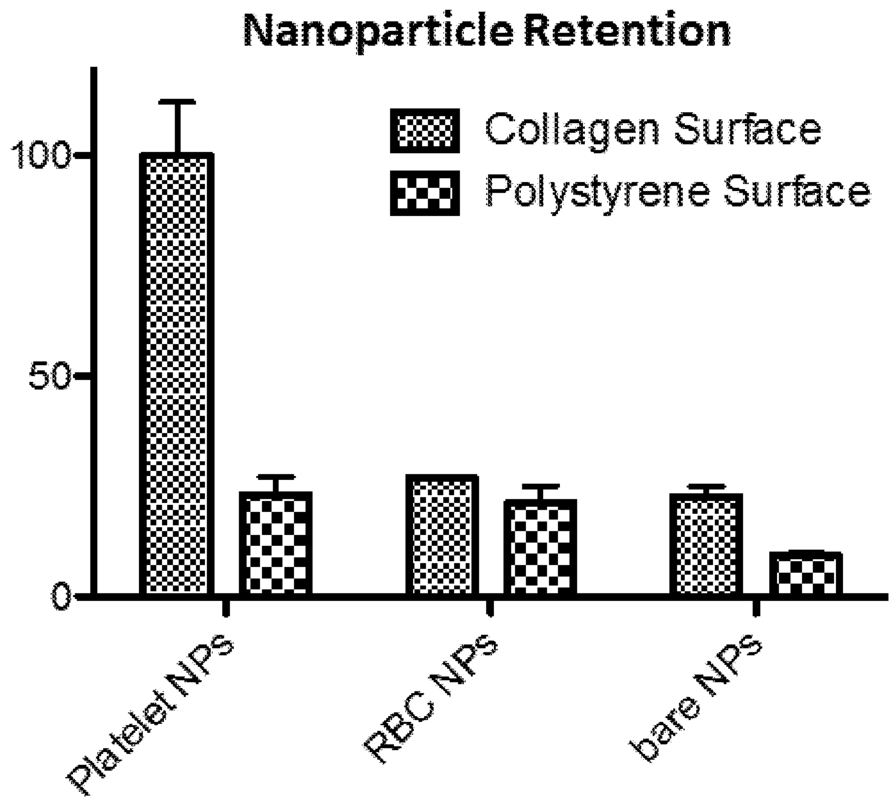
FIG. 35. Platelet membrane coated NPs showed preferential binding to collagen coated surfaces. Assay wells with either collagen or polystyrene surfaces were rinsed with different nanoparticle formulations with fluorescent labels. The wells were then washed and measured for retained particle fluorescence. Platelet membrane coated NPs showed strongly differential binding profiles between collagen and polystyrene surfaces as compared to red blood cell membrane coated nanoparticles and bare nanoparticles.
Figure 36A:
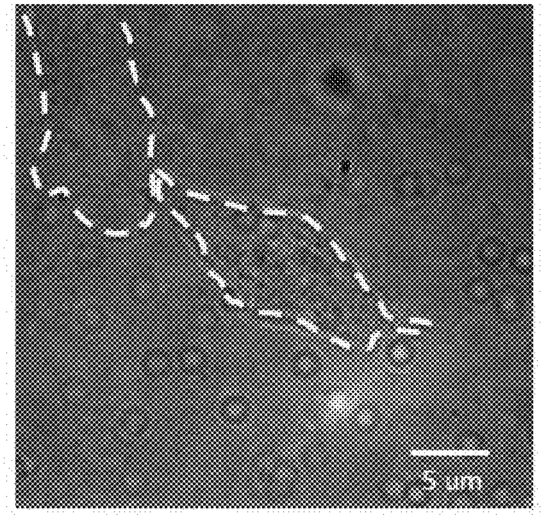
FIG. 36. Platelet membrane coated nanoparticles showed preferential binding to collagen surfaces over endothelial surfaces. Human umbilical vein endothelial cells cultured on collagen coated plates were rinsed with platelet membrane coated fluorescent nanoparticles. The resulting cells were imaged for FIG. 36A cell morphology, FIG. 36B particle (red greyscales) and cell nuclei (blue greyscales) fluorescence, and FIG. 36C particle fluorescence only.
FIG. 36D Particle fluorescence quantification over collagen and endothelial surfaces over 10 distinctive samples showed differential particle binding affinity.
Figure 36B:
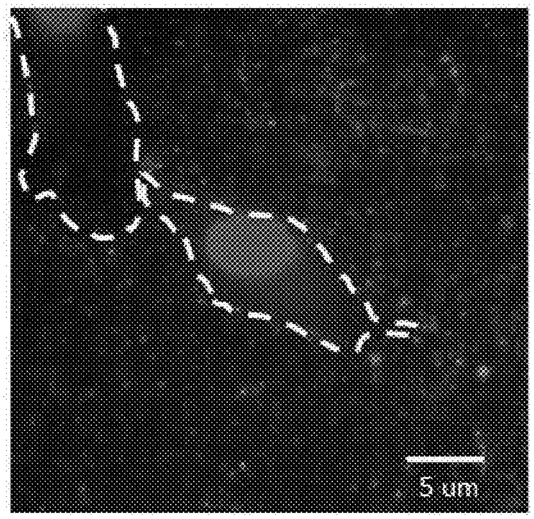
Figure 36C:
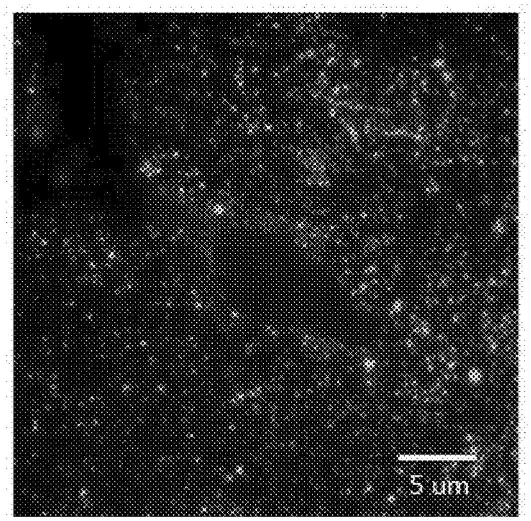
Figure 36D:
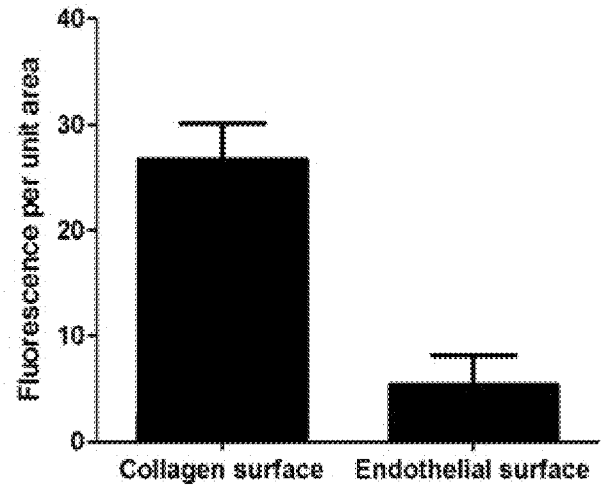

Platelet membrane coated nanoparticles further show preferential binding to collagen coated surfaces. Assay wells with either collagen or polystyrene surfaces were rinsed with different nanoparticle formulations with fluorescent labels. The wells were then washed and measured for retained particle fluorescence. Platelet membrane coated nanoparticles showed strongly differential binding profiles between collagen and polystyrene surfaces as compared to red blood cell membrane coated nanoparticles and bare nanoparticles (FIG. 35). Platelet membrane coated nanoparticles show preferential binding to collagen surfaces over endothelial surfaces. Human umbilical vein endothelial cells cultured on collagen coated plates were rinsed with platelet membrane coated fluorescent nanoparticles. The resulting cells were imaged for cell morphology, particle, and cell nuclei fluorescence, and particle fluorescence only (FIGS. 36A-C). Particle fluorescence quantification over collagen and endothelial surfaces over 10 distinctive samples showed differential particle binding affinity (FIG. 36D).

Figure 37:
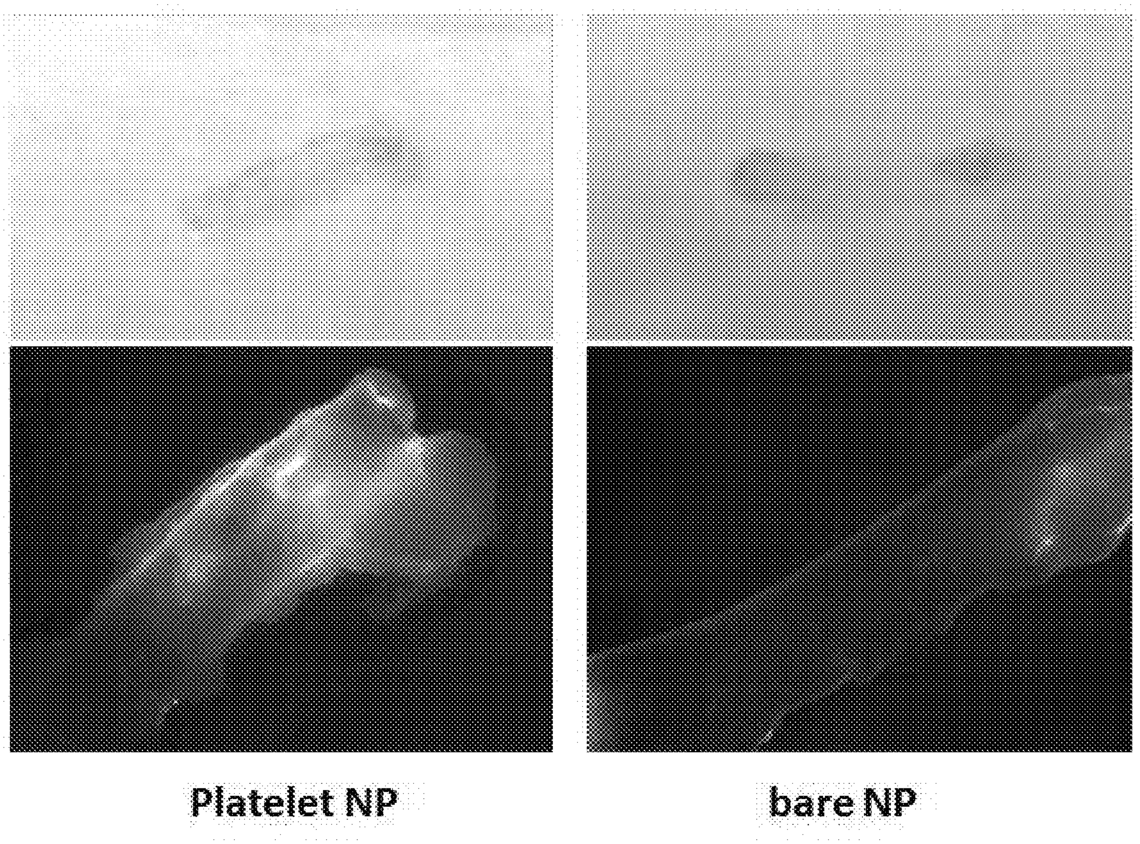
FIG. 37. Platelet membrane coated nanoparticles showed increased retention in denuded mice aorta. Dissected mice aorta was damaged and stripped of endothelial cells using a guide wire. Following flushing with platelet-membrane-coated nanoparticles or bare nanoparticles, the aorta showed higher retention of platelet-membrane-coated nanoparticles.
Figure 38:
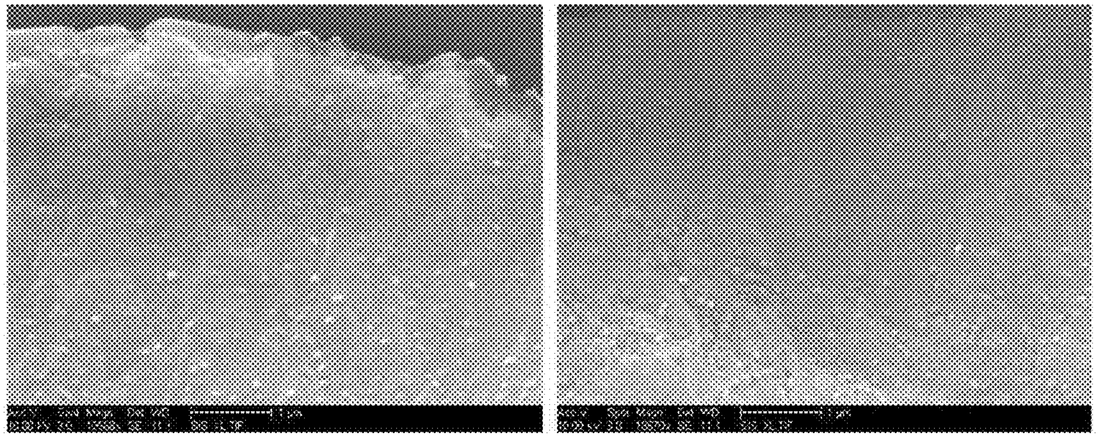
FIG. 38. Scanning electron microscopy showed binding of platelet-membrane-coated particles on decellularized mice aorta. Dissected mice aorta was first treated with sodium dodecyl sulfate solution to be rid of cellular content. The remaining matrices were rinsed with platelet membrane coated nanoparticle solution followed by PBS washes. Adhesion of the nanoparticles on the matrices was observed.

Platelet membrane coated nanoparticles also showed increased retention in denuded mice aorta. Dissected mice aorta was damaged and stripped of endothelial cells using a guide wire. Following flushing with platelet-membrane-coated nanoparticles or bare nanoparticles, the aorta showed higher retention of platelet-membrane-coated nanoparticles (FIG. 37). Scanning electron microscopy also showed binding of platelet-membrane-coated particles on decellularized mice aorta. Dissected mice aorta was first treated with sodium dodecyl sulfate solution to be rid of cellular content. The remaining matrices were rinsed with platelet membrane coated nanoparticle solution followed by PBS washes. Adhesion of the nanoparticles on the matrices was observed (FIG. 38).

Example 7

Bacterial-Membrane-Coated Nanoparticles

Figure 39A:
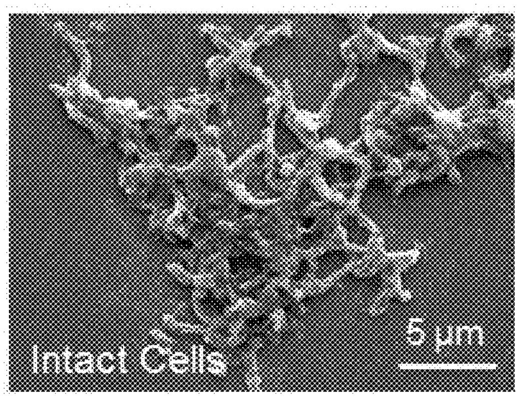
FIG. 39A Intact bacterial cells (*H. pylori*) used to collect membrane.
Figure 39B:
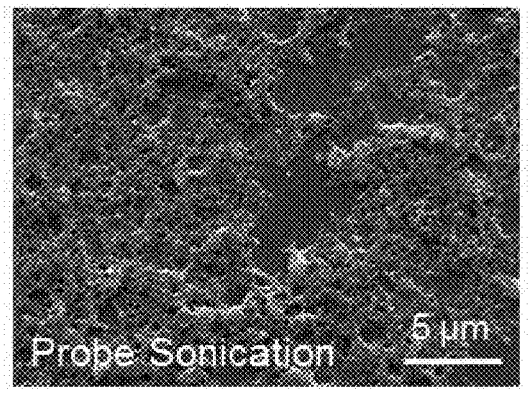
FIG. 39B Membrane derived by using probe sonication.
Figure 39C:
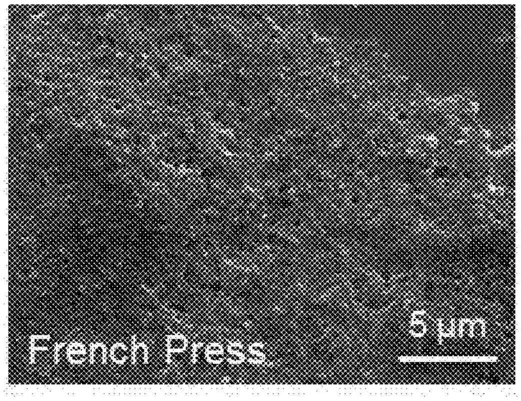
FIG. 39C Membrane collected by using French press.
Figure 39D:
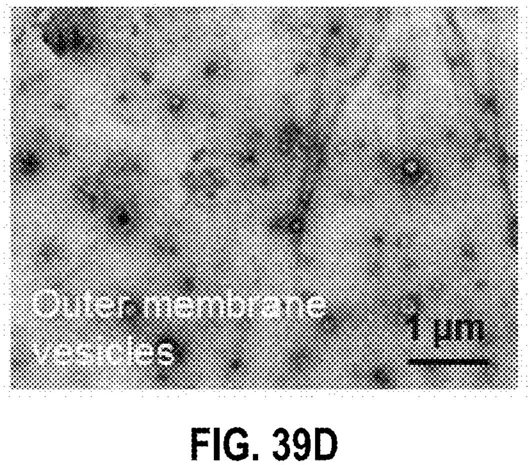
FIG. 39D Alternatively, outer membrane vesicles naturally shed from bacterial cells can be used.
Figure 40:
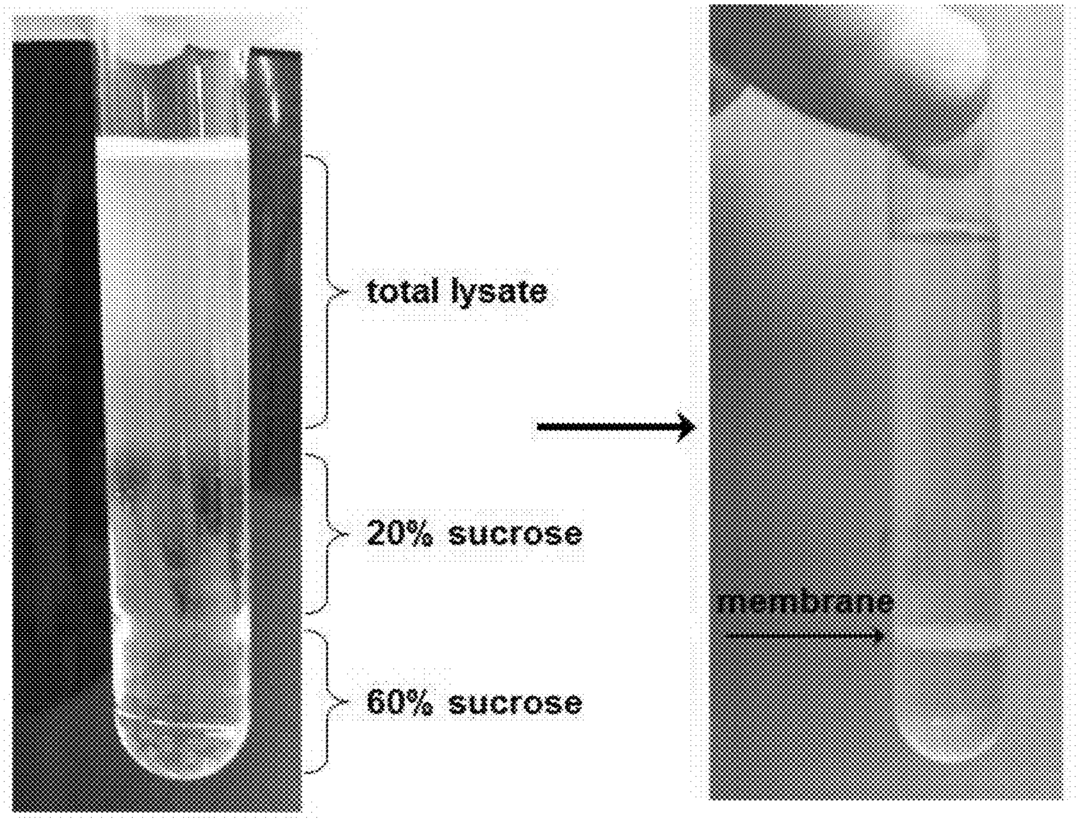
FIG. 40. The purification and concentration of bacterial membrane from cell lysate. Bacterial membrane (*H. pylori*) can be purified and concentrated by using conventional sucrose gradient.

This example provides bacterial-membrane-coated nanoparticles. Sources of bacterial membrane include intact bacterial cells (*H. pylori*) used to collect membrane (FIG. 39A), membrane derived by using probe sonication (FIG. 39B), and membrane collected by using French press (FIG. 39C). Alternatively, outer membrane vesicles naturally shed from bacterial cells can be used (FIG. 39D). Bacterial membrane (*H. pylori*) can be purified and concentrated by using conventional sucrose gradient. FIG. 40 illustrates the purification and concentration of bacterial membrane from cell lysate.

Figure 41A:
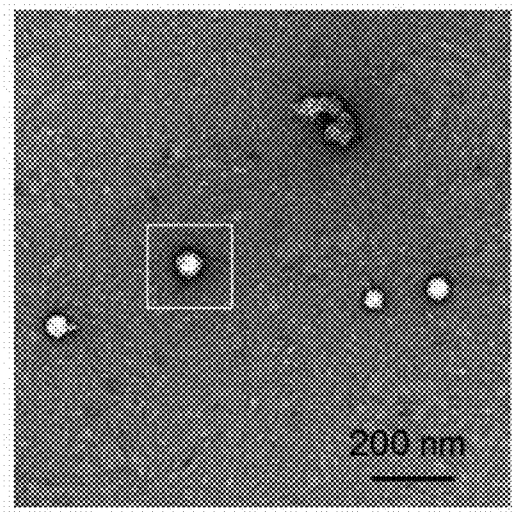
FIG. 41A. The TEM image showed PLGA nanoparticle cores with an average diameter of 70 nm are surrounded with a shell structure.
Figure 41B:
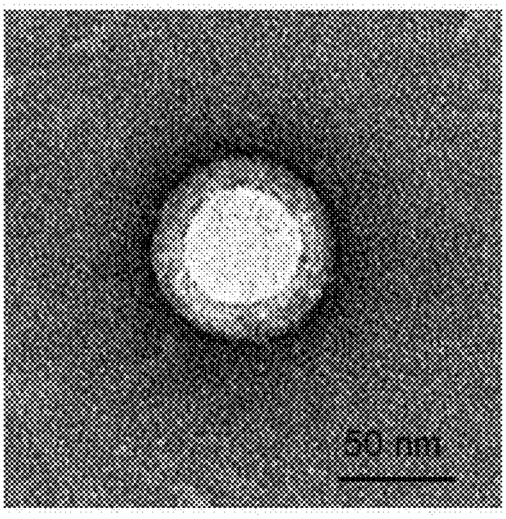
FIG. 41B. A zoom-in image resolved the shell structure with a thickness of 8 nm, corresponding to a lipid bilayer structure.
Figure 42:
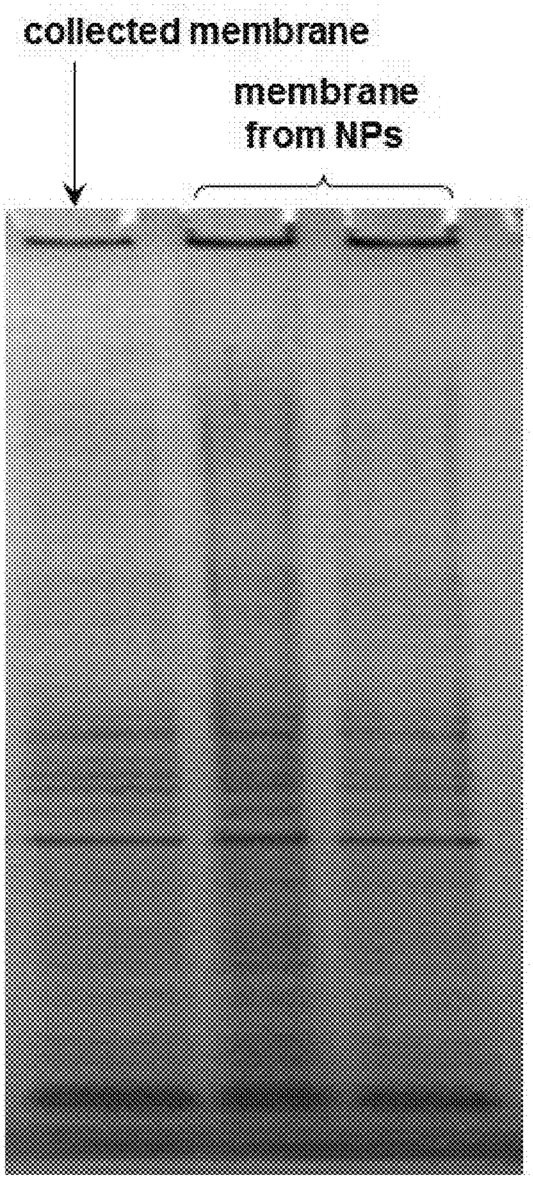
FIG. 42. Membrane of *H. pylori* coated onto polymeric nanoparticles has the similar protein profile to that of the membrane collected from bacteria, indicating that membrane coating retains membrane proteins.

Coating of polymeric nanoparticles with bacterial membrane derived from *H. pylori* was shown in FIG. 41A. The TEM image showed PLGA nanoparticle cores with an average diameter of 70 nm were surrounded with a shell structure (FIG. 41B). A zoom-in image resolves the shell structure with a thickness of 8 nm, corresponding to a lipid bilayer structure (FIG. 41). Membrane of *H. pylori* coated onto polymeric nanoparticles has the similar protein profile to that of the membrane collected from bacteria, indicating that membrane coating retains membrane proteins (FIG. 42).

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

TABLE 1

| Exemplary Cancers and Tumors |
|---|
| ackerman tumor |
| adenocarcinoid, malignant, appendiceal |
| adenocarcinoma variant, gastric cancer |
| adenocarcinoma, alpha-fetoprotein-producing, esophageal |
| adenocarcinoma, apocrine |
| adenocarcinoma, appendiceal |
| adenocarcinoma, bartholin gland |
| adenocarcinoma, bladder |
| adenocarcinoma, clear cell |
| adenocarcinoma, colloid |
| adenocarcinoma, ductal type |
| adenocarcinoma, eccrine |
| adenocarcinoma, endometrioid primary, in colorectal endometriosis |
| adenocarcinoma, esophagus |
| adenocarcinoma, fallopian tube |
| adenocarcinoma, fetal pulmonary |
| adenocarcinoma, gall bladder |
| adenocarcinoma, hepatoid |
| adenocarcinoma, in situ, cervix |
| adenocarcinoma, intra-extrahepatic, bile ducts |
| adenocarcinoma, lacrimal gland |
| adenocarcinoma, large bowel |
| adenocarcinoma, low-grade, extraosseous endolymphatic sac |
| adenocarcinoma, mucinous |
| adenocarcinoma, mucinous, prostate |
| adenocarcinoma, mucinous, stomach |
| adenocarcinoma, oncocytic |
| adenocarcinoma, pancreatic |
| adenocarcinoma, papillary, bladder |
| adenocarcinoma, pleomorphic |
| adenocarcinoma, polymorphous low-grade |
| adenocarcinoma, proximal jejunum |
| adenocarcinoma, rete testis |
| adenocarcinoma, small bowel |
| adenocarcinoma, thymus |
| adenocarcinoma, unknown primary site |
| adenocarcinoma, urachal |
| adenocarcinoma, urethral |
| adenocarcinoma, vaginal |
| adenomyoepithelioma, malignant, breast |
| adenosarcoma, Müllerian |
| adrenogenital syndrome/testicular tumor |

TABLE 1-continued

| Exemplary Cancers and Tumors |
| --- |
| ameloblastoma, desmoplastic |
| ameloblastoma, malignant |
| amyloid |
| angioblastoma, giant cell |
| angioendothelioma, malignant, endovascular papillary |
| angioendotheliomatosis, malignant |
| angiomyxoma, malignant, aggressive, scrotum |
| angiomyxoma, malignant, aggressive, scrotum |
| angiosarcoma |
| angiosarcoma, cardiac |
| angiosarcoma, pulmonary artery |
| angiosarcoma, Wilson-Jones |
| askin tumor |
| astroblastoma |
| astrocytic neoplasm |
| astrocytoma, anaplastic |
| astrocytoma, gemistocytic |
| astrocytoma, pilocytic |
| astrocytoma, thalamic glioma |
| blastoma, pleuropulmonary (PPB) |
| blastoma, pulmonary |
| borderline tumor, malignant, ovary |
| Buschke-Lowenstein tumor giant condyloma |
| calcifying epithelial odontogenic tumor (CEOT) |
| carcinamitosis, peritoneal |
| carcinoid, malignant |
| carcinoid, malignant, atypical |
| carcinoid, malignant, bronchopulmonary, atypical |
| carcinoid, malignant, bronchopulmonary, typical |
| carcinoid, malignant, colorectal |
| carcinoid, malignant, gastric |
| carcinoid, malignant, gastrointestinal, appendix |
| carcinoid, malignant, goblet cell |
| carcinoid, malignant, lung |
| carcinoid, malignant, pulmonary |
| carcinoid, malignant, rectal |
| carcinoid, malignant, renal |
| carcinoid, malignant, small bowel |
| carcinoid, malignant, thymic |
| carcinoma, acinar cell (ACC) |
| carcinoma, acinic cell |
| carcinoma, adenoid basal, uterine cervix |
| carcinoma, adenoid cystic (AdCC) |
| carcinoma, adenoid cystic, breast (ACCB) |
| carcinoma, adenoid cystic, breast, metastatic (ACC-M) |
| carcinoma, adenosquamous |
| carcinoma, adenosquamous, liver |
| carcinoma, adenosquamous, pancreatic |
| carcinoma, adrenocortical |
| carcinoma, ameloblastic |
| carcinoma, anal |
| carcinoma, anaplastic |
| carcinoma, anaplastic, thymic |
| carcinoma, anaplastic, thyroid |
| carcinoma, apocrine |
| carcinoma, basal cell, perianal |
| carcinoma, basal cell, vulva |
| carcinoma, basaloid squamous cell, esophageal |
| carcinoma, basaloid squamous cell, NOS |
| carcinoma, basaloid, lung |
| carcinoma, bile duct |
| carcinoma, biliary tract |
| carcinoma, bronchioalveolar (BAC) |
| carcinoma, bronchogenic small cell undifferentiated |
| carcinoma, choroid plexus |
| carcinoma, ciliated cell |
| carcinoma, clear cell, bladder |
| carcinoma, clear cell, eccrine |
| carcinoma, clear cell, odontogenic |
| carcinoma, clear cell, thymic |
| carcinoma, collecting duct (CDC) |
| carcinoma, collecting duct, kidney |
| carcinoma, cribriform |
| carcinoma, cribriform, breast |
| carcinoma, cystic |
| carcinoma, duodenal |
| carcinoma, epithelial-myoepithelial (EMC) |
| carcinoma, gall bladder |

TABLE 1-continued

| Exemplary Cancers and Tumors |
| --- |
| carcinoma, giant cell |
| carcinoma, hepatocellular |
| carcinoma, Hurthle cell |
| carcinoma, Hurthle cell, thyroid |
| carcinoma, insular |
| carcinoma, insular, thyroid |
| carcinoma, islet cell |
| carcinoma, large cell, neuroendocrine (LCNEC) |
| carcinoma, lymphoepithelioma-like, thymic |
| carcinoma, male breast |
| carcinoma, medullary thyroid |
| carcinoma, meibomian |
| carcinoma, merkel cell (MCC) |
| carcinoma, metaplastic, breast |
| carcinoma, microcystic adnexal |
| carcinoma, mixed acinar, endocrine |
| carcinoma, moderately differentiated, neuroendocrine |
| carcinoma, mucinous, bronchioloalveolar, lung |
| carcinoma, mucinous, eccrine |
| carcinoma, mucoepidermoid |
| carcinoma, mucoepidermoid, bronchus |
| carcinoma, nasopharyngeal/caucasians (NPC) |
| carcinoma, neuroendocrine |
| carcinoma, neuroendocrine, lung |
| carcinoma, non-small cell w/neuroendocrine features, lung |
| carcinoma, odontogenic |
| carcinoma, papillary |
| carcinoma, papillary, breast |
| carcinoma, parathyroid |
| carcinoma, parietal cell |
| carcinoma, penile |
| carcinoma, pilomatrix |
| carcinoma, pituitary |
| carcinoma, plasmacytoid urothelial, bladder |
| carcinoma, poorly differentiated, neuroendocrine (PDNEC) |
| carcinoma, primary intraosseous |
| carcinoma, primary peritoneal, extra-ovarian (EOPPC) |
| carcinoma, renal cell (RCC), poorly differentiated |
| carcinoma, renal cell (RCC), chromophobic (ChC) |
| carcinoma, renal cell (RCC), clear cell (CCC) |
| carcinoma, renal cell (RCC), collecting duct (CDC) |
| carcinoma, renal cell (RCC), papillary (PC) |
| carcinoma, renal cell (RCC), sarcomatoid |
| carcinoma, sarcomatoid, colon |
| carcinoma, sarcomatoid, thymic |
| carcinoma, sebaceous |
| carcinoma, serous ovarian, papillary(PsOC) |
| carcinoma, signet-ring cell |
| carcinoma, small cell |
| carcinoma, small cell undifferentiated, prostate |
| carcinoma, small cell undifferentiated, prostrate (SCUUP) |
| carcinoma, small cell, anorectal neuroendocrine |
| carcinoma, small cell, colorectal |
| carcinoma, small cell, esophageal |
| carcinoma, small cell, extrapulmonary |
| carcinoma, small cell, gastrointestinal tract |
| carcinoma, small cell, neuroendocrine (oat cell) (SCNC) |
| carcinoma, small cell, pancreatic |
| carcinoma, small cell, renal |
| carcinoma, small cell, stomach |
| carcinoma, small cell, thymic |
| carcinoma, small intestine |
| carcinoma, squamous cell, adnexal ductal cyst |
| carcinoma, squamous cell, atypical |
| carcinoma, squamous cell, breast |
| carcinoma, squamous cell, diffuse pagetoid, esophagus |
| carcinoma, squamous cell, esophageal |
| carcinoma, squamous cell, keratinizing, thymic (KTSC) |
| carcinoma, squamous cell, laryngeal |
| carcinoma, squamous cell, lymphoepithelioma-like |
| carcinoma, squamous cell, nasopharynx |
| carcinoma, squamous cell, nonkeratinizing |
| carcinoma, squamous cell, oral cavity |
| carcinoma, squamous cell, ovarian |
| carcinoma, squamous cell, stomach |
| carcinoma, squamous cell, subungual (SCC) |
| carcinoma, squamous cell, thymic |
| carcinoma, squamous cell, thyroglossal duct cyst (TGDC) |

TABLE 1-continued

| Exemplary Cancers and Tumors |
| --- |
| carcinoma, squamous cell, thyroid |
| carcinoma, squamous cell, urethra |
| carcinoma, squamous cell, vagina |
| carcinoma, squamous cell, vulvar |
| carcinoma, terminal duct |
| carcinoma, testicular |
| carcinoma, transitional cell |
| carcinoma, transitional cell, prostate |
| carcinoma, trichilemmal |
| carcinoma, tubal |
| carcinoma, tubular, breast |
| carcinoma, undifferentiated, nasopharyngeal type (UCNT) |
| carcinoma, undifferentiated, primary sinonasal nasopharyngea |
| carcinoma, undifferentiated, sinonasal (SNUC) |
| carcinoma, undifferentiated, thymic |
| carcinoma, undifferentiated, w/lymphoid stroma |
| carcinoma, vaginal |
| carcinoma, verrucous |
| carcinoma, w/spindle cell metaplasia, breast |
| carcinoma, w/metaplasia, osteo-chondroid variant, breast |
| carcinoma, w/sarcomatous metaplasia, breast |
| carcinoma, well differentiated, neuroendocrine (WDNEC) |
| carcinoma, well differentiated, thymic (WDTC) |
| carcinosarcoma |
| carcinosarcoma, uterine |
| cartilage tumor |
| cartilaginous tumor, larynx |
| chemodectoma, malignant |
| chloroma |
| cholangio-carcinoma |
| cholangitis, primary sclerosing |
| chondroblastoma |
| chondroid syringoma, malignant (MCS) |
| chondroma, malignant, pulmonary (in Carney's triad) |
| chondrosarcoma |
| chondrosarcoma, acral synovial |
| chondrosarcoma, classic, primary intradural |
| chondrosarcoma, clear cell |
| chondrosarcoma, clear cell, larynx |
| chondrosarcoma, dural-based |
| chondrosarcoma, intracranial |
| chondrosarcoma, mesenchymal |
| chondrosarcoma, mysoid, extraskeletal |
| chordoma |
| chordoma, clivus |
| chordoma, familial |
| chordoma, intracranial cavity |
| chordoma, NOS |
| chordoma, perifericum |
| chordoma, sacrum |
| chordoma, skull base |
| chordoma, vertebrae |
| choriocarcinoma |
| choriocarcinoma, esophagus |
| choriocarcinoma, gastric |
| choriocarcinoma, ovary |
| choriocarcinoma, stomach |
| choriocarcinoma/male, primary, pulmonary |
| cutaneous malignant tumor |
| cylindroma, malignant |
| cylindroma, malignant, apocrine |
| cystadenocarcinoma, acinar cell |
| cystadenocarcinoma, mucinous |
| cystadenocarcinoma, pancreatic |
| cystadenocarcinoma, serous |
| cystic-pseudopapillary tumor/pancreas |
| cystosarcoma phyllodes, malignant, breast |
| cystosarcoma phylloides |
| dermatofibrosarcoma protuberans (DFSP) |
| dermatofibrosarcoma protuberans, fibrosarcomatous variant |
| dermatofibrosarcoma protuberans, NOS |
| dermatofibrosarcoma protuberans, pigmented |
| desmoplastic, small round cell (DSRCT) |
| dysembryoplastic neuroepithelial tumor (DNT) |
| dysgerminoma |
| dysgerminoma, ovarian |
| eccrine poroma, malignant |
| eccrine spiradenoma, malignant |

TABLE 1-continued

| Exemplary Cancers and Tumors |
| --- |
| ectomesenchymoma, malignant |
| emlanoma, malignant, placenta |
| endocrine tumor, pancreatic |
| endodermal sinus tumor |
| endometrioid tumor, ovary |
| ependymoma |
| epithelial cancer, ovarian (EOC) |
| epithelial tumor, appendiceal |
| epithelial tumor, oral cavity |
| epithelioma cuniculatum |
| erythroleukemia |
| esthesioneuroblastoma |
| fibrosarcoma |
| fibrous histiocytoma, malignant |
| fibrous histiocytoma, malignant (MFH) |
| fibrous histiocytoma, malignant, angiomatoid |
| fibrous histiocytoma, malignant, intracerebral |
| fibrous histiocytoma, malignant, renal |
| fibrous tissue tumor, malignant |
| fibrous tumor, solitary, malignant |
| fibroxanthoma, atypical |
| follicular tumor |
| ganglioneuroblastoma |
| gastrointestinal autonomic nerve tumor |
| germ cell tumor |
| germ cell tumor, intracranial (GCTs) |
| germ cell tumor, ovarian |
| germ cell tumor, testicular (GCTS) |
| germinoma (seminoma) |
| germinoma, pineal |
| gestational trophoblastic tumor |
| giant cell tumor, nonendocrine |
| glioblastoma multiforme, spinal chord |
| glioblastoma, giant cell |
| glioma |
| glioma, optic nerve |
| glomangiosarcoma |
| glomus tumor, malignant |
| glucagonoma syndrome |
| granular cell tumor, malignant |
| granular cell tumor, malignant, larynx |
| granulosa cell tumor, ovary |
| granulosa tumor, stromal cell |
| gynandroblastoma |
| hamartoma, mesenchymal, liver (MHL) |
| hemangioendothelioma |
| hemangioendothelioma, epithelioid |
| hemangioendothelioma, spindle cell |
| hemangioendothelioma, thyroid |
| hemangioendotheliomas, epithelioid, pulmonary (PEH) |
| hemangiopericytoma (HEPC) |
| hemangiosarcoma |
| hepatoblastoma |
| hereditary non-polyposis colorectal cancer (HNPCC) |
| hidradenoma papilliferum, malignant |
| histiocytoma |
| histiocytosis, malignant |
| Hodgkin's disease |
| Hodgkin's disease, bladder |
| Hodgkin's disease, blood |
| Hodgkin's disease, bone |
| Hodgkin's disease, bone marrow |
| Hodgkin's disease, breast |
| Hodgkin's disease, cardiovascular system |
| Hodgkin's disease, central nervous system |
| Hodgkin's disease, connective tissue disease |
| Hodgkin's disease, endocrine system |
| Hodgkin's disease, gastrointestinal tract |
| Hodgkin's disease, genitourinary |
| Hodgkin's disease, head & neck |
| Hodgkin's disease, kidney |
| Hodgkin's disease, lung |
| Hodgkin's disease, muscle |
| Hodgkin's disease, neurological system |
| Hodgkin's disease, prostate |
| Hodgkin's disease, reproductive system |
| Hodgkin's disease, respiratory system |
| Hodgkin's disease, skin |

TABLE 1-continued

| Exemplary Cancers and Tumors |
|---|
| Hodgkin's disease, testis |
| Hodgkin's disease, thymus |
| Hodgkin's disease, thyroid |
| hypokalemia & achlorhydria syndrome, well differentiated |
| inflammatory myofibroblastic tumor (IMT) |
| inflammatory myofibroblastic tumor (IMT), pulmonary |
| insular papillary cancer, thyroid |
| insulinoma, malignant |
| islet cell tumor, nonfunctioning |
| islet cell, pancreatic |
| Krukenberg |
| Langerhans Cell Histiocytosis (LCH) |
| leiomyoblastoma |
| leiomyomatosis, intravenous |
| leiomyosarcoma |
| leiomyosarcoma, adrenal |
| leiomyosarcoma, epithelioid, gastric leiomyosarcoma, gastric epithelioid |
| leiomyosarcoma, esophagus |
| leiomyosarcoma, lung |
| leiomyosarcoma, oral cavity |
| leiomyosarcoma, pancreas |
| leiomyosarcoma, primary bone (PLMSB) |
| leiomyosarcoma, renal |
| leiomyosarcoma, superficial perineal |
| leiomyosarcoma, uterine |
| leiomyosarcoma, vulva |
| leukemia, acute erythroblastic (FAB M6) |
| leukemia, acute lymphocytic (ALL) |
| leukemia, acute monocytic |
| leukemia, acute myeloid (AML) |
| leukemia, acute nonlymphocytic (ANLL) |
| leukemia, acute nonlymphoblastic |
| leukemia, acute undifferentiated (AUL) |
| leukemia, adult T-cell |
| leukemia, basophilic |
| leukemia, central nervous system |
| leukemia, chronic lymphocytic (CLL) |
| leukemia, chronic myelogenous (CML) |
| leukemia, cutis |
| leukemia, eosinophilic |
| leukemia, extramedullary |
| leukemia, hairy cell (HCL) |
| leukemia, Hodgkin's cell |
| leukemia, lymphoblastic, t-cell, acute (ALL) |
| leukemia, prolymphocytic, t-cell |
| leukemia, promyelocytic |
| Leydig cell tumor (LCT) |
| lipoastrocytoma |
| lipoblastoma |
| liposarcoma |
| liposarcoma, larynx |
| liposarcoma, myxoid |
| liposarcoma, pleomorphic |
| liposarcoma, primary mesenteric |
| liposarcoma, renal |
| liposarcoma, well-differentiated |
| low malignant potential tumor, ovary (LMP) |
| lymphoepithelioma, parotid gland |
| lymphoma, adrenal |
| lymphoma, angiocentric |
| lymphoma, angiotropic large cell |
| lymphoma, B-cell |
| lymphoma, B-cell, low grade, liver |
| lymphoma, B-cell, salivary gland |
| lymphoma, bladder |
| lymphoma, bone |
| lymphoma, breast |
| lymphoma, breast, MALT-type |
| lymphoma, Burkitt's |
| lymphoma, cardiovascular system |
| lymphoma, central nervous system |
| lymphoma, cervix |
| lymphoma, chest wall |
| lymphoma, colorectal mucosa associated lymphoid tumor |
| lymphoma, cutaneous B cell |
| lymphoma, cutaneous T cell (CTCL) |
| lymphoma, diffuse large cell |

TABLE 1-continued

| Exemplary Cancers and Tumors |
|---|
| lymphoma, duodenal |
| lymphoma, endocrine |
| lymphoma, esophageal |
| lymphoma, follicular |
| lymphoma, gall bladder |
| lymphoma, gastrointestinal tract |
| lymphoma, genital tract |
| lymphoma, head & neck |
| lymphoma, heart |
| lymphoma, hepatobilliary |
| lymphoma, HIV-associated |
| lymphoma, intravascular |
| lymphoma, Ki-1 positive, anaplastic, large cell |
| lymphoma, kidney |
| lymphoma, large bowel |
| lymphoma, large cell, anaplastic |
| lymphoma, larynx |
| lymphoma, lung |
| lymphoma, lymphoblastic (LBL) |
| lymphoma, MALT |
| lymphoma, mantle cell |
| lymphoma, mediterranean |
| lymphoma, muscle |
| lymphoma, nasal |
| lymphoma, neurological system |
| lymphoma, non-Hodgkin's (NHL) |
| lymphoma, non-Hodgkin's, breast |
| lymphoma, non-Hodgkin's, extranodal localization |
| lymphoma, non-Hodgkin's, larynx |
| lymphoma, non-Hodgkin's, pulmonary |
| lymphoma, non-Hodgkin's, testis |
| lymphoma, ocular |
| lymphoma, oral |
| lymphoma, orbital |
| lymphoma, ovary |
| lymphoma, pancreatic lymphoma, pancreas |
| lymphoma, paranasal sinus |
| lymphoma, penile |
| lymphoma, peripheral nervous system |
| lymphoma, pharynx |
| lymphoma, pituitary |
| lymphoma, primary breast |
| lymphoma, primary central nervous system |
| lymphoma, primary lung |
| lymphoma, prostate |
| lymphoma, pulmonary |
| lymphoma, renal |
| lymphoma, respiratory system |
| lymphoma, scrotum |
| lymphoma, skin |
| lymphoma, small bowel |
| lymphoma, small intestine |
| lymphoma, soft tissue |
| lymphoma, spermatic cord |
| lymphoma, stomach |
| lymphoma, t-cell (CTCL) |
| lymphoma, testicular |
| lymphoma, thyroid |
| lymphoma, trachea |
| lymphoma, ureter |
| lymphoma, urethra |
| lymphoma, urological system |
| lymphoma, uterus |
| lymphomatosis, intravascular |
| MALT tumor |
| medulloblastoma |
| melanoma, adrenal |
| melanoma, amelanotic |
| melanoma, anal |
| melanoma, anorectal |
| melanoma, biliary tree |
| melanoma, bladder |
| melanoma, brain |
| melanoma, breast |
| melanoma, cardiopulmonary system |
| melanoma, central nervous system |
| melanoma, cervix |
| melanoma, choroidal |

TABLE 1-continued

| Exemplary Cancers and Tumors |
|---|
| melanoma, conjunctival |
| melanoma, desmoplastic |
| melanoma, endocrine |
| melanoma, esophageal |
| melanoma, gall bladder |
| melanoma, gastrointestinal tract |
| melanoma, genitourinary tract |
| melanoma, head & neck |
| melanoma, heart |
| melanoma, intraocular |
| melanoma, intraoral |
| melanoma, kidney |
| melanoma, larynx |
| melanoma, leptomeningeal |
| melanoma, lung |
| melanoma, nasal mucosa |
| melanoma, oral cavity |
| melanoma, osteoid forming/osteogenic |
| melanoma, ovary |
| melanoma, pancreas |
| melanoma, paranasal sinuses |
| melanoma, parathyroid |
| melanoma, penis |
| melanoma, pericardium |
| melanoma, pituitary |
| melanoma, placenta |
| melanoma, prostate |
| melanoma, pulmonary |
| melanoma, rectum |
| melanoma, renal pelvis |
| melanoma, sinonasal |
| melanoma, skeletal system |
| melanoma, small bowel |
| melanoma, small intestine |
| melanoma, spinal cord |
| melanoma, spleen |
| melanoma, stomach |
| melanoma, testis |
| melanoma, thyroid |
| melanoma, ureter |
| melanoma, urethra |
| melanoma, uterus |
| melanoma, vagina |
| melanoma, vulva |
| meningioma, malignant, anaplastic |
| meningioma, malignant, angioblastic |
| meningioma, malignant, atypical |
| meningioma, malignant, papillary |
| mesenchymal neoplasm, stromal |
| mesenchymoma |
| mesoblastic nephroma |
| mesothelioma, malignant |
| mesothelioma, malignant, pleura |
| mesothelioma, papillary |
| mesothelioma/tunica vaginalis, malignant (MMTV) |
| microadenocarcinoma, pancreatic |
| mixed cell tumor, pancreatic |
| mixed mesodermal tumor (MMT) |
| mucosa-associated lymphoid tissue (MALT) |
| Müllerian tumor, malignant mixed, fallopian tube |
| Müllerian tumor, malignant mixed, uterine cervix |
| myeloma, IgM |
| myoepithelioma |
| myoepithelioma, malignant, salivary gland |
| nephroblastoma |
| neuroblastoma |
| neuroectodermal tumor, renal |
| neuroendocrine tumor, prostate |
| neurofibrosarcoma |
| nodular hidradenoma, malignant |
| oligodendroglioma |
| oligodendroglioma, anaplastic |
| oligodendroglioma, low-grade |
| osteosarcoma |
| Paget's disease, extramammary (EMPD) |
| Paget's disease, mammary |
| pancreatoblastoma |
| paraganglioma, malignant |

TABLE 1-continued

| Exemplary Cancers and Tumors |
|---|
| paraganglioma, malignant, extra-adrenal |
| paraganglioma, malignant, gangliocytic |
| paraganglioma, malignant, laryngeal |
| peripherial nerve sheath tumor, malignant (MPNST) |
| pheochromocytoma, malignant |
| phyllodes tumor, malignant, breast |
| pilomatrixoma, malignant |
| plasmacytoma, extramedullary (EMP) |
| plasmacytoma, laryngeal |
| plasmacytoma, solitary |
| pleomorphic adenoma, malignant |
| pleomorphic xanthoastrocytoma (PXA) |
| plexiform fibrohistiocytic tumor |
| polyembryoma |
| polypoid glottic tumor |
| primary lesions, malignant, diaphragm |
| primary malignant lesions, chest wall |
| primary malignant lesions, pleura |
| primary sinonasal nasopharyngeal undifferentiated (PSNPC) |
| primitive neuroectodermal tumor (PNET) |
| proliferating trichilemmal tumor, malignant |
| pseudomyxoma peritonei, malignant (PMP) |
| raniopharyngioma |
| reticuloendothelial tumor |
| retiforme hemangioendothelioma |
| retinoblastoma |
| retinoblastoma, trilateral |
| rhabdoid teratoma, atypical teratoid AT/RT |
| rhabdoid tumor, malignant |
| rhabdomyosarcoma (RMS) |
| rhabdomyosarcoma, orbital |
| rhabdomyosarcoma, alveolar |
| rhabdomyosarcoma, botryoid |
| rhabdomyosarcoma, central nervous system |
| rhabdomyosarcoma, chest wall |
| rhabdomyosarcoma, paratesticular (PTR) |
| sarcoma, adult prostate gland |
| sarcoma, adult soft tissue |
| sarcoma, alveolar soft part (ASPS) |
| sarcoma, bladder |
| sarcoma, botryoides |
| sarcoma, central nervous system |
| sarcoma, clear cell, kidney |
| sarcoma, clear cell, soft parts |
| sarcoma, dendritic cell, follicular |
| sarcoma, endometrial stromal (ESS) |
| sarcoma, epithelioid |
| sarcoma, Ewing's (EWS) |
| sarcoma, Ewing's, extraosseus (EOE) |
| sarcoma, Ewing's, primitive neuroectodermal tumor |
| sarcoma, fallopian tube |
| sarcoma, fibromyxoid |
| sarcoma, granulocytic |
| sarcoma, interdigitating reticulum cell |
| sarcoma, intracerebral |
| sarcoma, intracranial |
| sarcoma, Kaposi's |
| sarcoma, Kaposi's, intraoral |
| sarcoma, kidney |
| sarcoma, mediastinum |
| sarcoma, meningeal |
| sarcoma, neurogenic |
| sarcoma, ovarian |
| sarcoma, pituitary |
| sarcoma, pleomorphic soft tissue |
| sarcoma, primary, lung |
| sarcoma, primary, pulmonar (PPS) |
| sarcoma, prostate |
| sarcoma, pulmonary arterial tree |
| sarcoma, renal |
| sarcoma, respiratory tree |
| sarcoma, soft tissue |
| sarcoma, stromal, gastrointestinal (GIST) |
| sarcoma, stromal, ovarian |
| sarcoma, synovial |
| sarcoma, synovial, intraarticular |
| sarcoma, synovial, lung |
| sarcoma, true |

TABLE 1-continued

| Exemplary Cancers and Tumors |
|---|
| sarcoma, uterine |
| sarcoma, vaginal |
| sarcoma, vulvar |
| sarcomatosis, meningeal |
| sarcomatous metaplasia |
| schwannoma, malignant |
| schwannoma, malignant, cellular, skin |
| schwannoma, malignant, epithelioid |
| schwannoma, malignant, esophagus |
| schwannoma, malignant, nos |
| Sertoli cell tumor, large cell, calcifying |
| sertoli-Leydig cell tumor (SLCT) |
| small cell cancer, lung small cell lung cancer (SCLC) |
| solid-pseudopapillary tumor, pancreas |
| somatostinoma |
| spindle cell tumor |
| spindle epithelial tumour w/thymus-like element |
| spiradenocylindroma, kidney |
| squamous neoplasm, papillary |
| steroid cell tumor |
| Stewart-Treves syndrome |
| stromal cell tumor, sex cord |
| stromal cell, testicular |
| stromal luteoma |
| stromal myosis, endolymphatic (ESM) |
| stromal tumor, colorectal |
| stromal tumor, gastrointestinal (GIST) |
| stromal tumor, gonadal (sex cord) (GSTS) |
| stromal tumor, ovary |
| stromal tumor, small bowel |
| struma ovarii |
| teratocarcinosarcoma, sinonasal (SNTCS) |
| teratoma, immature |
| teratoma, intramedullary spine |
| teratoma, mature |
| teratoma, pericardium |
| teratoma, thyroid gland |
| thecoma stromal luteoma |
| thymoma, malignant |
| thymoma, malignant, medullary |
| thyroid/brain, anaplastic |
| trichoblastoma, skin |
| triton tumor, malignant, nasal cavity |
| trophoblastic tumor, fallopian tube |
| trophoblastic tumor, placental site |
| urethral cancer |
| vipoma (islet cell) |
| vulvar cancer |
| Waldenstrom's macroglobullinemia |
| Wilms' tumor Nephroblastoma |
| Wilms' tumor, lung |

TABLE 2

| Exemplary Cancer Medications |
|---|
| Abiraterone Acetate |
| Abitrexate (Methotrexate) |
| Adriamycin (Doxorubicin Hydrochloride) |
| Adrucil (Fluorouracil) |
| Afinitor (Everolimus) |
| Aldara (Imiquimod) |
| Aldesleukin |
| Alemtuzumab |
| Alimta (Pemetrexed Disodium) |
| Aloxi (Palonosetron Hydrochloride) |
| Ambochlorin (Chlorambucil) |
| Amboclorin (Chlorambucil) |
| Aminolevulinic Acid |
| Anastrozole |
| Aprepitant |
| Arimidex (Anastrozole) |
| Aromasin (Exemestane) |
| Arranon (Nelarabine) |
| Arsenic Trioxide |

TABLE 2-continued

| Exemplary Cancer Medications |
|---|
| Arzerra (Ofatumumab) |
| Avastin (Bevacizumab) |
| Azacitidine |
| Bendamustine Hydrochloride |
| Bevacizumab |
| Bexarotene |
| Bexxar (Tositumomab and I 131 Iodine Tositumomab) |
| Bleomycin |
| Bortezomib |
| Cabazitaxel |
| Campath (Alemtuzumab) |
| Camptosar (Irinotecan Hydrochloride) |
| Capecitabine |
| Carboplatin |
| Cerubidine (Daunorubicin Hydrochloride) |
| Cervarix (Recombinant HPV Bivalent Vaccine) |
| Cetuximab |
| Chlorambucil |
| Cisplatin |
| Clafen (Cyclophosphamide) |
| Clofarabine |
| Clofarex (Clofarabine) |
| Clolar (Clofarabine) |
| Cyclophosphamide |
| Cyfos (Ifosfamide) |
| Cytarabine |
| Cytarabine, Liposomal |
| Cytosar-U (Cytarabine) |
| Cytoxan (Cyclophosphamide) |
| Dacarbazine |
| Dacogen (Decitabine) |
| Dasatinib |
| Daunorubicin Hydrochloride |
| Decitabine |
| Degarelix |
| Denileukin Diftitox |
| Denosumab |
| DepoCyt (Liposomal Cytarabine) |
| DepoFoam (Liposomal Cytarabine) |
| Dexrazoxane Hydrochloride |
| Docetaxel |
| Doxorubicin Hydrochloride |
| Efudex (Fluorouracil) |
| Elitek (Rasburicase) |
| Ellence (Epirubicin Hydrochloride) |
| Eloxatin (Oxaliplatin) |
| Eltrombopag Olamine |
| Emend (Aprepitant) |
| Epirubicin Hydrochloride |
| Erbitux (Cetuximab) |
| Eribulin Mesylate |
| Erlotinib Hydrochloride |
| Etopophos (Etoposide Phosphate) |
| Etoposide |
| Etoposide Phosphate |
| Everolimus |
| Evista (Raloxifene Hydrochloride) |
| Exemestane |
| Fareston (Toremifene) |
| Faslodex (Fulvestrant) |
| Femara (Letrozole) |
| Filgrastim |
| Fludara (Fludarabine Phosphate) |
| Fludarabine Phosphate |
| Fluoroplex (Fluorouracil) |
| Fluorouracil |
| Folex (Methotrexate) |
| Folex PFS (Methotrexate) |
| Folotyn (Pralatrexate) |
| Fulvestrant |
| Gardasil (Recombinant HPV Quadrivalent Vaccine) |
| Gefitinib |
| Gemcitabine Hydrochloride |
| Gemtuzumab Ozogamicin |
| Gemzar (Gemcitabine Hydrochloride) |
| Gleevec (Imatinib Mesylate) |
| Halaven (Eribulin Mesylate) |
| Herceptin (Trastuzumab) |

TABLE 2-continued

| Exemplary Cancer Medications |
|---|
| HPV Bivalent Vaccine, Recombinant |
| HPV Quadrivalent Vaccine, Recombinant |
| Hycamtin (Topotecan Hydrochloride) |
| Ibritumomab Tiuxetan |
| Ifex (Ifosfamide) |
| Ifosfamide |
| Ifosfamidum (Ifosfamide) |
| Imatinib Mesylate |
| Imiquimod |
| Ipilimumab |
| Iressa (Gefitinib) |
| Irinotecan Hydrochloride |
| Istodax (Romidepsin) |
| Ixabepilone |
| Ixempra (Ixabepilone) |
| Jevtana (Cabazitaxel) |
| Keoxifene (Raloxifene Hydrochloride) |
| Kepivance (Palifermin) |
| Lapatinib Ditosylate |
| Lenalidomide |
| Letrozole |
| Leucovorin Calcium |
| Leukeran (Chlorambucil) |
| Leuprolide Acetate |
| Levulan (Aminolevulinic Acid) |
| Linfolizin (Chlorambucil) |
| LipoDox (Doxorubicin Hydrochloride Liposome) |
| Liposomal Cytarabine |
| Lupron (Leuprolide Acetate) |
| Lupron Depot (Leuprolide Acetate) |
| Lupron Depot-Ped (Leuprolide Acetate) |
| Lupron Depot-3 Month (Leuprolide Acetate) |
| Lupron Depot-4 Month (Leuprolide Acetate) |
| Matulane (Procarbazine Hydrochloride) |
| Methazolastone (Temozolomide) |
| Methotrexate |
| Methotrexate LPF (Methotrexate) |
| Mexate (Methotrexate) |
| Mexate-AQ (Methotrexate) |
| Mozobil (Plerixafor) |
| Mylosar (Azacitidine) |
| Mylotarg (Gemtuzumab Ozogamicin) |
| Nanoparticle Paclitaxel (Paclitaxel Albumin-stabilized Nanoparticle Formulation) |
| Nelarabine |
| Neosar (Cyclophosphamide) |
| Neupogen (Filgrastim) |
| Nexavar (Sorafenib Tosylate) |
| Nilotinib |
| Nolvadex (Tamoxifen Citrate) |
| Nplate (Romiplostim) |
| Ofatumumab |
| Oncaspar (Pegaspargase) |
| Ontak (Denileukin Diftitox) |
| Oxaliplatin |
| Paclitaxel |
| Palifermin |
| Palonosetron Hydrochloride |
| Panitumumab |
| Paraplat (Carboplatin) |
| Paraplatin (Carboplatin) |
| Pazopanib Hydrochloride |
| Pegaspargase |
| Pemetrexed Disodium |
| Platinol (Cisplatin) |
| Platinol-AQ (Cisplatin) |
| Plerixafor |
| Pralatrexate |
| Prednisone |
| Procarbazine Hydrochloride |
| Proleukin (Aldesleukin) |
| Prolia (Denosumab) |
| Promacta (Eltrombopag Olamine) |
| Provenge (Sipuleucel-T) |
| Raloxifene Hydrochloride |
| Rasburicase |
| Recombinant HPV Bivalent Vaccine |
| Recombinant HPV Quadrivalent Vaccine |

TABLE 2-continued

| Exemplary Cancer Medications |
|---|
| Revlimid (Lenalidomide) |
| Rheumatrex (Methotrexate) |
| Rituxan (Rituximab) |
| Rituximab |
| Romidepsin |
| Romiplostim |
| Rubidomycin (Daunorubicin Hydrochloride) |
| Sclerosol Intrapleural Aerosol (Talc) |
| Sipuleucel-T |
| Sorafenib Tosylate |
| Sprycel (Dasatinib) |
| Sterile Talc Powder (Talc) |
| Steritalc (Talc) |
| Sunitinib Malate |
| Sutent (Sunitinib Malate) |
| Synovir (Thalidomide) |
| Talc |
| Tamoxifen Citrate |
| Tarabine PFS (Cytarabine) |
| Tarceva (Erlotinib Hydrochloride) |
| Targretin (Bexarotene) |
| Tasigna (Nilotinib) |
| Taxol (Paclitaxel) |
| Taxotere (Docetaxel) |
| Temodar (Temozolomide) |
| Temozolomide |
| Temsirolimus |
| Thalidomide |
| Thalomid (Thalidomide) |
| Toposar (Etoposide) |
| Topotecan Hydrochloride |
| Toremifene |
| Torisel (Temsirolimus) |
| Tositumomab and I 131 Iodine Tositumomab |
| Totect (Dexrazoxane Hydrochloride) |
| Trastuzumab |
| Treanda (Bendamustine Hydrochloride) |
| Trisenox (Arsenic Trioxide) |
| Tykerb (Lapatinib Ditosylate) |
| Vandetanib |
| Vectibix (Panitumumab) |
| Velban (Vinblastine Sulfate) |
| Velcade (Bortezomib) |
| Velsar (Vinblastine Sulfate) |
| VePesid (Etoposide) |
| Viadur (Leuprolide Acetate) |
| Vidaza (Azacitidine) |
| Vinblastine Sulfate |
| Vincasar PFS (Vincristine Sulfate) |
| Vincristine Sulfate |
| Vorinostat |
| Votrient (Pazopanib Hydrochloride) |
| Wellcovorin (Leucovorin Calcium) |
| Xeloda (Capecitabine) |
| Xgeva (Denosumab) |
| Yervoy (Ipilimumab) |
| Zevalin (Ibritumomab Tiuxetan) |
| Zinecard (Dexrazoxane Hydrochloride) |
| Zoledronic Acid |
| Zolinza (Vorinostat) |
| Zometa (Zoledronic Acid) |
| Zytiga (Abiraterone Acetate) |

TABLE 3

| Exemplary Ocular Diseases and Conditions |
|---|
| Examples of "back of the eye" diseases include |
| macular edema such as angiographic cystoid macular edema |
| retinal ischemia and choroidal neovascularization |
| macular degeneration |
| retinal diseases (e.g., diabetic retinopathy, diabetic retinal edema, retinal detachment); inflammatory |

TABLE 3-continued

| Exemplary Ocular Diseases and Conditions |
| --- |
| diseases such as uveitis (including panuveitis) or choroiditis (including multifocal choroiditis) of unknown cause (idiopathic) or associated with a systemic (e.g., autoimmune) disease; episcleritis or scleritis |
| Birdshot retinochoroidopathy |
| vascular diseases (retinal ischemia, retinal vasculitis, choroidal vascular insufficiency, choroidal thrombosis) |
| neovascularization of the optic nerve |
| optic neuritis |
| Examples of "front-of-eye" diseases include: |
| blepharitis |
| keratitis |
| rubeosis iritis |
| Fuchs' heterochromic iridocyclitis |
| chronic uveitis or anterior uveitis |
| conjunctivitis |
| allergic conjunctivitis (including seasonal or perennial, vernal, atopic, and giant papillary) |
| keratoconjunctivitis sicca (dry eye syndrome) |
| iridocyclitis |
| iritis |
| scleritis |
| episcleritis |
| corneal edema |
| scleral disease |
| ocular cicatrcial pemphigoid |
| pars planitis |
| Posner Schlossman syndrome |
| Behcet's disease |
| Vogt-Koyanagi-Harada syndrome |
| hypersensitivity reactions |
| conjunctival edema |
| conjunctival venous congestion |
| periorbital cellulitis; acute dacryocystitis |
| non-specific vasculitis |
| sarcoidosis |

TABLE 4

| Exemplary Ocular Medications |
| --- |
| Atropine |
| Brimondine (Alphagan) |
| Ciloxan |
| Erythromycin |
| Gentamicin |
| Levobunolol (Betagan) |
| Metipranolol (Optipranolol) |
| Optivar |
| Patanol |
| PredForte |
| Proparacaine |
| Timoptic |
| Trusopt |
| Visudyne (Verteporfin) |
| Voltaren |
| Xalatan |

TABLE 5

| Exemplary Diseases and Conditions affecting the Lungs |
| --- |
| Acute Bronchitis |
| Acute Respiratory Distress Syndrome (ARDS) |
| Asbestosis |
| Asthma |
| Bronchiectasis |
| Bronchiolitis |
| Bronchopulmonary Dysplasia |
| Byssinosis |

TABLE 5-continued

| Exemplary Diseases and Conditions affecting the Lungs |
| --- |
| Chronic Bronchitis |
| Coccidioidomycosis (Cocci) |
| COPD |
| Cystic Fibrosis |
| Emphysema |
| Hantavirus Pulmonary Syndrome |
| Histoplasmosis |
| Human Metapneumovirus |
| Hypersensitivity Pneumonitis |
| Influenza |
| Lung Cancer |
| Lymphangiomatosis |
| Mesothelioma |
| Nontuberculosis Mycobacterium |
| Pertussis |
| Pneumoconiosis |
| Pneumonia |
| Primary Ciliary Dyskinesia |
| Primary Pulmonary Hypertension |
| Pulmonary Arterial Hypertension |
| Pulmonary Fibrosis |
| Pulmonary Vascular Disease |
| Respiratory Syncytial Virus |
| Sarcoidosis |
| Severe Acute Respiratory Syndrome |
| Silicosis |
| Sleep Apnea |
| Sudden Infant Death Syndrome |
| Tuberculosis |

TABLE 6

| Exemplary Lung/Respiratory disease medications: |
| --- |
| Accolate |
| Accolate |
| Adcirca (tadalafil) |
| Aldurazyme (laronidase) |
| Allegra (fexofenadine hydrochloride) |
| Allegra-D |
| Alvesco (ciclesonide) |
| Astelin nasal spray |
| Atrovent (ipratropium bromide) |
| Augmentin (amoxicillin/clavulanate) |
| Avelox I.V. (moxifloxacin hydrochloride) |
| Azmacort (triamcinolone acetonide) Inhalation Aerosol |
| Biaxin XL (clarithromycin extended-release tablets) |
| Breathe Right |
| Brovana (arformoterol tartrate) |
| Cafcit Injection |
| Cayston (aztreonam for inhalation solution) |
| Cedax (ceftibuten) |
| Cefazolin and Dextrose USP |
| Ceftin (cefuroxime axetil) |
| Cipro (ciprofloxacin HCl) |
| Clarinex |
| Claritin RediTabs (10 mg loratadine rapidly-disintegrating tablet) |
| Claritin Syrup (loratadine) |
| Claritin-D 24 Hour Extended Release Tablets (10 mg loratadine, 240 mg pseudoephedrine sulfate) |
| Clemastine fumarate syrup |
| Covera-HS (verapamil) |
| Curosurf |
| Daliresp (roflumilast) |
| Dulera (mometasone furoate + formoterol fumarate dihydrate) |
| DuoNeb (albuterol sulfate and ipratropium bromide) |
| Dynabac |
| Flonase Nasal Spray |
| Flovent Rotadisk |
| Foradil Aerolizer (formoterol fumarate inhalation powder) |
| Infasurf |
| Invanz |
| Iressa (gefitinib) |
| Ketek (telithromycin) |

TABLE 6-continued

| Exemplary Lung/Respiratory disease medications: |
|---|
| Letairis (ambrisentan) |
| Metaprotereol Sulfate Inhalation Solution, 5% |
| Nasacort AQ (triamcinolone acetonide) Nasal Spray |
| Nasacort AQ (triamcinolone acetonide) Nasal Spray |
| NasalCrom Nasal Spray |
| OcuHist |
| Omnicef |
| Patanase (olopatadine hydrochloride) |
| Priftin |
| Proventil HFA Inhalation Aerosol |
| Pulmozyme (dornase alfa) |
| Pulmozyme (dornase alfa) |
| Qvar (beclomethasone dipropionate) |
| Raxar (grepafloxacin) |
| Remodulin (treprostinil) |
| RespiGam (Respiratory Syncitial Virus Immune Globulin Intravenous) |
| Rhinocort Aqua Nasal Spray |
| Sclerosol Intrapleural Aerosol |
| Serevent |
| Singulair |
| Spiriva HandiHaler (tiotropium bromide) |
| Synagis |
| Tavist (clemastine fumarate) |
| Tavist (clemastine fumarate) |
| Teflaro (ceftaroline fosamil) |
| Tequin |
| Tikosyn Capsules |
| Tilade (nedocromil sodium) |
| Tilade (nedocromil sodium) |
| Tilade (nedocromil sodium) |
| Tobi |
| Tracleer (bosentan) |
| Tri-Nasal Spray (triamcinolone acetonide spray) |
| Tripedia (Diptheria and Tetanus Toxoids and Acellular Pertussis Vaccine Absorbed) |
| Tygacil (tigecycline) |
| Tyvaso (treprostinil) |
| Vancenase AQ 84 mcg Double Strength |
| Vanceril 84 mcg Double Strength (beclomethasone dipropionate, 84 mcg) Inhalation Aerosol |
| Ventolin HFA (albuterol sulfate inhalation aerosol) |
| Visipaque (iodixanol) |
| Xolair (omalizumab) |
| Xopenex |
| Xyzal (levocetirizine dihydrochloride) |
| Zagam (sparfloxacin) tablets |
| Zemaira (alpha1-proteinase inhibitor) |
| Zosyn (sterile piperacillin sodium/tazobactam sodium) |
| Zyflo (Zileuton) |
| Zyrtec (cetirizine HCl) |

TABLE 7

| Exemplary Diseases and Conditions affecting the Heart: |
|---|
| Heart attack |
| Atherosclerosis |
| High blood pressure |
| Ischemic heart disease |
| Heart rhythm disorders |
| Tachycardia |
| Heart murmurs |
| Rheumatic heart disease |
| Pulmonary heart disease |
| Hypertensive heart disease |
| Valvular heart disease |
| Infective endocarditis |
| Congenital heart diseases |
| Coronary heart disease |
| Atrial myxoma |
| HOCM |
| Long QT syndrome |
| Wolff Parkinson White syndrome |
| Supraventricular tachycardia |
| Atrial flutter |

TABLE 7-continued

| Exemplary Diseases and Conditions affecting the Heart: |
|---|
| Constrictive pericarditis |
| Atrial myxoma |
| Long QT syndrome |
| Wolff Parkinson White syndrome |
| Supraventricular tachycardia |
| Atrial flutter |

TABLE 8

| Exemplary Heart Medications |
|---|
| ACE Inhibitors |
| acetylsalicylic acid, Aspirin, Ecotrin |
| alteplase, Activase, TPA |
| anistreplase-injection, Eminase |
| Aspirin and Antiplatelet Medications |
| atenolol, Tenormin |
| atorvastatin, Lipitor |
| benazepril, Lotensin |
| Beta Blockers |
| Bile Acid Sequestrants |
| Calcium Channel Blockers |
| captopril and hydrochlorothiazide, Capozide |
| captopril, Capoten |
| clopidogrel bisulfate, Plavix |
| colesevelam, Welchol |
| dipyridamole-oral, Persantine |
| enalapril and hydrochlorothiazide, Vaseretic |
| enalapril, Vasotec |
| ezetimibe and simvastatin, Vytorin |
| Fibrates |
| fluvastatin, Lescol |
| fosinopril sodium, Monopril |
| lisinopril and hydrochlorothiazide, Zestoretic, Prinzide |
| lisinopril, Zestril, Prinivil |
| lovastatin, Mevacor, Altocor |
| magnesium sulfate-injection |
| metoprolol, Lopressor, Toprol XL |
| moexipril-oral, Univasc |
| nadolol, Corgard |
| niacin and lovastatin, Advicor |
| niacin, Niacor, Niaspan, Slo-Niacin |
| nitroglycerin, Nitro-Bid, Nitro-Dur, Nitrostat, Transderm-Nitro, Minitran, Deponit, Nitrol |
| oxprenolol-oral |
| pravastatin, Pravachol |
| pravastatin/buffered aspirin-oral, Pravigard PAC |
| propranolol, Inderal, Inderal LA |
| quinapril hcl/hydrochlorothiazide-oral, Accuretic |
| quinapril, Accupril |
| ramipril, Altace |
| reteplase-injection, Retavase |
| simvastatin, Zocor |
| Statins |
| streptokinase-injection, Kabikinase, Streptase |
| torsemide-oral, Demadex |
| trandolapril, Mavik |

TABLE 9

| Exemplary Bacterial, Viral, Fungal and Parasitic Conditions |
|---|
| Bacterial Infections caused by: |
| *Borrelia* species |
| *Streptococcus pneumoniae* |
| *Staphylococcus aureus* |
| *Mycobacterium tuberculosis* |
| *Mycobacterium leprae* |
| *Neisseria gonorrheae* |
| *Chlamydia trachomatis* |
| *Pseudomonas aeruginosa* |

TABLE 9-continued

| Exemplary Bacterial, Viral, Fungal and Parasitic Conditions |
|---|
| Viral Infections caused by: |
| Herpes simplex |
| Herpes zoster |
| cytomegalovirus |
| Fungal Infections caused by: |
| *Aspergillus fumigatus* |
| *Candida albicans* |
| *Histoplasmosis capsulatum* |
| *Cryptococcus* species |
| *Pneumocystis carinii* |
| Parasitic Infections caused by: |
| *Toxoplasmosis gondii* |
| *Trypanosome cruzi* |
| *Leishmania* species |
| *Acanthamoeba* species |
| *Giardia lamblia* |
| *Septata* species |
| *Dirofilaria immitis* |

What is claimed is:

1. A method for treating a disease or condition in a subject in need comprising administering to said subject an effective amount of a nanoparticle, wherein said nanoparticle comprises:

a) an inner core comprising a biocompatible or a synthetic material selected from the group consisting of carboxyl-terminated poly(lactic-co-glycolic acid) (PLGA), carboxyl-terminated polylactic acid (PLA), polylysine, and polyglutamic acid; and b) an outer surface comprising a cellular membrane derived from a cell, and c) a releasable cargo that is a therapeutic agent for treating said disease or condition in said subject; and wherein after receiving said effective amount of said nanoparticle, said subject shows observable and/or measurable reduction in or absence of one or more signs and symptoms of said disease or condition.

2. The method of claim 1, wherein the inner core of the nanoparticle comprises carboxyl-terminated PLGA.

3. The method of claim 1, wherein the cellular membrane of the nanoparticle is derived from a blood cell, a tumor cell, a cancer cell, an immune cell, a stem cell, an endothelial cell, an exosome, a secretory vesicle or a synaptic vesicle.

4. The method of claim 1, wherein the cellular membrane of the nanoparticle comprises a plasma membrane derived from a red blood cell.

5. The method of claim 1, wherein the cellular membrane of the nanoparticle comprises a plasma membrane derived from a white blood cell.

6. The method of claim 1, wherein the nanoparticle further comprises a releasable cargo that is a prophylactic agent, a diagnostic or marker agent, a prognostic agent, or a combination thereof.

7. The method of claim 1, wherein the nanoparticle has a half-life in blood circulation in vivo for at least about 2-5 times of the half-life of a PEG-coated, comparable nanoparticle, or has a half-life in blood circulation in vivo for at least about 5 to about 40 hours.

8. The method of claim 1, which comprises administering to the subject an effective amount of a medicament delivery system that comprises an effective amount of the nanoparticle.

9. The method of claim 1, which comprises administering to the subject an effective amount of a pharmaceutical composition comprising an effective amount of the nanoparticle and a pharmaceutically acceptable carrier or excipient.

10. The method of claim 1, wherein the subject is a human or a non-human mammal.

11. The method of claim 1, wherein the cellular membrane in the nanoparticle is derived from a cell of the same species of the subject or is derived from a cell of the subject.

12. The method of claim 1, wherein the cellular membrane in the nanoparticle is derived from a red blood cell of the same species of the subject and the red blood cell has the same blood type of the subject.

13. The method of claim 1, which further comprises administering another therapeutic agent for treating the disease or condition to the subject in need.

14. The method of claim 1, wherein the cellular membrane is derived from a blood cell.

15. The method of claim 14, wherein the cellular membrane is derived from a red blood cell.

16. The method of claim 14, wherein the cellular membrane is derived from a white blood cell.

17. The method of claim 14, wherein the cellular membrane is derived from a platelet.

18. The method of claim 1, wherein the cellular membrane is derived from a tumor cell or a cancer cell.

19. The method of claim 1, wherein the cellular membrane is derived from an immune cell.

20. The method of claim 1, wherein the cellular membrane is derived from a stem cell.

21. The method of claim 1, wherein the cellular membrane is derived from an endothelial cell.

* * * * *